(12) United States Patent
Moriyama et al.

(10) Patent No.: US 8,278,032 B2
(45) Date of Patent: Oct. 2, 2012

(54) TRANSPORTER PROTEIN IN MAMMAL AND UTILIZATION OF THE SAME

(75) Inventors: Yoshinori Moriyama, Osaka (JP); Hiroshi Omote, Okayama (JP); Masato Otsuka, Okayama (JP); Takuya Matsumoto, Okayama (JP); Miki Hiasa, Okayama (JP)

(73) Assignee: Genomembrane, Inc., Kanagawa (JP)

( * ) Notice: Subject to any disclaimer, the term of this patent is extended or adjusted under 35 U.S.C. 154(b) by 0 days.

(21) Appl. No.: 12/817,576

(22) Filed: Jun. 17, 2010

(65) Prior Publication Data

US 2010/0279331 A1 Nov. 4, 2010

Related U.S. Application Data

(62) Division of application No. 12/089,646, filed as application No. PCT/JP2006/320409 on Oct. 12, 2006, now Pat. No. 7,892,728.

(30) Foreign Application Priority Data

Oct. 14, 2005 (JP) ................................. 2005-300851
Jun. 5, 2006 (JP) ................................. 2006-156458

(51) Int. Cl.
*C12Q 1/00* (2006.01)
*C07K 14/435* (2006.01)

(52) U.S. Cl. .......................................... 435/4; 530/350
(58) Field of Classification Search .......................... None
See application file for complete search history.

(56) References Cited

U.S. PATENT DOCUMENTS

2007/0105122 A1  5/2007  Ota et al.
2007/0224201 A1  9/2007  Wu et al.

FOREIGN PATENT DOCUMENTS

JP    2002191363    7/2002
WO    WO0234783     5/2002
WO    WO 03/089583  10/2003

OTHER PUBLICATIONS

Strausberg et al., Generation and initial analysis of more than 15,000 full-length human and mouse cDNA sequences. Proc. Natl. Acad. Sci. USA 99:16899-16903, 2002.*
Database SwissProt[online], Accession No. Q8KOH1, <<http://www.ncbi.nlm.nih.gov/entrez/viewer.fcgi?81900833:CAGE__ DDBJ:1966 641>> Jun. 1, 2003. Definition: 130013J15Rik protein.
Database SwissProt[online], Accession No. Q86VL8 <<http://www.ncbi.nlm.nih.gov/entrez/viewer.fcgi?74727585:CAGE__ DDBJ:5745 64>> Oct. 1, 2003, Definition: Hypothetical protein FLJ31196.
Database SwissProt[online], Accession No. Q8IV44 http://www.ncbi.nlm.nih.gov/entrez/viewer.fcgi?74728032:CAGE__ DDBJ:5750 17>> Jun. 1, 2003, Definition: FLJ31196 protein.
Database SwissProt[online], Accession No. Q96FL8 <<http://www.ncbi.nlm.nih.gov/entrez/viewer.fcgi?74731723:CAGE__ DDBJ:5787 35>> Jun. 1, 2003, Definition: Hypothetical protein FLJ10847.
Database SwissProt[online], Accession No. Q9NVA3 http://www.ncbi.nlm.nih.gov/entrez/viewer.fcgi?74734474:CAGE__ DDBJ:5815 02>> Jun. 1, 2003, Definition: Hypothetical protein FLJ10847.
Hvorup RN et al., "The Multidrug/oligosaccharidyl-lipid/polysaccharide (MOP) Exporter Superfamily", Eur. J. Biochem., vol. 270, No. 5, pp. 799-813, 2003.
International Preliminary Report on Patentability for PCT/JP2006/320409 dated Jun. 19, 2008.
Otsuka et al., "A Human Transporter Protein That Mediates the Final Excretion Step for Toxic Organic Cations," Proc. Natl. Acad. Sci. USA, vol. 102, No. 50, pp. 17923-17928, Dec. 2005.
Morita et al., "NorM, a Putative Multidrug Efflux Protein, of Vibrio Parahaemolyticus and Its Homolog in *Escherichia coli*," Antimircrob Agents Chemother., vol. 42, No. 7, pp. 1778-1782, 1998.

* cited by examiner

*Primary Examiner* — Ruixiang Li
(74) *Attorney, Agent, or Firm* — Margaret B. Brivanlou; King & Spalding

(57) ABSTRACT

The present invention provides a lipid membrane that contains a polypeptide consisting of the amino acid sequence of SEQ ID NO: 2, 4, 6, 8, or 22. Use of the present invention enables screening for a chemical which regulates excretion of a chemical and/or a waste. Furthermore, use of the present invention enables an arbitrary chemical to be tested for nephrotoxicity and/or hepatotoxicity.

18 Claims, 22 Drawing Sheets

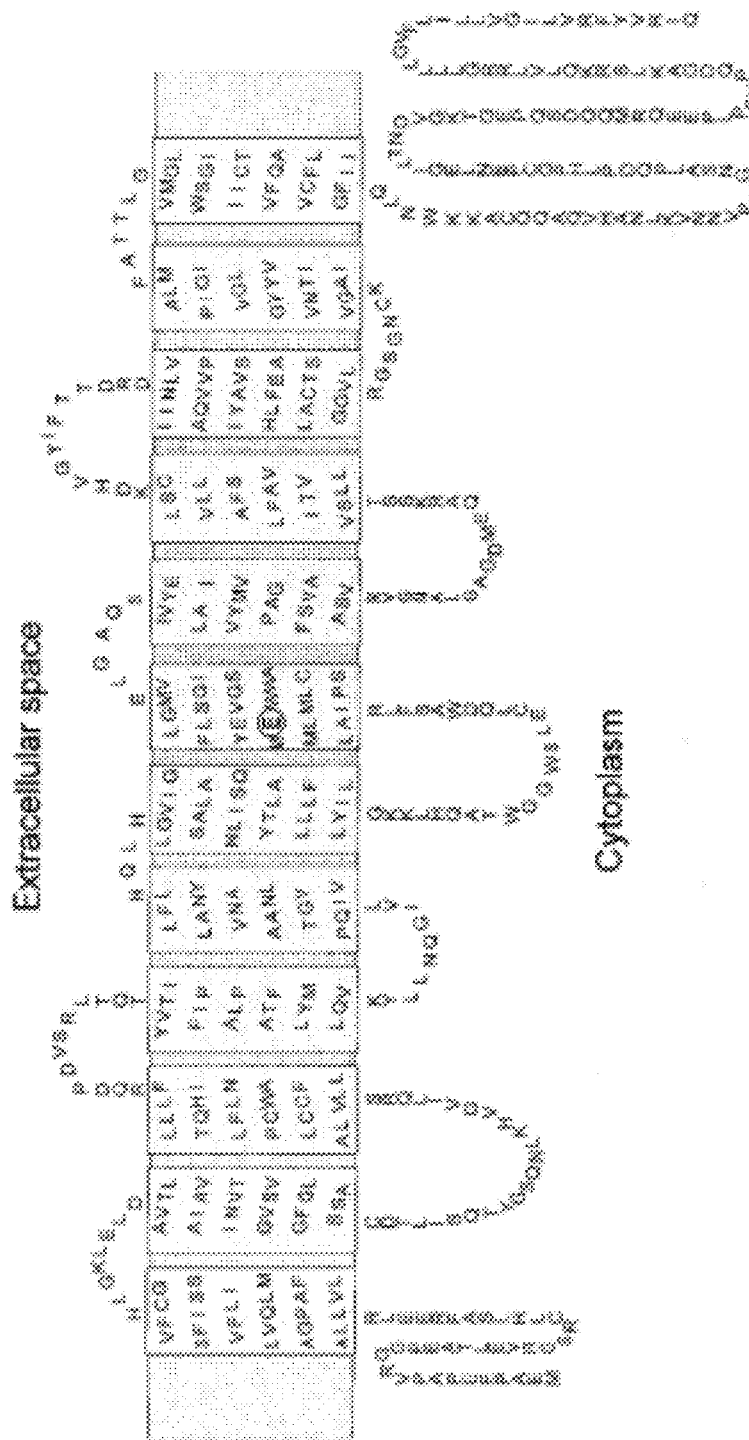

TRANSPORTER PROTEIN IN MAMMAL AND UTILIZATION OF THE SAME

TECHNICAL FIELD

This application is a divisional application of U.S. patent application Ser. No. 12/089,646, filed Jul. 7, 2008, now U.S. Pat. No. 7,892,728 issued on Feb. 22, 2011, which is the entry of the national phase under 35 U.S.C. §371 of PCT/JP2006/320409, filed Oct. 12, 2006, which claims priority to Japanese Application No. 2005-300851, filed Oct. 14, 2005, and to Japanese Application No. 2006-156458, filed Jun. 5, 2006, the contents of each of which are incorporated in their entirety. The present invention relates to a novel transporter protein in a mammal and utilization of the same. More specifically, the present invention relates to a novel organic cation transporter protein responsible for the final stage of excretion of a chemical and/or a waste and utilization of the same.

BACKGROUND ART

Organisms must process toxic substances in the environment and/or excretory metabolites. In particular, humans must process drugs and the like of a very wide variety of structures. In mammals, organic compounds having such toxicity are excreted primarily via the kidneys and/or the liver. Excretion in the kidneys occurs through filtration in the glomerulus and secretion in the renal tubules. Organic compounds having toxicity are taken up from membrane of the renal tubules cells on the vascular side and excreted from the brush border membrane side of the renal tubules cells (refer to Non-patent Documents 1 to 7). Hepatocytes also absorb organic compounds having toxicity from the sinusoidal capillary and excrete them into the capillary bile duct (refer to Non-patent Documents 1 to 7).

To date, many biochemical or biological studies have revealed that a specific transporter is responsible for the final stage of organic cation (OC) excretion and suggested the existence of an OC transporter which mediates exchange transport of electroneutral protons and OCs (refer to Non-patent Documents 5 to 7). This putative transporter is considered to be a multidrug recognizing excretion transporter since it recognizes a wide variety of OCs, several types of vitamins, or endogenous compounds (for example, choline and dopamine) including cationic chemicals.

The entity of transporters remains unknown so far, and homologues of known kidney transporters have been searched to identify its molecular entity. However, no molecule (protein) showing the intended function has been identified. That is, specifically what molecules exist as transporter proteins responsible for the final stage of organic cations (OC) excretion remains unknown, and identification of specific molecules has been awaited.

The inventors of the present invention considered that a family of proteins having the intended function may be conserved in bacteria to mammals and assumed that an orthologue of a protein which functions as a multidrug efflux pump in bacteria exists in mammals, and this orthologue is responsible for OC excretion in mammals.

Multidrug efflux pumps of bacteria are classified into several groups (for example, major facilitator superfamily [MSF], small multidrug resistance [SMR] family, resistance modulation cell division [RND] family, ATP binding cassette [ABC] family, and multidrug and toxin extrusion [MATE] family) (refer to Non-patent Documents 8 to 10).

The inventors of the present invention searched databases from their unique viewpoints, and, as a result, found out that genes encoding proteins which are likely to be classified into the MATE family proteins exist in mammals (refer to Non-patent Document 11).

[Non-patent Document 1] Pritchard, J. B. and Miller, D. S. (1993) Physiol. Rev.: 73, 765-96
[Non-patent Document 2] Ullrich, K. J. (1994) Biochim. Biophys. Acta: 1197, 45-62
[Non-patent Document 3] Oude Elferink, R. P., et al. (1995) Biochim. Biophys. Acta: 1241, 215-68
[Non-patent Document 4] Koepsell, H. (1998) Annu. Rev. Physiol.: 60, 243-66
[Non-patent Document 5] Inui, K. I. Et al., (2000) Kidney Int.: 58, 944-58
[Non-patent Document 6] Wright, S. H. and Dantzler, W. H. (2004) Physiol. Rev.: 84, 987-1049
[Non-patent Document 7] Koepsell, H. (2004) Trends Pharmacol. Sci.: 25, 375-81
[Non-patent Document 8] Brown, M. H. et al. (1999) Mol. Microbiol.: 31, 394-5
[Non-patent Document 9] Putman, M. et al. (2000) Microbiol. Mol. Biol. Rev.: 64, 672-93
[Non-patent Document 10] Hvorup, R. N. et al. (2003) Eur. J. Biochem.: 270, 799-813
[Non-patent Document 11] Genbank accession number AK001709
[Non-patent Document 12] Ito, W. et al. (1991) Gene: 1002, 67-70
[Non-patent Document 13] Morimoto, R. et al. (2003) J. Neurochem. 84: 382-91
[Non-patent Document 14] Tamai, I. Et al. (1997) FEBS Lett.: 419, 107-11
[Non-patent Document 15] Morita, Y. et al. (1998) Antimicrob. Agents Chemother.: 42, 1778-82
[Non-patent Document 16] Smith, A. C. et al. (1986) Am. J. Med. Genet.: 24, 393-414
[Non-patent Document 17] Bi, W. et al. (2002) Genome Res.: 12, 713-28

The putative amino acid sequence encoded by the gene described in Non-patent Document 11 has a very low sequence homology with the $Na^+$-dependent multidrug efflux transporter NorM of *Vibrio* bacteria, a prototype of the MATE family, and it is hard to presume that this protein is classified as a MATE family protein.

Furthermore, the MATE family is a group of recently classified-proteins required for acquisition of multidrug resistance, and only some of them are known to excrete $H^+$ or $Na^+$-dependent cationic chemicals in bacteria. That is, not only characteristics of the whole MATE family have not been elucidated yet, but there has been no assay system for identifying a target protein as a MATE family protein in mammals.

DISCLOSURE OF THE INVENTION

The present invention was accomplished in consideration of the above-mentioned problems. Objectives of the present invention are to establish an assay system for identifying MATE family proteins to find MATE family proteins in mammals and to provide a technique utilizing functions thereof.

The lipid membrane of the present invention is characterized by containing the following polypeptide: a polypeptide consisting of the amino acid sequence of SEQ ID NO: 2, 4, 6, 8, or 22; or a polypeptide consisting of an amino acid sequence wherein one or more amino acids are deleted, substituted, or added in the amino acid sequence of SEQ ID NO: 2, 4, 6, 8, or 22, and having a transporter activity in a cell membrane.

A lipid membrane of the present invention may be a naturally occurring lipid membrane or an artificial lipid membrane. A naturally occurring lipid membrane is preferably a plasma membrane (cell membrane) or a membrane vesicle, and an artificial lipid membrane is preferably a planar lipid membrane or a liposome.

The transformant of the present invention is characterized in that a polynucleotide encoding a polypeptide consisting of the amino acid sequence of SEQ ID NO: 2, 4, 6, 8, or 22; or a polypeptide consisting of an amino acid sequence wherein one or more amino acids are deleted, substituted, or added in the amino acid sequence of SEQ ID NO: 2, 4, 6, 8, or 22 and having a transporter activity, is introduced thereinto.

In the transformant of the present invention, the above-mentioned polypeptide may be a polypeptide encoded by a polynucleotide consisting of the nucleotide sequence of SEQ ID NO: 1, 3, 5, 7, or 21; or a polypeptide which is encoded by a polynucleotide consisting of a nucleotide sequence wherein one or more nucleotides are deleted, substituted, or added in the nucleotide sequence of SEQ ID NO: 1, 3, 5, 7, or 21 and has a transporter activity in a plasma membrane.

In the transformant of the present invention, the above-mentioned polypeptide may also be a polypeptide encoded by a polynucleotide consisting of the nucleotide sequence of SEQ ID NO: 1, 3, 5, 7, or 21; or a polypeptide which is encoded by a polynucleotide hybridizable with a polynucleotide consisting of a nucleotide sequence of SEQ ID NO: 1, 3, 5, 7, or 21 under a stringent condition and has a transporter activity in a plasma membrane.

In the transformant of the present invention, the above-mentioned polypeptide may also be a polypeptide encoded by a polynucleotide consisting of the nucleotide sequence of SEQ ID NO: 1, 3, 5, 7, or 21; or a polypeptide which is encoded by a polynucleotide having a homology of 80% or more with a polynucleotide consisting of the nucleotide sequence of SEQ ID NO: 1, 3, 5, 7, or 21 and has a transporter activity in a plasma membrane.

The liposome composition of the present invention is characterized by containing a polypeptide consisting of the amino acid sequence of SEQ ID NO: 2, 4, 6, 8, or 22; or a polypeptide consisting of an amino acid sequence wherein one or more amino acids are deleted, substituted, or added in the amino acid sequence of SEQ ID NO: 2, 4, 6, 8, or 22 and having a transporter activity in a plasma membrane.

In the liposome composition of the present invention, the above-mentioned polypeptide may be a polypeptide encoded by a polynucleotide consisting of the nucleotide sequence of SEQ ID NO: 1, 3, 5, 7, or 21; or a polypeptide which is encoded by a polynucleotide consisting of a nucleotide sequence wherein one or more nucleotides are deleted, substituted, or added in the nucleotide sequence of SEQ ID NO: 1, 3, 5, 7, or 21 and having a transporter activity in a plasma membrane.

In the liposome composition of the present invention, the above-mentioned polypeptide may also be a polypeptide encoded by a polynucleotide consisting of the nucleotide sequence of SEQ ID NO: 1, 3, 5, 7, or 21; or a polypeptide which is encoded by a polynucleotide hybridizable with a polynucleotide consisting of the nucleotide sequence of SEQ ID NO: 1, 3, 5, 7, or 21 under a stringent condition and has a transporter activity in a plasma membrane.

In the liposome composition of the present invention, the above-mentioned polypeptide may also be a polypeptide encoded by a polynucleotide consisting of the nucleotide sequence of SEQ ID NO: 1, 3, 5, 7, or 21; or a polypeptide which is encoded by a polynucleotide having a homology of 80% or more with a polynucleotide consisting of the nucleotide sequence of SEQ ID NO: 1, 3, 5, 7, or 21 and has a transporter activity in a plasma membrane.

The liposome composition of the present invention may further contain the $H^+$-ATPase protein. The $H^+$-ATPase protein is a protein which actively transports intracellular protons out of the cell and is also referred to as a proton pump.

The lipid membrane preparation method of the present invention is characterized by comprising the step of using a vector containing a polynucleotide coding for the following polypeptide to prepare the above-mentioned lipid membrane: a polypeptide consisting of the amino acid sequence of SEQ ID NO: 2, 4, 6, 8, or 22; or a polypeptide which consists of an amino acid sequence wherein one or more amino acids are deleted, substituted or added in an amino acid sequence of SEQ ID NO: 2, 4, 6, 8, or 22 and has a transporter activity in a cell membrane.

The lipid membrane preparation kit of the present invention is characterized by being provided with a vector containing a polynucleotide coding for the following polypeptide to prepare the above-mentioned lipid membrane: a polypeptide consisting of the amino acid sequence of SEQ ID NO: 2, 4, 6, 8, or 22; or a polypeptide which consists of an amino acid sequence wherein one or more amino acids are deleted, substituted, or added in the amino acid sequence of SEQ ID NO: 2, 4, 6, 8, or 22 and has a transporter activity in a cell membrane.

The test method of the present invention is characterized by comprising the step of incubating the above-mentioned lipid membrane together with a chemical to be evaluated in order to test a chemical for nephrotoxicity and/or hepatotoxicity.

In the above-mentioned incubation step of the test method of the present invention, it is preferable to allow tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin to coexist.

The test method of the present invention is characterized by comprising the step of incubating the above-mentioned transformant together with a substrate of a polypeptide having a transporter activity in a cell membrane, in order to test a chemical for nephrotoxicity and/or hepatotoxicity.

In the test method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The test method of the present invention is characterized by comprising the step of incubating the above-mentioned liposome composition together with a substrate of a polypeptide having a transporter activity in a cell membrane, in order to test a chemical for nephrotoxicity and/or hepatotoxicity.

In the test method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The test kit of the present invention is characterized by being provided with the above-mentioned lipid membrane, in order to test a chemical for nephrotoxicity and/or hepatotoxicity.

The test kit of the present invention may be further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The test kit of the present invention is characterized by being provided with the above-mentioned transformant, in order to test a chemical for nephrotoxicity and/or hepatotoxicity.

It is preferable that the test kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The test kit of the present invention is characterized by being provided with the above-mentioned liposome composition, in order to test a chemical for nephrotoxicity and/or hepatotoxicity.

It is preferable that the test kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening method of the present invention is characterized by comprising the step of incubating the above-mentioned lipid membrane together with a candidate factor, in order to screen for a chemical which regulates substance transport across a plasma membrane.

In the screening method of the present invention, the above-mentioned substance transport is preferably transport of nicotine, melatonin, or steroid hormones or excretion of a chemical and/or a waste.

Furthermore, in the above-mentioned incubation step of the screening method of the present invention, it is preferable to allow tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin to coexist.

The screening method of the present invention is characterized by comprising the step of incubating the above-mentioned transformant together with a substrate of a polypeptide having a transporter activity in a cell membrane, in order to screen for a chemical which regulates excretion of a chemical and/or a waste.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening method of the present invention is characterized by comprising the step of incubating the above-mentioned liposome composition together with a substrate of a polypeptide which has a transporter activity in a cell membrane, in order to screen for a chemical which regulates excretion of a chemical and/or a waste.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening method of the present invention is characterized by comprising the step of incubating the above-mentioned transformant together with a substrate of a polypeptide which has a transporter activity in a cell membrane, in order to screen for a chemical which regulates nicotine transport.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening method of the present invention is characterized by comprising the step of incubating the above-mentioned liposome composition together with a substrate of a polypeptide which has a transporter activity in a cell membrane, in order to screen for a chemical which regulates nicotine transport.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening method of the present invention is characterized by comprising the step of incubating the above-mentioned transformant together with a substrate of a polypeptide which has a transporter activity in a cell membrane, in order to screen for a chemical which regulates melatonin transport.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening method of the present invention is characterized by comprising the step of incubating the above-mentioned liposome composition together with a substrate of a polypeptide which has a transporter activity in a cell membrane, in order to screen for a chemical which regulates melatonin transport.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening method of the present invention is characterized by comprising the step of incubating the above-mentioned transformant together with a substrate of a polypeptide which has a transporter activity in a cell membrane, in order to screen for a chemical which regulates steroid hormone transport.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening method of the present invention is characterized by comprising the step of incubating the above-mentioned liposome composition together with a substrate of a polypeptide which has a transporter activity in a cell membrane to screen for a chemical which regulates steroid hormone transport.

In the screening method of the present invention, the above-mentioned substrate is preferably tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening kit of the present invention is characterized by being provided with the above-mentioned lipid membrane in order to screen for a chemical which regulates substance transport across a cell membrane.

In the screening kit of the present invention, the above-mentioned substance transport is preferably transport of nicotine, melatonin, or steroid hormones or excretion of a chemical and/or a waste.

Furthermore, the screening kit of the present invention may be further provided with tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, or thiamin.

The screening kit of the present invention is characterized by being provided with the above-mentioned transformant in order to screen for a chemical which regulates excretion of a chemical and/or a waste.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening kit of the present invention is characterized by being provided with the above-mentioned liposome composition in order to screen for a chemical which regulates excretion of a chemical and/or a waste.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening kit of the present invention is characterized by being provided with the above-mentioned transformant in order to screen for a chemical which regulates transport of nicotine.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening kit of the present invention is characterized by being provided with the above-mentioned liposome composition in order to screen for a chemical which regulates nicotine transport.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening kit of the present invention is characterized by being provided with the above-mentioned transformant in order to screen for a chemical which regulates melatonin transport.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening kit of the present invention is characterized by being provided with the above-mentioned liposome composition in order to screen for a chemical which regulates melatonin transport.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening kit of the present invention is characterized by being provided with the above-mentioned transformant in order to screen for a chemical which regulates steroid hormone transport.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening kit of the present invention is characterized by being provided with the above-mentioned liposome composition in order to screen for a chemical which regulates steroid hormone transport.

It is preferable that the screening kit of the present invention is further provided with at least one of tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

The screening method of the present invention is characterized by comprising the step of incubating the above-mentioned lipid membrane together with a candidate factor in order to screen for a substrate of a polypeptide which has a transporter activity in a cell membrane.

Furthermore, in the above-mentioned incubation step of the screening method of the present invention, it is preferable to allow tetraethylammonium (TEA) or 1-methyl-4-phenylpyridinium (MPP) to coexist.

The screening method of the present invention is characterized by comprising the step of incubating the above-mentioned transformant together with tetraethylammonium (TEA) or 1-methyl-4-phenylpyridinium (MPP) in order to screen for a substrate of a polypeptide which has a transporter activity in a cell membrane.

The screening method of the present invention is characterized by comprising the step of incubating the above-mentioned liposome composition together with tetraethylammonium (TEA) or 1-methyl-4-phenylpyridinium (MPP) in order to screen for a substrate of a polypeptide which has a transporter activity in a cell membrane.

The screening kit of the present invention is characterized by being provided with the above-mentioned lipid membrane in order to screen for a substrate of a polypeptide which has a transporter activity in a cell membrane.

Furthermore, the screening kit of the present invention may be further provided with tetraethylammonium (TEA) or 1-methyl-4-phenylpyridinium (MPP).

The screening kit of the present invention is characterized by being provided with the above-mentioned transformant in order to screen for a substrate of a polypeptide which has a transporter activity in a cell membrane.

It is preferable that the screening kit of the present invention is further provided with tetraethylammonium (TEA) or 1-methyl-4-phenylpyridinium (MPP).

The screening kit of the present invention is characterized by being provided with the above-mentioned liposome composition in order to screen for a substrate of a polypeptide which has a transporter activity in a cell membrane.

It is preferable that the screening kit of the present invention is further provided with tetraethylammonium (TEA) or 1-methyl-4-phenylpyridinium (MPP).

The screening method of the present invention is characterized by comprising the step of incubating the above-mentioned transformant together with a candidate compound in order to screen for an inhibitor or an activity enhancer of a polypeptide having a transporter activity in a cell membrane.

The screening kit of the present invention is characterized by being provided with the above-mentioned transformant in order to screen for an inhibitor or an activity enhancer of a polypeptide having a transporter activity in a cell membrane.

The screening method of the present invention is characterized by comprising the step of incubating the above-mentioned liposome composition together with a candidate compound in order to screen for an inhibitor or an activity enhancer of a polypeptide having a transporter activity in a cell membrane.

The screening kit of the present invention is characterized by being provided with the above-mentioned liposome composition in order to screen for an inhibitor or an activity enhancer of a polypeptide having a transporter activity in a cell membrane.

The diagnosis method of the present invention is characterized by comprising the step of hybridizing a fragment of any of the following polynucleotides or an oligonucleotide which consists of at least 12 continuous nucleotides complementary thereto with mRNA prepared from a biological sample in order to diagnose a disease caused by abnormal substance transport across a cell membrane:

a polynucleotide consisting of the nucleotide sequence of SEQ ID NO: 1, 3, 5, 7, or 21;

a polynucleotide consisting of a nucleotide sequence wherein one or more nucleotides are deleted, substituted, or added in the nucleotide sequence of SEQ ID NO: 1, 3, 5, 7, or 21;

a polynucleotide which hybridizes with a polynucleotide consisting of a nucleotide sequence complementary to the nucleotide sequence of SEQ ID NO: 1, 3, 5, 7, or 21 under a stringent condition; or a polynucleotide consisting of a nucleotide sequence at least 80% identical to the nucleotide sequence of SEQ ID NO: 1, 3, 5, 7, or 21.

In the diagnosis method of the present invention, the above-mentioned oligonucleotide preferably consists of any one of the nucleotide sequences of SEQ ID NOS: 11 to 18.

The diagnosis kit of the present invention is characterized by being provided with an oligonucleotide which is a fragment of any of the following polynucleotides or an oligonucleotide which consists of at least 12 continuous nucleotides complementary thereto in order to diagnose a disease caused by abnormal substance transport across a cell membrane:

a polynucleotide consisting of the nucleotide sequence of SEQ ID NO: 1, 3, 5, 7, or 21;

a polynucleotide consisting of a nucleotide sequence wherein one or more nucleotides are deleted, substituted, or added in the nucleotide sequence of SEQ ID NO: 1, 3, 5, 7, or 21;

a polynucleotide which hybridizes with a polynucleotide consisting of a nucleotide sequence complementary to the nucleotide sequence of SEQ ID NO: 1, 3, 5, 7, or 21 under a stringent condition; or a polynucleotide consisting of a nucleotide sequence at least 80% identical to the nucleotide sequence of SEQ ID NO: 1, 3, 5, 7, or 21.

In the diagnosis kit of the present invention, the above-mentioned oligonucleotide preferably consists of any one of nucleotide sequences of SEQ ID NOS: 11 to 18.

The diagnosis method of the present invention is characterized by comprising the step of incubating an antibody specifically binding to any of the following polypeptides together with a biological sample in order to diagnose a disease caused by abnormal substance transport across a cell membrane:

a polypeptide consisting of the amino acid sequence of SEQ ID NO: 2, 4, 6, 8, or 22; or a polypeptide which consists of an amino acid sequence wherein one or more amino acids are deleted, substituted, or added in the amino acid sequence of SEQ ID NO: 2, 4, 6, 8, or 22 and has a transporter activity in a cell membrane.

In the diagnosis method of the present invention, the above-mentioned antibody is preferably elicited by a peptide consisting of the amino acid sequence of SEQ ID NO: 19 or 20.

The diagnosis method of the present invention is characterized by comprising the step of using an antibody specifically binding to a polypeptide having a transporter activity in a cell membrane in order to diagnose a disease caused by abnormal substance transport involving a polypeptide having a transporter activity in a cell membrane, wherein the polypeptide is a polypeptide consisting of the amino acid sequence of SEQ ID NO: 2, 4, 6, 8, or 22 or a polypeptide which consists of an amino acid sequence wherein one or more amino acids are deleted, substituted or added in the amino acid sequence of SEQ ID NO: 2, 4, 6, 8, or 22 and has a transporter activity in a cell membrane.

The diagnosis kit of the present invention is characterized by being provided with an antibody specifically binding to any of the following polypeptides in order to diagnose a disease caused by abnormal substance transport across a cell membrane:

a polypeptide consisting of the amino acid sequence of SEQ ID NO: 2, 4, 6, 8, or 22; or a polypeptide which consists of an amino acid sequence wherein one or more amino acids are deleted, substituted, or added in the amino acid sequence of SEQ ID NO: 2, 4, 6, 8, or 22 and has a transporter activity in a cell membrane.

In the diagnosis kit of the present invention, the above-mentioned antibody is preferably elicited by a peptide consisting of the amino acid sequence of SEQ ID NO: 19 or 20.

The diagnostic kit of the present invention is characterized by being provided with an antibody specifically binding to a polypeptide having a transporter activity in a cell membrane in order to diagnose a disease caused by abnormal substance transport involving a polypeptide having a transporter activity in a cell membrane, wherein the polypeptide is a polypeptide consisting of the amino acid sequence of SEQ ID NO: 2, 4, 6, 8, or 22, or a polypeptide which consists of an amino acid sequence wherein one or more amino acids are deleted, substituted or added in the amino acid sequence of SEQ ID NO: 2, 4, 6, 8, or 22 and has a transporter activity in a cell membrane.

The polypeptide of the present invention is characterized by being a polypeptide consisting of the amino acid sequence of SEQ ID NO: 22, or a polypeptide which consists of an amino acid sequence wherein one or more amino acids are deleted, substituted, or added in the amino acid sequence of SEQ ID NO: 22 and has a transporter activity in a cell membrane.

The polynucleotide of the present invention is characterized by encoding the above-mentioned polypeptide.

Furthermore, the polynucleotide of the present invention can be a polynucleotide consisting of the nucleotide sequence of SEQ ID NO: 21; a polynucleotide consisting of a nucleotide sequence wherein one or more nucleotides are deleted, substituted, or added in the nucleotide sequence of SEQ ID NO: 21; a polynucleotide hybridizable with a polynucleotide consisting of a nucleotide sequence complementary to the nucleotide sequence of SEQ ID NO: 21 under a stringent condition; or a polynucleotide consisting of a nucleotide sequence being at least 80% identical to the nucleotide sequence of SEQ ID NO: 21.

The vector of the present invention is characterized by comprising the above-mentioned polynucleotide.

The transformant of the present invention is characterized by comprising the above-mentioned polynucleotide.

The antibody of the present invention is characterized by specifically binding to the above-mentioned polypeptide.

The knockout animal of the present invention is characterized in that the expression of a polypeptide consisting of the amino acid sequence of SEQ ID NO: 2, 4, 6, 8, or 22 is inhibited, and it is preferably a mouse.

Other objectives, features, and advantages of the present invention will be fully understood from the following descriptions. Furthermore, benefits of the present invention will be apparent from the following description with reference to the accompanying drawings.

BRIEF DESCRIPTION OF DRAWINGS

FIG. 3 is a scheme showing a putative secondary structure of hMATE1. In the figure, the glutamic acid residue (E273), which is important for a transport activity, is encircled.

FIG. 4(*b*) shows the results of the western blot analysis confirming the expression of hMATE1 using an anti-hMATE1 antibody. The anti-hMATE1 antibody specifically recognizes hMATE1 expressed in the HEK293 cell. Furthermore, a protein having an identical size exists in the kidneys, and detection of this protein by the anti-hMATE1 antibody is absorbed by the antigen peptide (N461-R546 of hMATE1).

FIG. 4(*c*) shows the results of the immunohistochemistry of hMATE1 in the kidneys. A human specimen section was stained by the HRP-DAB method. In the figure, PCT denotes proximal renal tubule, and DCT denotes distal renal tubule. The bar is 100 μm.

FIG. 4(*d*) shows the results of the immunohistochemistry of hMATE1 in the liver. The human sample section was stained by the HRP method. The bar is 100 μm.

FIG. 7(*b*) shows the results of the western blot analysis using an anti-mMATE1 antibody confirming the expression of mMATE1. The anti-mMATE1 antibody specifically recognizes mMATE1 expressed in the HEK293 cell. Furthermore, a protein having an identical size exists in the kidneys and the liver.

FIG. 7(*c*) shows the results of the immunohistochemistry of mMATE1 in the kidneys. A mouse specimen section was stained by the HRP-DAB method. mMATE1 is expressed in the renal cortex. In the figure, GL denotes glomerulus, PCT denotes proximal renal tubule, DCT denotes distal renal tubule, and CCD denotes cortical collecting duct. The bar is 100 μm.

BEST MODE OF CARRYING OUT THE INVENTION

Figure 1:
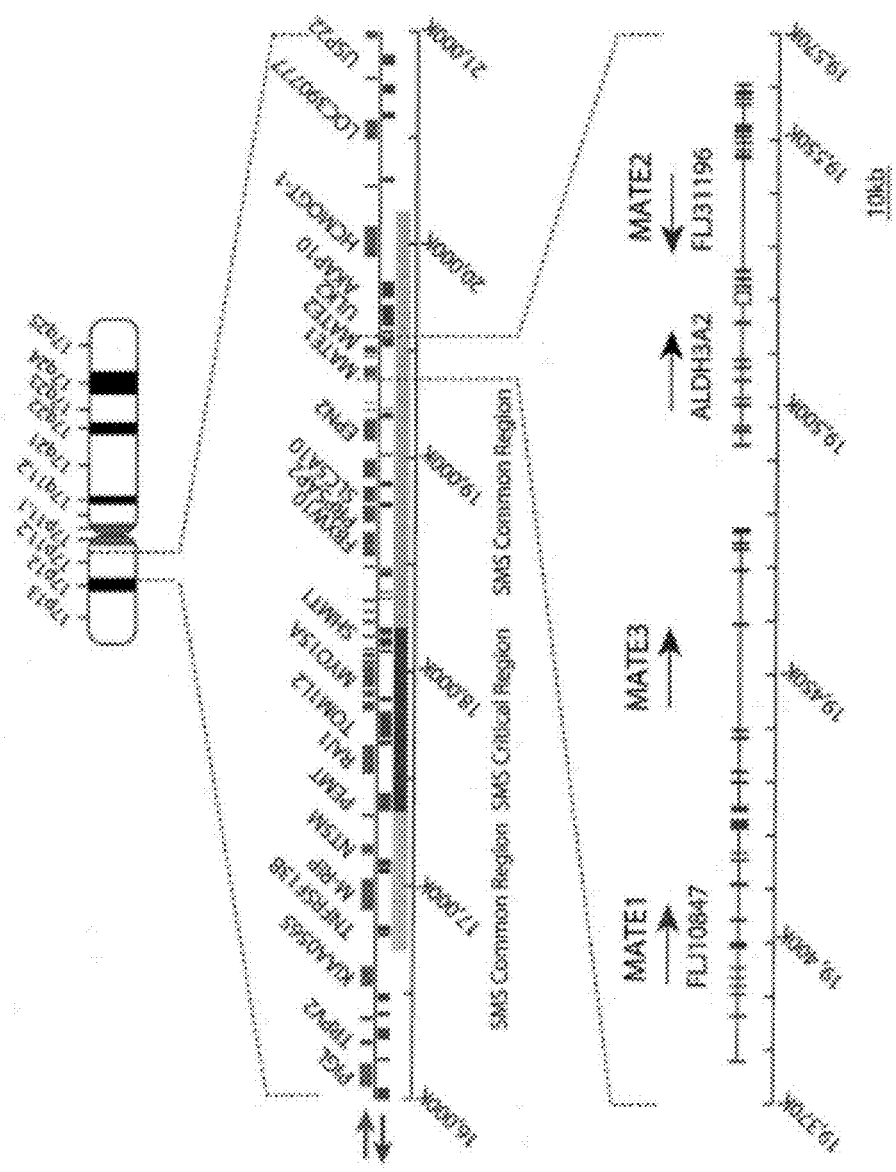
FIG. 1 shows positions and constitutions of the hMATE1 gene, the hMATE2 gene, and the hMATE3 gene on the chromosome.

To confirm that the protein that is presumed to be encoded by the genes described in Non-patent Document 11 actually exists in mammals, and that the proteins are MATE family proteins, the inventors of the present invention attempted to obtain the genes from mammals and constructed an assay system necessary for confirming the function as a MATE family protein.

Various primers were designed based on the above-mentioned nucleotide sequence information of the genes, and RT-PCR was attempted using mammal tissues. However, since little information about MATE family molecules have been obtained, and, in particular, no specific function domain exists in MATE family molecules, there was no guideline for designing preferable primers.

However, the inventors of the present invention repeated trials and errors to verify the reliability of their unique focus. As a result, they finally found that target genes can be amplified using specific primers.

Thus, the inventors of the present invention found that the genes obtained based on their unique focus and trials and errors exist in humans and mice, and the proteins encoded by these genes exist in lumen-side membranes of the renal tubules in the kidneys and the bile duct and function as novel transporters.

That is, the inventors of the present invention identified mammal MATE polypeptides, orthologues of the bacteria-derived MATE family in humans and mice, and found that the mammal MATE polypeptides are expressed in the kidneys and/or liver and are responsible for the final stage of excretion of organic cationic compounds by exchange transport with protons. Thus, the present invention was accomplished.

[1] Mammal Mate Polypeptides and Polynucleotides

The inventors of the present invention found that an orthologue of the toxic substance excretion transporter found in the bacteria exist in mammals, isolated the cDNA thereof, and analyzed the functions thereof.

The present invention provides mammal MATE polypeptides. The term "MATE polypeptide" used in the present specification is used interchangeably with "MATE protein" or "MATE family protein" and means a polypeptide that has the MATE activity, in other words, a polypeptide having a transporter activity (transport activity) of transporting organic cations (OCs) via a cell membrane. That is, the term "MATE activity" used in the present specification means a transporter activity in a cell membrane (activity of transporting a substance via cell membrane), more specifically, a transporter activity (transport activity) of transporting organic cations (OCs) via a cell membrane.

The term "polypeptide" used in the present specification is used interchangeably with "peptide" or "protein." Furthermore, the "fragment" of a polypeptide means a partial fragment of the polypeptide. The polypeptide of the present invention may be chemically synthesized or isolated from a natural supply source.

The term "isolated" polypeptide or protein means a polypeptide or a protein retrieved from the natural environment. For example, a recombinant polypeptide or protein expressed in the host cell is considered to be isolated as in the case of a natural or recombinant polypeptide or protein substantially purified by an arbitrary appropriate technique.

The polypeptides of the present invention include natural purification products, chemical synthesis products, and products produced by prokaryotic hosts or eukaryotic hosts (including bacteria cells, yeast cells, higher plant cells, insect cells, and mammal cells) using recombination techniques.

The polypeptide of the present invention may be obtained by introducing the polynucleotide of the present invention described later (the gene encoding the polypeptide of the present invention) into a host cell and expressing the polypeptide in the cell or by isolation from a cell, a tissue, or the like and purification.

Furthermore, the polypeptide of the present invention may contain an additional peptide. Examples of the additional peptide include peptides labeled with an epitope such as His, Myc, or Flag. In a preferable embodiment, the polypeptide of the present invention can be expressed as a recombinant in a modified form such as a fusion protein. For example, since additional amino acids of the peptide of the present invention, in particular, a region of charged amino acids can be added to the N or C terminus of the polypeptide to improve stability and prolonged-action in the host cell during purification or subsequent procedures and storage.

Preferably, the mammal MATE polypeptide of the present invention can be a polypeptide consisting of the amino acid sequence of SEQ ID NO: 2, 4, 6, 8, or 22 or a mutant thereof. As the above-mentioned mammals, humans or mice are preferred. The term "mutant" used for a polypeptide or a protein in the present specification means a polypeptide or a protein having the MATE activity. The amino acid sequences of the human MATE1 polypeptide (hMATE1), the human MATE2 polypeptide (hMATE2), the mouse MATE1 polypeptide (mMATE1), the mouse MATE2 polypeptide (mMATE2), and the human MATES polypeptide (hMATE3) are shown in SEQ ID NOS: 2, 4, 6, 8, and 22, respectively. Furthermore, the hMATE3 polypeptide is a novel polypeptide that has been unknown.

In one embodiment, the polypeptide of the present invention is a MATE polypeptide or a mutant thereof. Here, the mutant is preferably a polypeptide having the MATE activity, which consists of an amino acid sequence wherein one or more amino acids are deleted, substituted, or added in the amino acid sequence of SEQ ID NO: 2, 4, 6, 8, or 22.

Examples of such mutant include mutants having deletion, insertion, inversion, repetition, and type substitution (for example, substitution of a hydrophilic residue by another residue. Usually, however, a highly hydrophilic residue is not substituted by a highly hydrophobic residue). In particular, "neutral" amino acid substitution in a polypeptide generally has almost no effect on the activity of the polypeptide.

It is known in this field that several amino acids in the amino acid sequence of a polypeptide can be easily modified without significantly affecting the structure or the function of this polypeptide. Furthermore, it is also known that there are not only artificially modified polypeptides, but also naturally occurring protein mutants in which the structure or the function of the protein is not significantly changed.

Those skilled in the art can easily mutate one or several amino acids in the amino acid sequence of a polypeptide using a known technique. For example, an arbitrary nucleotide in a polynucleotide encoding a polypeptide can be mutated according to a known point mutagenesis method. Furthermore, a deletion mutant or an addition mutant can be prepared by designing primers corresponding to an arbitrary site in a polynucleotide encoding a polypeptide. Furthermore, using the methods described in the present specification, it can be easily determined whether the prepared mutant has a desired MATE activity.

Preferred mutants have conservative or nonconservative substitution, deletion, or addition of amino acids. Silent substitution, addition, and deletion are preferred, and conservative substitution is particularly preferred. These mutations do not change the MATE activity of the polypeptide of the present invention.

Representative conservative substitutions appear to include substitution of one amino acid by another amino acid among aliphatic amino acids, Ala, Val, Leu, and Ile, exchange of hydroxyl residues, Ser and Thr, exchange of acidic residues, Asp and Glu, substitution between amide residues, Asn and Gln, exchange of basic residues, Lys and Arg, and substitution between aromatic residues, Phe and Tyr.

In one embodiment, the polypeptide of the present invention is a MATE polypeptide or a mutant thereof. Here, the mutant is preferably a polypeptide which has the MATE activity and is encoded by a polynucleotide consisting of a nucleotide sequence wherein one or more nucleotides are deleted, substituted, or added in the nucleotide sequence of SEQ ID NO: 1, 3, 5, 7, or 21.

In another embodiment, the polypeptide of the present invention is a MATE polypeptide or a mutant thereof. Here, the mutant is preferably a polypeptide which has the MATE activity and is encoded by a polynucleotide hybridizable with a polynucleotide consisting of a nucleotide sequence complementary to the nucleotide sequence of SEQ ID NO: 1, 3, 5, 7, or 21 under a stringent condition.

Hybridization can be performed by known methods such as the method described in Sambrook et al., Molecular Cloning, A Laboratory Manual, 2d Ed., Cold Spring Harbor Laboratory (1989). Usually, stringency increases (becomes hard to hybridize) at a higher temperature or at a lower salt concentration, resulting in obtaining of a more homologous polynucleotide. An appropriate hybridization temperature varies depending on the nucleotide sequence and the length of the nucleotide sequence. For example, when a DNA fragment consisting of 18 nucleotides coding for six amino acids is used as a probe, temperature is preferably 50° C. or below.

The term "stringent (hybridization) condition" used in the present specification means that polynucleotides are incubated in a hybridization solution (containing 50% formamide, 5×SSC [150 mM NaCl, 15 mM trisodium citrate], 50 mM sodium phosphate [pH 7.6], 5×Denhart's solution, 10% dextran sulfate, and 20 µg/ml sheared denatured salmon sperm DNA) overnight at 42° C., and then the filter is washed with 0.1×SSC at about 65° C. A polynucleotide hybridizable with "a part" of the polynucleotide means a polynucleotide (either DNA or RNA) hybridizable with at least about 15 nucleotides (nt) of the reference polynucleotide, more preferably at least about 20 nt, yet more preferably at least about 30 nt, yet more preferably longer than about 30 nt. The polynucleotide (oligonucleotide) hybridizable with "a part" of such polynucleotide is also useful as a detection probe discussed in detail in the present specification.

In another embodiment, the polypeptide of the present invention is a MATE polypeptide or a mutant thereof. Here, the mutant is preferably a polypeptide that has the MATE activity and is encoded by a polynucleotide consisting of a nucleotide sequence at least 80% identical, more preferably at least 85%, 90%, 92%, 95%, 96%, 97%, 98%, or 99% identical to the nucleotide sequence of SEQ ID NO: 1, 3, 5, 7, or 21.

For example, the expression "a polynucleotide consisting of a nucleotide sequence at least 95% identical to the reference (QUERY) nucleotide sequence of a polynucleotide coding for the polypeptide of the present invention" means that the target nucleotide sequence is identical to the reference sequence except that it can comprises up to five mismatches per 100 nucleotides (bases) of the reference nucleotide sequence of the polynucleotide coding for the polypeptide of the present invention. In other words, to obtain a polynucleotide consisting of a nucleotide sequence at least 95% identical to the reference nucleotide sequence, up to 5% of nucleotides in the reference sequence can be deleted or substituted by another nucleotide, or many nucleotides which account for up to 5% of all nucleotides in the reference sequence can be inserted into the reference sequence. These mismatches in the reference sequence can occur anywhere between the two ends, for example, mismatches are dispersed at the 5' or 3' end position of the reference nucleotide sequence, at individual nucleotides in the reference sequence, or in a group of one or more adjacent nucleotides in the reference sequence.

The present invention also provides MATE polynucleotides. The term "MATE polynucleotide" used in the present specification means a polynucleotide consisting of the nucleotide sequence of SEQ ID NO: 1, 3, 5, 7, or 21 or a mutant thereof. The term "mutant" of DNA or polynucleotide used in the present specification means a polynucleotide coding for a polypeptide having the MATE activity. The nucleotide sequences of human MATE1 polynucleotide, the human MATE2 polynucleotide, the mouse MATE1 polynucleotide, the mouse MATE2 polynucleotide, and the human MATE3 polynucleotide are shown in SEQ ID NOS: 1, 3, 5, 7, and 21, respectively. Furthermore, the hMATE3 polynucleotide is a novel polynucleotide that has been unknown.

The term "polynucleotide" used in the present specification can be used interchangeably with "gene" "nucleic acid" or "nucleic acid molecule" and means a nucleotide polymer. The term "nucleotide sequence" used in the present specification is used interchangeably with "nucleic acid sequence" or "base sequence", and represented by a sequence of deoxyribonucleotides (abbreviated as A, G, C, and T) or ribonucleotides (C, A, G, and U). Furthermore, the expression "polynucleotide comprising the nucleotide sequence of SEQ ID NO: 1 or a fragment thereof" means a polynucleotide comprising a sequence represented by deoxynucleotides A, G, C, and/or T in SEQ ID NO: 1 or a fragment portion thereof.

The polynucleotide of the present invention can exist in the form of RNA (for example, mRNA) or in the form of DNA (for example, cDNA or genomic DNA). DNA can be double-stranded or single-stranded. A single-stranded DNA or RNA can be a coding strand (also known as a sense strand) or a noncoding strand (also known as an antisense strand).

The term "oligonucleotide" used in the present specification means several to several tens of nucleotides which are bound together and is used interchangeably with "polynucleotide". A short oligonucleotide is referred to as dinucleotide (dimer) or trinucleotide (trimer), and longer ones are represented by the number of polymerized nucleotides such as 30 mer or 100 mer. An oligonucleotide may be generated as a fragment of a longer polynucleotide or chemically synthesized.

The polynucleotide of the present invention can be fused with a polynucleotide coding for the above-mentioned tag label (tag sequence or marker sequence) at the 5' or 3' end side thereof.

In one embodiment, the polynucleotide of the present invention is a MATE polynucleotide or a mutant thereof. Here, the mutant preferably codes for a MATE polypeptide and is any of the following polynucleotides:

a polynucleotide consisting of a nucleotide sequence wherein one or more nucleotides are deleted, substituted, or deleted in the nucleotide sequence of SEQ ID NO: 1, 3, 5, 7, or 21;

a polynucleotide hybridizable with a polynucleotide consisting of a nucleotide sequence complementary to the nucleotide sequence of SEQ ID NO: 1, 3, 5, 7, or 21 under a stringent condition; and a polynucleotide consisting of a nucleotide sequence at least 80% identical, more preferably at least 85%, 90%, 92%, 95%, 96%, 97%, 98%, or 99% identical to the nucleotide sequence of SEQ ID NO: 1, 3, 5, 7, or 21.

In another embodiment, the polynucleotide of the present invention is characterized by being amplified from the human cDNA library using a primer pair of a primer consisting of the nucleotide sequence of SEQ ID NO: 11 and a primer consisting of the nucleotide sequence of SEQ ID NO: 12 or a primer pair of a primer consisting of the nucleotide sequence of SEQ ID NO: 13 and a primer consisting of the nucleotide sequence of SEQ ID NO: 14, or a polynucleotide amplified from the mouse cDNA library using a primer pair of a primer consisting of the nucleotide sequence SEQ ID NO: 15 and a primer consisting of the nucleotide sequence of SEQ ID NO: 16 or a primer pair of a primer consisting of the nucleotide sequence of SEQ ID NO: 17 and a primer consisting of the nucleotide sequence of SEQ ID NO: 18, and coding for a polypeptide having the MATE activity.

The polynucleotide of the present invention may comprise sequences such as the sequence of an untranslated region (UTR) or a vector sequence (including the expression vector sequence).

Supply sources to obtain the polynucleotide of the present invention are not particularly limited, but biological materials (for example, organs of a human or a mouse) are preferred. The term "biological materials" used in the present specification means biological samples (tissue or cell samples obtained from an organism).

As described in the present specification, the polypeptide or the polynucleotide of the present invention can be used as a tool for determining the MATE activity.

That is, an objective of the present invention is to provide MATE polypeptides and MATE polynucleotides, not the polypeptide preparation methods, the polynucleotide preparation methods, and the like specifically described in the present specification. Therefore, it should be noted that MATE polypeptides and MATE polynucleotides obtained by methods other than any of the above-mentioned methods are also encompassed in the technical scope of the present invention.

[2] Utilization of Polypeptide and Polynucleotide

[2-1] Vector

The present invention provides a vector used for generation of a MATE polypeptide. The vector of the present invention may be a vector used for in vitro translation or a vector used for recombinant expression.

The vector of the present invention is not particularly limited so long as it comprises the above-mentioned polynucleotide of the present invention. Examples thereof include recombinant expression vectors into which cDNA of a polynucleotide coding for a polypeptide having the MATE activity (MATE polynucleotide) is inserted and so forth. Examples of the recombinant expression vector preparation method include, but are not particularly limited to, methods using a plasmid, a phage, or a cosmid.

Specific types of the vector are not particularly limited, and vectors expressible in a host cell can be suitably selected. Specifically, a suitable promoter sequence is selected depending on the type of the host cell to reliably express the polynucleotide of the present invention, and a vector obtained by incorporating this sequence and the polynucleotide of the present invention into various plasmids or the like can be used as an expression vector. Furthermore, the host can also be transformed with an expression vector by conventional methods.

A host transformed with the above-mentioned expression vector can be cultured, cultivated or bred, and then a target protein can be recovered from a culture and purified using conventional methods (for example, filtration, centrifugation, cell crush, gel filtration chromatography, ion exchange chromatography, etc.).

The expression vector preferably comprises at least one selection marker. Examples of such markers include dihydrofolic acid reductase or neomycin resistance for eukaryotic cell culture, as well as the tetracycline-resistance gene or the ampicillin resistance gene for culture of E. coli and other bacteria.

By using the vector of the present invention, a MATE polypeptide can be expressed in an organism or a cell by introducing the MATE polynucleotide into the organism or the cell. Furthermore, a MATE polypeptide can be synthesized by using the vector of the present invention in a cell-free protein synthesis system.

Thus, it is sufficient that the vector of the present invention comprises at least a polynucleotide coding for the polypeptide of the present invention. That is, it should be noted that vectors other than expression vectors are also encompassed in the technical scope of the present invention.

[2-2] Lipid membrane

The present invention provides a lipid membrane containing a MATE polypeptide. The lipid membrane of the present invention may be a naturally occurring lipid membrane or an artificial lipid membrane. When the lipid membrane of the present invention is naturally occurring, it is sufficient that the membrane is a cell membrane or a membrane vesicle. When the lipid membrane of the present invention is artificial, it is sufficient that the membrane is a planar lipid membrane or a liposome (liposome composition).

(a) Transformant

In one embodiment, the lipid membrane of the present invention can be a plasma membrane of a transformant into which a polynucleotide coding for a MATE polypeptide is introduced. The term "transformant" used in the present specification means not only a cell, a tissue, or an organ, but includes an organism.

The transformant of this embodiment is characterized in that a plasma membrane containing a MATE polypeptide is formed. It is preferable that a MATE polypeptide is stably expressed in the transformant in the present embodiment.

In one aspect, the transformant of this embodiment is obtained by introducing a recombinant vector containing a MATE polynucleotide into an organism so that the MATE polypeptide can be expressed. The transformant in this embodiment may be a prokaryote or a eukaryote. Since the analysis by the inventors of the present invention showed that a MATE polypeptide is a membrane protein, a plasma membrane containing a MATE polypeptide is provided in a transformant in which a MATE polypeptide is expressed.

The method for introducing the above-mentioned expression vector into a host, that is, the transformation method is not particularly limited, and conventionally known methods such as electroporation, the calcium phosphate method, the liposome method, and the DEAE dextran method can be suitably used. Furthermore, for example, to transform an insect cell with the polypeptide of the present invention, an expression system using baculovirus can be used. To transform a plant with the polypeptide of the present invention, a polynucleotide coding for the polypeptide of the present invention can be introduced by the *Agrobacterium* method or the gene gun method (particle bombardment method).

Thus, it is sufficient that at least a plasma membrane containing the polypeptide of the present invention is formed in the transformant of the present embodiment. That is, it should be noted that transformants prepared by known methods other than the above-mentioned methods are also encompassed in the technical scope of the present invention.

(b) Membrane Vesicle

In one embodiment, the lipid membrane of the present invention can be a membrane vesicle obtained from a cell into which a polynucleotide coding for a MATE polypeptide is introduced. The "membrane vesicle" used in the present specification means a smaller vesicle formed by a plasma membrane of a cell subjected to ultrasonication or the like and destroyed.

Thus, it is sufficient that the membrane vesicle of the present embodiment is at least formed by a lipid membrane containing the polypeptide of the present invention. That is, it should be noted that membrane vesicles containing an intracellular organelle that has lost the function thereof or the like are also encompassed in the technical scope of the present invention.

(c) Liposome and Liposome Composition

A MATE polypeptide is a transporter that transports various organic cations (OCs). So far, the inventors of the present invention examined substances transported by the MATE polypeptide in a system of the HEK293 cell or Africa *Xenopus laevis* oocyte in which MATE polypeptide was expressed using radiolabeled substrates. In such a system using expression cells, many cell-derived proteins coexist in addition to the MATE polypeptide, and interference of many coexisting proteins is particularly problematic when highly hydrophobic transport substrates such as sex hormones or the like are used. That is, to measure highly hydrophobic transport substrates with high reliability, it is preferable to use a system in which no protein other than the MATE polypeptide exists.

Furthermore, since labeled substances (specifically, radiolabeled substances or fluorescence-labeled substances) are used as transport substrates in the above-described experimental system, transport of transporter proteins which transport chemicals, toxic substances, metabolic biological components, and the like which cannot be labeled could not be confirmed.

Therefore, the inventors of the present invention prepared almost proteomically uniform MATE polypeptides and a liposome in which they are incorporated (so-called proteoliposome) and completed a MATE polypeptide transport assay system constituted by a completely defined composition by subjecting this proteoliposome to a transport experiment. Then, by using a mass spectroscopy (a mass spectrometer), a fluorescence spectrometer, HPLC, and the like in combination, this transport assay system can correctly examine whether various unlabeled compounds can serve as transport substrates, which has been impossible so far.

Specifically, in one embodiment, the lipid membrane of the present invention can be a liposome composition containing a MATE polypeptide. The term "liposome composition" used in the present specification means a liposome containing a specific substance. A liposome is an artificial lipid membrane also referred to as a vesicle and can be prepared by dispersing suspension of lipids (for example, phospholipids) by vigorously stirring and performing ultrasonication. Liposomes are widely used for studies and utilized as a cell membrane model or as one of measures for a drug delivery system (DDS).

The liposome composition of the present invention is characterized by containing a MATE polypeptide. The liposome composition of the present invention may further contain the H$^+$-ATPase protein. The H$^+$-ATPase protein is a protein which actively transports intracellular protons out of the cell and is also referred to as a proton pump. The method for purifying the proton pump is not particularly limited, and conventionally known methods such as the method described in Moriyama Y et al., J. Biol. Chem. 266, 22141-22146 (1991) can be suitably used. When the transport activity of the MATE polypeptide is determined using the liposome composition of the present invention, the activity of a mammal-derived MATE polypeptide can be determined even in the absence of the H$^+$-ATPase protein.

Since a system in which no contaminating protein exists along with the MATE polypeptide can be constructed by using the present invention, it can be clearly shown whether obtained results are attributable to the MATE polypeptide, and to what extent substrate transport by the MATE polypeptide is interfered can be found by coexistence of a large number of proteins can be known.

Furthermore, a system which does not require radiolabeled or fluorescence-labeled substrates can be constructed by using the present invention, a wide variety of various chemicals, toxic substances, metabolic biological components, and the like can be analyzed for whether they are transported by transporter proteins.

Thus, conventional problems can be solved by the present invention, and transport functions of the MATE polypeptides can be more broadly and deeply understood. It is needless to say that conventional labeled compounds can also be used together with the present invention.

Thus, it is sufficient that the liposome composition of the present invention comprises at least the polypeptide of the present invention. That is, it should be noted that liposome compositions prepared by known methods other than the above-mentioned methods are also encompassed in the technical scope of the present invention.

(d) Planar Lipid Membrane

In one embodiment, the lipid membrane of the present invention can be a planar lipid membrane containing a MATE polypeptide. The lipid bilayer has a membranous structure having two layers of polar lipids (in particular, phospholipids). The lipid bilayer structure is stabilized as a two-dimensional structure when it is spherical. However, when the end is isolated from water molecules, a planar structure can be formed. Among artificially prepared lipid bilayers used in the present specification, a spherical lipid bilayer is referred to as liposome, and a planar lipid bilayer is referred to as planar lipid membrane.

To obtain the planar lipid membrane of this embodiment, a MATE polypeptide can be embedded in an artificially formed lipid bilayer membrane. Artificial lipid bilayers are used when activities of membrane proteins (for example, channel proteins) are measured in vitro, and all the preparation methods are known in this field.

Thus, it is sufficient that the planar lipid membrane of the present invention comprises at least the polypeptide of the present invention. That is, it should be noted that planar lipid membranes prepared by known methods other than the above-mentioned method are also encompassed in the technical scope of the present invention.

[3] Utilization of Vector

As described above, a MATE polypeptide can be expressed in an organism or a cell into which the MATE polynucleotide is introduced by using the vector of the present invention. Since the cell membrane is supplied as a transformant or as a part of a transformant, a naturally occurring lipid membrane containing the MATE polypeptide by using the vector of the present invention can be obtained. Furthermore, to obtain an artificial lipid membrane, a purified MATE polypeptide (may be an expression system or a cell-free system) prepared using the above-described vector can be used.

Thus, the vector of the present invention can be utilized as a tool for preparation of the lipid membrane of the present invention. That is, the present invention provides a method and a kit for preparing a lipid membrane containing a MATE polypeptide.

The method for preparing a lipid membrane containing a MATE polypeptide of the present invention is characterized by comprising the step of producing a MATE polypeptide using a vector containing a MATE polynucleotide. When a naturally occurring lipid membrane is prepared, the produced MATE polypeptide does not need to be purified. However, when an artificial lipid membrane is prepared, the produced MATE polypeptide can be used after purification. Those skilled in the art who read the present specification can easily produce a MATE polypeptide using a vector containing a MATE polynucleotide.

Furthermore, the kit for preparing a lipid membrane containing a MATE polypeptide of the present invention is characterized by being provided with a vector containing a MATE polynucleotide. When a naturally occurring lipid membrane is prepared, the above-mentioned vector is a recombinant expression vector. When an artificial lipid membrane is prepared, the above-mentioned vector may be or may not be a recombinant expression vector.

Thus, it is sufficient that the method and the kit for preparing a lipid membrane containing a MATE polypeptide of the present invention at least use a vector containing a MATE polynucleotide. That is, it should be noted that methods and kits applying known techniques other than the above-mentioned techniques are also encompassed in the technical scope of the present invention.

[4] Utilization of Lipid Membrane

The present invention further provides utilization of the above-mentioned lipid membrane. In the present specification, utilization of lipid membranes will be explained with reference to a transformant and a liposome composition as examples, but utilization of the lipid membrane of the present invention is not limited to these examples.

(a) Utilization of Transformant Expressing MATE Polypeptide

When the MATE1 polypeptide was expressed in the HEK293 cell, H$^+$-dependent transport of tetraethylammonium (TEA) and 1-methyl-4-phenylpyridinium (MPP) occurred. The substrate specificity of MATE1 was similar to that of H$^+$-dependent organic cation transporters that exist in the kidneys or the liver. Thus, MATE1 was found to be a multifunctional OC transporter that excretes organic cations (OCs) directly into the urine or the bile, which had been long searched.

As described above, a MATE polypeptide has a transporter activity in a cell membrane, more specifically, a transporter activity (transport activity) for transporting organic cations (OCs) via a cell membrane. The present invention provides a method and a kit for further screening for a substrate, i.e., a target of this transport activity.

The screening method of the present invention is characterized by comprising the step of incubating the above-mentioned transformant together with tetraethylammonium (TEA) or 1-methyl-4-phenylpyridinium (MPP). In the above-mentioned step, if the uptake amount of TEA or MPP into the above-mentioned transformant is changed in the presence or absence of a candidate substrate, that is, transport of TEA or MPP is inhibited by the existence of the candidate substrate, it can be determined that the candidate substrate is a novel substrate of the MATE polypeptide.

As demonstrated in the examples described later, cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin serve as substrates of MATE polypeptides in addition to tetraethylammonium (TEA) and 1-methyl-4-phenylpyridinium (MPP) in the screening method of the present invention. That is, these compounds are transported by MATE polypeptides.

Thus, those skilled in the art who read the present specification easily understand that one or more of the above-mentioned compounds instead of TEA or MPP may be used as criteria for determining whether transport of the compound(s) is inhibited or not in the screening method of the present invention. When used in the present invention, these compounds are preferably labeled so that they can be detected. Preferred examples of labels include, but are not limited to, radiolabel.

The screening kit of the present invention is characterized by being provided with the above-mentioned transformant. In a preferred embodiment, it is preferable that the screening kit of the present invention is further provided with tetraethylammonium (TEA) or 1-methyl-4-phenylpyridinium (MPP). In the above-mentioned step, if the uptake amount of TEA or MPP by the above-mentioned transformant is changed in the presence or absence of a candidate substrate, that is, transport of TEA or MPP is inhibited by the existence of the candidate substrate, it can be determined that the candidate substrate is a novel substrate of the MATE polypeptide. Furthermore, as described above, instead of TEA or MPP, one or more of cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin can be used as criteria for determining whether the transport is inhibited or not.

The present invention provides further uses of a transformant expressing a MATE polypeptide. In one aspect, the present invention provides a method and a kit for screening for a chemical that regulates excretion of a chemical and/or a waste. In another aspect, the present invention provides a method and a kit for testing a chemical for nephrotoxicity and/or hepatotoxicity. In yet another aspect, the present invention provides a method and a kit for measuring amounts of transport, secretion, accumulation, or excretion of many biological components (in particular, biological components with high hydrophobicity), such as absorption or excretion of monoamines, volatile organic cations, and nicotine, secretion, absorption, or excretion of melatonin, steroid hormones, sex hormones, and related formulations thereof, concentrations of plant alkaloids or phenols in a plant body, as well as a method and a kit for screening for a chemical that regulates transport, secretion, accumulation, or excretion thereof. In any case, the present invention is characterized by using a transformant expressing a MATE polypeptide and preferably utilizes a substrate of a MATE polypeptide. Furthermore, since what compound binds to a MATE polypeptide existing in a cell membrane can be investigated by using the screening kit of the present invention, an inhibitor or an activity enhancer for a MATE polypeptide can be screened for.

Since the entity of transporters is unknown, various drugs could not be tested so far. Chemicals that inhibit the transporter of the present invention may cause long-term retention thereof in the body and hence various long-term toxicities. Therefore, effects of chemicals on this transporter need to be tested beforehand when the chemicals are commercially produced.

To excrete a chemical or a toxin out of the body (urine and/or feces), these substances need to pass through many cells via many kinds of transporters. The transporter of the present invention is responsible for the final stage of such excretion.

The present invention established a cultured cell line constantly expressing a novel transporter existing at the apical site (site in contact with primitive urine) of the renal tubules in the kidneys or the micro bile duct in the liver (site at which a bile is excreted) using many unspecified organic cations as substrates. This cell line can be used with an assay system for testing transport (excretion) of various drugs, agricultural chemicals, and the like.

The method and the kit of the present invention has been explained using a transformant expressing a MATE polypeptide, but a method further comprising the step of preparing a transformant expressing a MATE polypeptide and a kit further provided with a tool for preparing a transformant expressing a MATE polypeptide also belong to the technical scope of the present invention.

(b) Utilization of Liposome Composition Containing Mate Polypeptide

As explained in detail in the examples, when a MATE1 polypeptide is expressed in the HEK293 cell, $H^+$-dependent transport of tetraethylammonium (TEA) and 1-methyl-4-phenylpyridinium (MPP) occurred. Furthermore, $H^+$-dependent transport of tetraethylammonium (TEA) was confirmed in a liposome composition containing a MATE1 polypeptide. The substrate specificity of MATE1 was similar to those of $H^+$-dependent organic cation transporters existing in the kidneys or the liver. Thus, it was revealed that MATE1 was a multifunctional OC transporter which excretes organic cations (OCs) directly into the urine or the bile, which has been searched over a long period.

As described above, a MATE polypeptide has a transporter activity in a cell membrane, more specifically, a transporter activity (transport activity) for transporting organic cations (OCs) via a cell membrane. The present invention provides a method and a kit for screening for a target substrate of such a transport activity.

The screening method of the present invention is characterized by comprising the step of incubating the above-mentioned liposome composition together with tetraethylammonium (TEA) or 1-methyl-4-phenylpyridinium (MPP). When the uptake amount of TEA or MPP into the above-mentioned liposome composition is changed in the presence or absence of a candidate substrate in the above-mentioned step, that is, transport of TEA or MPP is inhibited by the existence of the candidate substrate, it can be determined that the candidate substrate is a novel substrate of the MATE polypeptide.

As demonstrated in the examples described later, cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin serve as substrates of MATE polypeptides in addition to tetraethylammonium (TEA) and 1-methyl-4-phenylpyridinium (MPP) in the screening method of the present invention. That is, these compounds are transported by MATE polypeptides.

Thus, in the screening method of the present invention, those skilled in the art who read the present specification easily understand that one or more of the above-mentioned compounds can be used instead of TEA or MPP for criteria to determine whether transport thereof is inhibited or not. When used in the present invention, these compounds may be labeled so that they can be detected. Preferred examples of the label include, but are not limited to, radiolabel and fluorescence label.

The screening kit of the present invention is characterized by being provided with the above-mentioned liposome composition. In a preferred embodiment, it is preferable that the screening kit of the present invention is further provided with tetraethylammonium (TEA) or 1-methyl-4-phenylpyridinium (MPP). In the above-mentioned step, if the uptake amount of the above-mentioned liposome composition by TEA or MPP is changed in the presence or absence of a candidate substrate, that is, TEA or MPP transport is inhibited by the existence of the candidate substrate, it can be determined that the candidate substrate is a novel substrate of the MATE polypeptide. Furthermore, as described above, one or more of cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin can be used instead of TEA or MPP for criteria to determine whether transport thereof is inhibited or not.

The present invention further provides further uses of a liposome composition containing a MATE polypeptide. In one aspect, the present invention provides a method and a kit for screening for a chemical that regulates excretion of a chemical and/or a waste. In another aspect, the present invention provides a method and a kit for testing a chemical for nephrotoxicity and/or hepatotoxicity. In yet another aspect, the present invention provides a method and a kit for measuring transport, secretion, accumulation, and excretion of many biological components (in particular, biological components with high hydrophobicity), such as absorption or excretion of monoamines, volatile organic cations, and nicotine, secretion, absorption, or excretion of melatonin, steroid hormones, sex hormones, and related formulations thereof, and concentration of plant alkaloids or phenols in a plant body, as well as a method and a kit for screening for a chemical that regulates transport, secretion, accumulation, and excretion thereof. In any case, the present invention is characterized by using a liposome composition containing a MATE polypeptide and preferably utilizes a substrate of a MATE polypeptide. Furthermore, since what compound binds to a MATE polypeptide existing in a cell membrane can be investigated by using the screening kit of the present invention, an inhibitor or an activity enhancer for a MATE polypeptide can be screened for.

Since the entity of transporters is unknown, various chemicals could not be tested so far. Chemicals that inhibit the transporter of the present invention may cause long-term retention thereof in the body and hence various long-term toxicities. Therefore, effects of chemicals on this transporter need to be tested beforehand when the chemicals are commercially produced.

To excrete chemicals or toxins out of the body (urine and/or feces), these substances need to pass through many cells via many kinds of transporters. The transporter of the present invention is responsible for the final stage of such excretion.

The present invention established a liposome composition containing a novel transporter existing at the apical site (site in contact with primitive urine) of the renal tubules in the kidneys or the micro bile duct in the liver (site at which a bile is excreted) using many unspecified organic cations as substrates. This liposome composition can be used with an assay system for testing transport (excretion) of various drugs, agricultural chemicals, and the like.

The method and the kit of the present invention have been explained using a liposome composition containing a MATE polypeptide, but a method further comprising the step of preparing a liposome composition containing a MATE polypeptide and a kit further provided with a tool for preparing a liposome composition containing a MATE polypeptide also belong to the technical scope of the present invention.

[5] Oligonucleotides and Utilization Thereof

The present invention provides a polynucleotide consisting of the nucleotide sequence of SEQ ID NO: 1, 3, 5, 7, or 21 or a fragment of a mutant thereof, or an oligonucleotide consisting of a complementary sequence thereof.

The oligonucleotide of the present invention means a fragment of at least 12 continuous nucleotides, preferably at least 15 nucleotides, more preferably at least 20 nucleotides, yet more preferably at least 30 nucleotides, yet more preferably at least 40 nucleotides in length in the nucleotide sequence of SEQ ID NO: 1, 3, 5, 7, or 21 or a complementary sequence thereof. In one embodiment, the oligonucleotide of the present invention can be a DNA fragment based on SEQ ID NO: 1, 3, 5, 7, or 21. Since the nucleotide sequence of SEQ ID NO: 1, 3, 5, 7, or 21 is provided with reference to the present specification, those skilled in the art can easily prepare a DNA fragment based on SEQ ID NO: 1, 3, 5, 7, or 21. For example, restriction endonuclease digestion or ultrasonic shearing can be easily utilized to prepare fragments of various sizes. Alternatively, such fragments can be prepared synthetically. In another embodiment, the oligonucleotide of the present invention can be an oligonucleotide consisting of the nucleotide sequence of any one of SEQ ID NOS: 11 to 18 or a complementary sequence thereof.

The oligonucleotide of the present invention can be used to prepare the polypeptide of the present invention as a primer for polymerase chain reaction (PCR). Furthermore, the oligonucleotide of the present invention can be used for northern blot analysis or as a PCR primer to detect mRNA expression of a target gene in a specific tissue. Specifically, an organism or a tissue expressing a MATE polypeptide can be easily detected by utilizing the oligonucleotide of the present invention as a hybridization probe for detecting a polynucleotide coding for a MATE polypeptide or a primer for amplifying a polynucleotide coding for a MATE polypeptide. Furthermore, since intensity of expression of a polynucleotide coding for a MATE polypeptide can be confirmed by using the polynucleotide or the oligonucleotide of the present invention, a disease or a disorder attributable to abnormal substance transport can be diagnosed.

That is, the present invention further provides a diagnosis method and a diagnosis kit using the above-mentioned oligonucleotide. As described above, the oligonucleotide of the present invention hybridizes specifically with a polynucleotide coding for (MATE polynucleotide) a polypeptide which has the "MATE activity," that is, a transporter activity in a cell membrane (MATE polypeptide). Therefore, a disease or a disorder attributable to abnormal substance transport can be diagnosed by detecting the existence or absence of a MATE polynucleotide in each tissue of an organism by using the oligonucleotide of the present invention. Specifically, the expression level of a MATE polynucleotide in a biological sample (in particular, specimen sample of a tissue, cells or a body fluid obtained from specimen) can be obtained by reacting mRNA prepared from the biological sample collected from an organism tissue by biopsy or the like with the oligonucleotide of the present invention.

It is sufficient that the kit for diagnosing a disease attributable to abnormal substance transport involving the MATE polypeptide of the present invention is provided with at least the oligonucleotide of the present invention. This kit may be further provided with a reagent for detecting this oligonucleotide, if necessary. Examples of substances transported by MATE polypeptides include, but are not limited to, tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

In other words, an object of the present invention is to provide the oligonucleotide of the present invention and utilization thereof, but not the oligonucleotide preparation methods and the like specifically described in the present specification. Therefore, it should be noted that oligonucleotides obtained by methods other than the above-mentioned methods also belong to the scope of the present invention.

[6] Antibody and Utilization Thereof

The present invention provides an antibody specifically binding to a MATE polypeptide. In one embodiment, the antibody of the present invention is characterized by binding specifically to the hMATE1 polypeptide or the mMATE1 polypeptide. The antibody of this embodiment is preferably elicited by a peptide antigen consisting of the amino acid sequence of SEQ ID NO: 19 or a peptide antigen consisting of the amino acid sequence of SEQ ID NO: 20, but the antibody production method is not limited to these methods.

The term "antibody" used in the present specification means immunoglobulin (IgA, IgD, IgE, IgG, IgM, or Fab fragment, F(ab')$_2$ fragment, or Fc fragment thereof), and examples thereof include, but are not limited to, polyclonal antibodies, monoclonal antibodies, single chain antibodies, anti-idiotype antibodies, and humanized antibodies. The antibody of the present invention can be useful for selection of a biological material expressing a MATE polypeptide and is useful for identification of the expression site.

The term "antibody binding specifically to a MATE polypeptide" used in the present specification means a complete antibody molecule or an antibody fragment (for example, Fab or F(ab')$_2$ fragment) that can bind specifically to a MATE polypeptide. Fab, F(ab')$_2$, and other fragments of the antibody of the present invention are typically produced by cleavage by protein degradation using an enzyme such as papain (generates Fab fragment) or pepsin (generates F(ab')$_2$ fragment). Alternatively, a MATE polypeptide binding fragment can be produced by application of recombinant DNA techniques or synthetic chemistry.

Thus, it is sufficient that the antibody of the present invention has at least an antibody fragment (for example, Fab or F(ab')$_2$ fragment) that recognizes the above-mentioned peptide antigen. That is, it should be noted that immunoglobulins comprising an antibody fragment that recognizes the above-mentioned peptide antigen and Fc fragment of another antibody molecule are also encompassed in the scope of the present invention.

The present invention further provides a peptide antigen eliciting an antibody that can detect a mammal MATE polypeptide. That is, the peptide antigen of the present invention is useful in a method and a kit for producing an antibody effective for immunoassay. The term "immunoassay" used in the present specification means an assay performed utilizing an immunological binding reaction based on antigen-antibody reaction. Examples of the assay utilizing an immunological binding reaction include antibody assays such as immunohistochemistry, immunoelectron microscopy, western blot, immunosedimentation assay (immunoprecipitation assay), sandwich ELISA assay, radioactive immunoassay, and immunodiffusion assay, affinity chromatography, and so forth.

The above-mentioned peptide antigen may be chemically synthesized or isolated from a natural supply source as with MATE polypeptides, or obtained utilizing recombinant expression (for example, GST fusion protein).

Those skilled in the art who read the present specification easily understand that antibody production methods and kits comprising the step of eliciting an antibody using the above-mentioned peptide antigen are also encompassed in the scope of the present invention. In a method for producing the antibody of the present invention, a complex of the above-mentioned polypeptide and an adjuvant may be used as an antigen.

The present invention further provides a diagnosis method and a diagnosis kit using the above-mentioned antibody. As described above, the antibody of the present invention has the "MATE activity," that is, binds specifically to a polypeptide which has a transporter activity (MATE polypeptide) in a cell membrane. A disease or a disorder attributable to abnormal substance transport can be diagnosed by detecting existence or absence of a MATE polypeptide in each tissue of an organism using the antibody of the present invention. Specifically, the expression level of a antigen polypeptide binding to an antibody binding specifically to a MATE polypeptide (i.e., a MATE polypeptide) in a biological sample can be obtained by reacting a biological sample (in particular, specimen sample of a tissue, cells or a body fluid obtained from specimen) collected from an organism tissue by biopsy or the like and this antibody.

It is sufficient that the kit for diagnosing a disease attributable to abnormal substance transport involving the MATE polypeptide of the present invention is provided with at least an antibody binding specifically to a MATE polypeptide. The antibody is preferably an antibody for mouse or human MATE1 or MATE2. This kit may be further provided with a reagent for detecting this antibody, if necessary. Examples of substances transported by MATE polypeptides include, but are not limited to, tetraethylammonium (TEA), 1-methyl-4-phenylpyridinium (MPP), cimetidine, quinidine, verapamil, nicotine, corticosterone, Rhodamine 123, testosterone, melatonin, progesterone, androsterone, quercetin, Rhodamine 6G, chloroquine, quinine, pyrimethamine, chlorpromazine, berberine, cisplatin, propranolol, papaverine, and thiamin.

In other words, an object of the present invention is to provide an antibody that recognizes the MATE polypeptide of the present invention and utilization thereof, but not individual immunoglobulin types (IgA, IgD, IgE, IgG, or IgM), the chimera antibody production method, the peptide antigen production method, and so forth specifically described in the present specification. It should be noted that antibodies obtained by methods other than the above-mentioned methods also belong to the scope of the present invention.

[7] Knockout Animal

A knockout animal is a gene deficient-animal obtained by destroying a specific gene. A knockout animal (in particular, mouse) is constructed as an animal having the target destroyed gene homozygously by performing gene destruction in a totipotent embryonic stem cells (ES cells), screening for ES cells in which the target gene is destroyed, preparing a chimeric animal using these cells and a mouse embryo, and mating two or more generations of animals from the chimeric animal having reproductive cells derived from ES cells.

Knockout animal is a very effective technique for constructing a novel laboratory animal, in particular, a disease model animal.

The present invention provides a knockout animal in which the MATE gene is destroyed. The knockout animal of the present invention is preferably a mouse. Since the knockout animal preparation method is known in this field, those skilled in the art can easily prepare a MATE gene-knockout animal based on the information of the MATE gene provided by the present specification.

By using the knockout animal of the present invention, a chemical that regulates substance transport across a cell membrane or a substrate of a polypeptide which has a transporter activity in a cell membrane can be screened for. Furthermore, a chemical can be tested for nephrotoxicity and/or hepatotoxicity by using the knockout animal of the present invention. Furthermore, the knockout animal of the present invention can greatly contribute to treatment of a disease attributable to abnormal substance transport across a cell membrane as a model animal of the disease.

The present invention will be explained more specifically with reference to the following examples. However, the scope of the present invention should not be limited to these examples.

EXAMPLES

1: Materials and Methods

[1-1. Cloning of cDNA]

Cloning was performed by RT-PCR using total RNA obtained by extracting the cDNA of human MATE1 (hMATE1: accession number NP-060712) from the human brain. After reverse transcription reaction, the cDNA solution was diluted 10-fold and added to a PCR buffer containing 0.6 mM dNTPs (150 μM each dNTP), 25 pmol of the primer pair, and 1.5 units of Ampli Taq polymerase (Perkin Elmer). PCR amplification was performed as follows: denaturation at 94° C. for 30 seconds, annealing at 56° C. for 30 seconds, and elongation at 72° C. for 1 minute. The amplification product (1804 base pairs) was analyzed by agarose gel electrophoresis. The primers were prepared based on Genbank accession number AK001709 (sense primer, 5'-ggccggtacccgcgagtcacatggaagctc-3'; antisense primer, 5'-cacttctagacctgtgaattgtgtgtaagc-3'). The amplified DNA fragment was digested with restriction enzymes (KpnI and XbaI) and inserted into pBluescriptKS(+). The gene sequence of human MATE1 was compared with the human genome sequence, and it was confirmed that there was no error.

Similarly, human MATE2 (hMATE2: accession number NP-690872) was cloned using a primer pair (sense, 5'-agtcgaattccaccatggacagcctccaggacacagtgg-3'; antisense, 5' agctctcgagctagtgcctggtggctaggatcctgac-3'), mouse MATE1 (mMATE1: accession number AAH31436) using a primer pair (sense, 5'-cgccggtaccaccatggaacgcacggagga-3'; antisense, 5'-agacagtttattgctgtcctttggacggat-3'), and mouse MATE2 (mMATE2: accession number XP_354611) using a primer pair (sense, 5'-caccgaattcatggagccggccgaggaca-3'; antisense, 5'-cgtactcgagttagccacggtcattgaaa-3').

[1-2. Point Mutagenesis]

A point mutation (E273Q) was introduced into human MATE1 according to the method in Non-patent Document 12 using an oligonucleotide primer (5'-ggcccaccactgcatgcacagcatgagc-3').

[1-3. Northern Blot Analysis]

Human and mouse multitissue northern blots (MTN) were purchased from Clontech. The N terminal region (nt10-601; 592 bp) of human MATE1, the C terminal region (nt1412-1712; 301 bp) of human MATE2, the C terminal region (nt1336-1599; 264 bp) of mouse MATE1, and the C terminal region (nt1087-1648; 562 bp) of mouse MATE2, which were obtained by PCR amplification, were labeled with $^{32}$P-dCTP using a DNA labeling kit (Boehringer Mannheim) and used as probes in northern blot. Hybridization was performed using Express Hyb hybridization buffer (Clontech) at 68° C. for 1 hour, and the product was washed at 50° C.

[1-4. Preparation of Antibody]

A rabbit polyclonal antibody specific to human MATE1 or mouse MATE1 was prepared using a GST fusion protein obtained by fusing the 461st to 546th amino acids of human MATE1 or the P495th to Q532nd amino acids of mouse MATE1 with GST as an antigen.

[1-5. Western Blot]

A human tissue sample was purchased from Cosmo Bio. A membrane fraction was prepared from 1 g of mouse tissue. Each tissue was suspended in a buffer comprising 20 mM MOPS-Tris (pH 7.0), 0.3 M sucrose, 5 mM EDTA, and protease inhibitors (10 μg/ml each pepstatin A, leupeptin, antipain, and chymostatin) and then homogenized. The nuclei were removed, and then the suspension was centrifuged at 100,000×g for 1 hour. The supernatant was removed, and the precipitates were suspended in the above-mentioned buffer. A buffer containing 1% SDS and 10% β-mercaptoethanol was added, then a human membrane fraction (100 μg) and a mouse membrane fraction (200 μg) were used as samples for electrophoresis. Western blot was performed according to a usual method (refer to Non-patent Document 13).

[1-6. Immunohistological Staining]

A human paraffin tissue section was purchased from Biochain. Immunohistochemical analysis was performed according to Non-patent Document 13 using the HRP-DAB method or the indirect fluorescence antibody microscopy method. The primary antibody reaction was performed in 0.5% bovine serum albumin (BSA) using 1000-fold diluted or 1 μg/ml primary antibody at room temperature for 1 hour. The samples were analyzed using Olympus BX60 Microscope or Olympus FV300 Confocal Laser Microscope.

[1-7. Immunoelectron Microscopy]

Gold colloid silver-sensitized electron microscopy was performed according to Non-patent Document 13. Physiological saline was perfused from the heart of a mouse anesthetized with ether, and then 0.1 M sodium phosphate buffer (pH 7.4) in which 4% paraformaldehyde was dissolved was refluxed. The kidney was isolated and washed with PBS. A tissue impregnated with a PBS solution containing 30% sucrose was sectioned (6-mm thickness), placed on a silanated slide glass, and embedded in an OTC compound (Sakura FineTek). The sections were incubated in 0.1 M sodium phosphate buffer (pH 7.4) containing 0.25% saponin and 5% BSA for 30 minutes and then blocked using a blocking solution containing 0.005% saponin, 10% BSA, 10% goat serum, and 0.1% cold water fish gelatin (Sigma). Then, the sections were incubated overnight at 4 together with the rabbit anti-mouse MATE1 antibody 1000-fold diluted with the blocking solution. The sections were adequately washed with a buffer containing 0.005% saponin, then incubated in a blocking solution containing goat anti-rabbit IgG gold colloid (diameter of a gold particle, 1.4 mm) for 2 hours, washed 6 times with the buffer, and then immobilized using 1% glutaraldehyde for 10 minutes. The sections were further washed, then treated with a silver sensitization kit (HQ silver Nanoprobes) at room temperature for 5 minutes, then immobilized for 90 minutes using 0.5% osmium tetraoxide. Ultrathin sections were double-stained with uranium acetate and lead citrate and analyzed using Hitachi H-7100 Electron Microscope.

[1-8. Determination of Transport Activity]

According to Non-patent Document 14, HEK293 cells were cultured in a Dulbecco's modified Eagle medium containing 10% bovine fetus serum, penicillin, and streptomycin at 37° C. under 5% $CO_2$. The pcDNA3.1/hMATE1 plasmid obtained by subcloning the cDNA coding for human MATE1 or mouse MATE1 in an expression vector pcDNA3.1(+) (Invitrogen) was transfected into the HEK293 cells cultured for 24 hours using TransIT reagent (Mirus) (cell count: $1.5 \times 10^6$ cells/10-cm dish). Cells cultured for 2 days were recovered and suspended in an activity determination buffer (pH 8.0) comprising 125 mM sodium chloride, 4.8 mM potassium chloride, 5.6 mM D-glucose, 1.2 mM calcium chloride, 1.2 mM potassium dihydrogen phosphate, 1.2 mM magnesium sulfate, and 25 mM tricine. Cells were incubated at 37° C. for 5 minutes, 50 µM RI-labeled TEA (5 kBq/assay) (PerkinElmer Life Science, Inc.) was added, and measurement of the transport activity was initiated. 200 µl each of the reaction mixtures for activity determination was recovered at a predetermined time point and filtered through a 0.45-µm HA membrane filter (Millipore), and radioactivity remaining on the filter was determined.

[1-9. Determination of Nicotine Transport Activity]

The activity at pH 8.0 was determined using a buffer comprising 125 mM sodium chloride, 4.8 mM potassium chloride, 5.6 mM D-glucose, 1.2 mM calcium chloride, 1.2 mM potassium dihydrogen phosphate, 1.2 mM magnesium sulfate, and 25 mM tricine. The activity at pH 7.0 was further determined using a buffer comprising 125 mM sodium chloride, 4.8 mM potassium chloride, 5.6 mM D-glucose, 1.2 mM calcium chloride, 1.2 mM potassium dihydrogen phosphate, 1.2 mM magnesium sulfate, and 25 mM MOPS-NaOH.

Radioactive nicotine (100 nCi, 2 µM) was added to the above-mentioned activity determination buffer prepared in the above-mentioned 8, in which human MATE1 expression HEK293 cells ($8 \times 10^5$ cells) were suspended at a final volume of 200 µl. Cells were incubated at 37° C. for 5 minutes, and the suspension was centrifuged at 5000 rpm at 37° C. The cells and the supernatant were fractionated, and uptake of nicotine into cells was measured by determining radioactivity contained each of them with a liquid scintillation counter.

[1-10. Purification of Proton Pump Protein]

The $F_oF_1$ protein, a proton pump, was prepared according to the procedures described in Moriyama Y et al., J. Biol. Chem. 266, 22141-22146 (1991).

*Escherichia coli* DK8 harboring plasmid pBWU13 expressing a large amount of $F_oF_1$ was cultured with Tanaka medium (34 mM monopotassium phosphate, 64 mM dipotassium phosphate, 20 mM ammonium sulfate, 0.3 mM magnesium chloride, 1 µM iron sulfate, 1 µM calcium chloride, 1 µM zinc chloride, 100 µg/ml isoleucine, 100 µg/ml valine, 2 µg/ml thiamin) containing 0.5% glycerol, and then bacterial cells were recovered. All the preparations thereafter were performed at 4° C.

About 10 g of bacterial cells (DK8/pBWU13) were suspended in 40 ml of membrane preparation buffer (at 4° C. 50 mM Tris-HCl [pH 8.0], 2 mM magnesium chloride, 0.5 mM EDTA, 1 mM PMSF, 1 µg/ml leupeptin, 1 µg/ml pepstatin A, 10% [v/v] glycerol, 1 mM DTT), and cells were disrupted with a French press (1,500 kg/cm$^2$). The disrupted cell suspension was centrifuged at 17,000×g for 10 minutes, and the obtained supernatant was further centrifuged at 210,000×g for 1 hour 20 minutes. The obtained membrane vesicle precipitates were suspended in the $F_oF_1$ preparation buffer (20 mM MOPS/NaOH [pH 7.0], 1 mM magnesium sulfate, 1 mM DTT, 1 mM PMSF, 0.8% octyl glucoside) and centrifuged again. 60 mg of the membrane vesicle prepared as the precipitate was suspended in 3 ml of $F_oF_1$ preparation buffer containing 2% octyl glucoside to solubilize $F_oF_1$. The solubilized solution was centrifuged at 260,000×g for 30 minutes, and $F_oF_1$ was recovered from the supernatant fraction. The recovered $F_oF_1$ was purified by centrifugation with 10 to 30% (w/v) glycerol density gradient (330,000×g for 5 hours). The glycerol density gradient was prepared with an $F_oF_1$ preparation buffer containing 1% octyl glucoside. After density gradient centrifugation, the resultant was isolated and divided into 10 fractions from the bottom of the centrifuge tube, and the first four fractions were recovered as $F_oF_1$ and stored at −80° C.

2: Results

[2-1. Gene Structure and Expression of Human MATE1]

Mammalian analogs of the MATE family, multidrug efflux transporters in bacteria, were searched on a database. As a result, it was found that three genes coding for analogs of the MATE family exist on the human 17th chromosome, and these genes were designated as hMATE1 (accession number NP-060712), hMATE2 (accession number NP-690872), and hMATE3 (FIG. 1). The MATE3 gene was a novel gene.

Figure 2:
FIG. 2 shows alignments of the amino acid sequences of hMATE1, hMATE2, and hMATE3 and the amino acid sequence of the bacterium-derived NorM. It is shown that the E273 residue, which is important for a transport activity, is conserved in all the sequences.
Figure 4A:
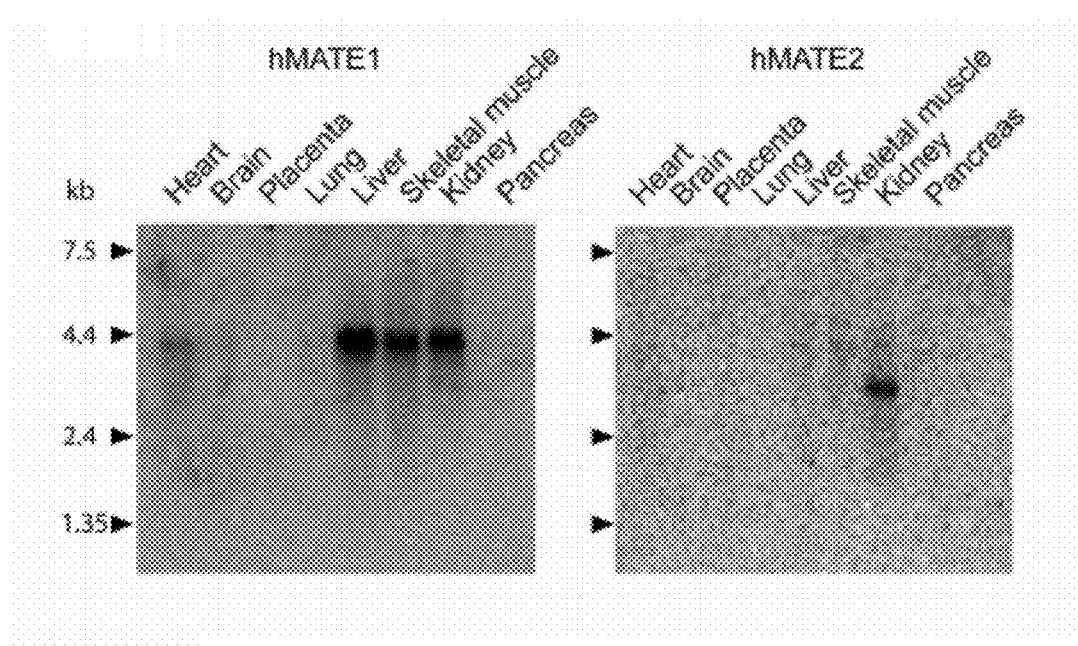
FIG. 4(*a*) shows the results of the northern blot analysis examining the expressions of the hMATE1 gene and the hMATE2 gene in humans. It is shown that the hMATE1 gene is expressed primarily in the kidneys, the liver, and the skeletal muscles, while the hMATE2 gene is expressed in the kidneys.
Figure 4B:
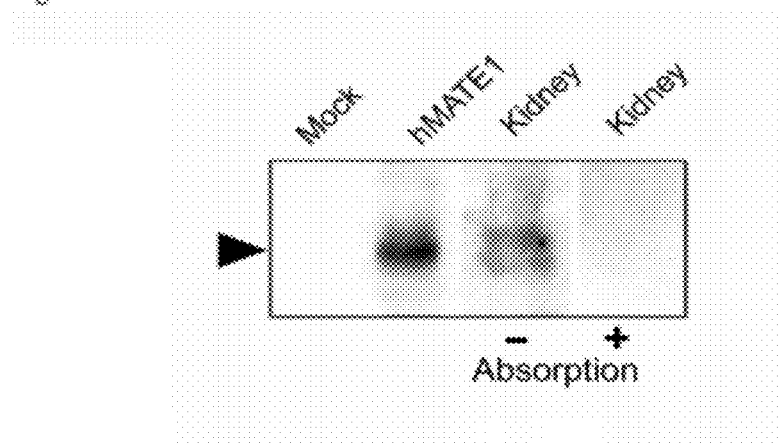
Figure 4C:
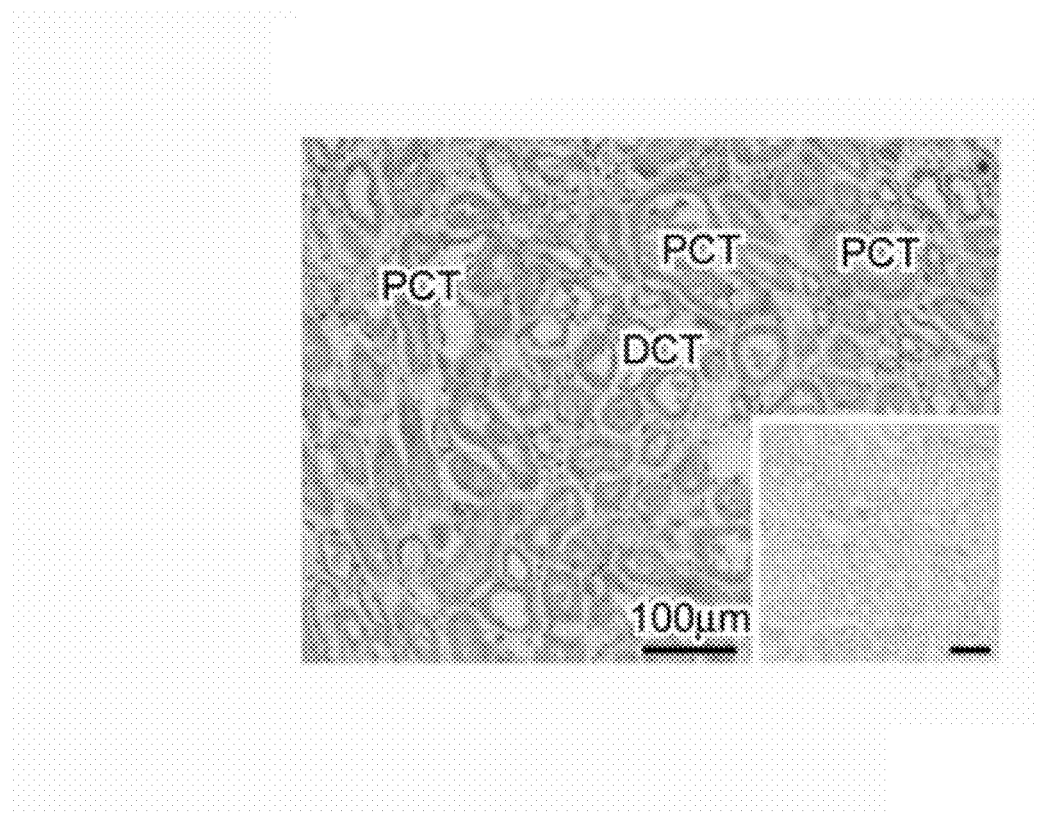
Figure 4D:
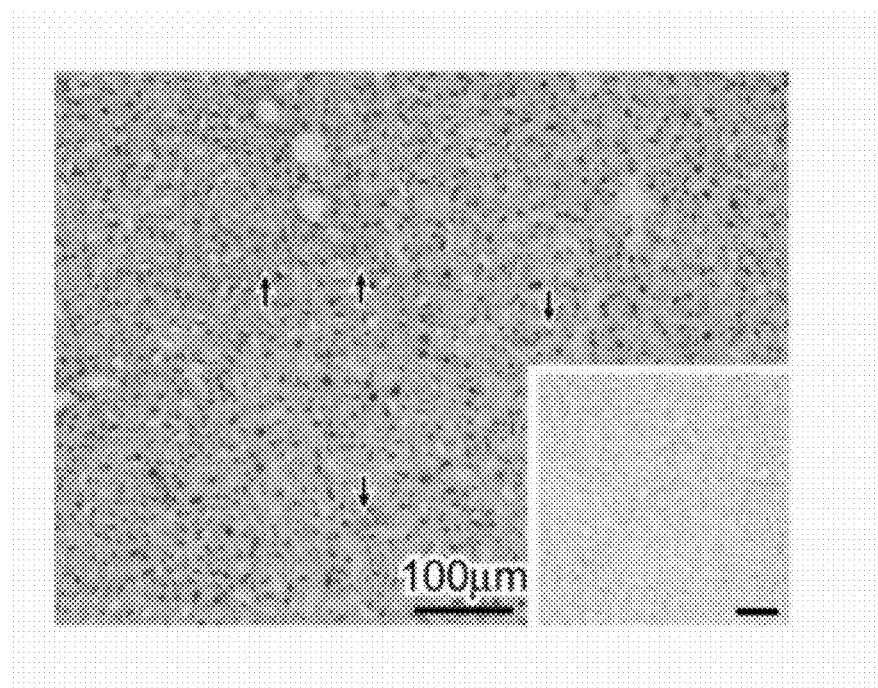

The putative amino acid sequences of the above-mentioned genes had homologies of 19.8% and 18.6% with NorM, a $Na^+$-dependent multidrug efflux transporter of *Vibrio* bacteria, which is a prototype of the MATE family (refer to Non-patent Document 15) (FIG. 2). In FIG. 2, an asterisk indicates identical amino acids, and the putative transmembrane region was surrounded in a square. E273 is glutamic acid, which is an amino acid important for the transport activity. Human MATE1 is a protein having 12 transmembrane regions according to the hydrophobicity plot (FIG. 3).

As a result of northern blot analysis of human tissues, the human MATE1 gene was found to be expressed as a 4.1-kb transcription product primarily in the kidneys, the liver, and the skeletal muscles. Furthermore, the human MATE2 gene was expressed as a 3.2-kb transcription product in the kidneys, but not expressed in other tissues (FIG. 4(*a*)).

[2-2. Localization of Human MATE1 in Kidneys and Liver]

The inventors of the present invention considered that human MATE1 is an $H^+$-dependent OC transporter at the protein level and investigated expression and localization thereof. As a result of western blot analysis using a specific antibody against the C terminal peptide of human MATE1, a band of 62 kDa, which is equal to the putative molecular weight size, was detected in human kidney membrane fractions (FIG. 4(*b*)). As a result of immunohistochemistry by horseradish peroxidase (HRP)-DAB staining, the human MATE1 protein was found to be expressed in epidermal cell sites of the proximal renal tubule and the distal renal tubule in the kidneys (FIG. 4(*c*)) and particularly in hepatocytes at the bile duct site (FIG. 4(*d*)).

[2-3. Expression and Localization of Mouse MATE1]

Figure 5:
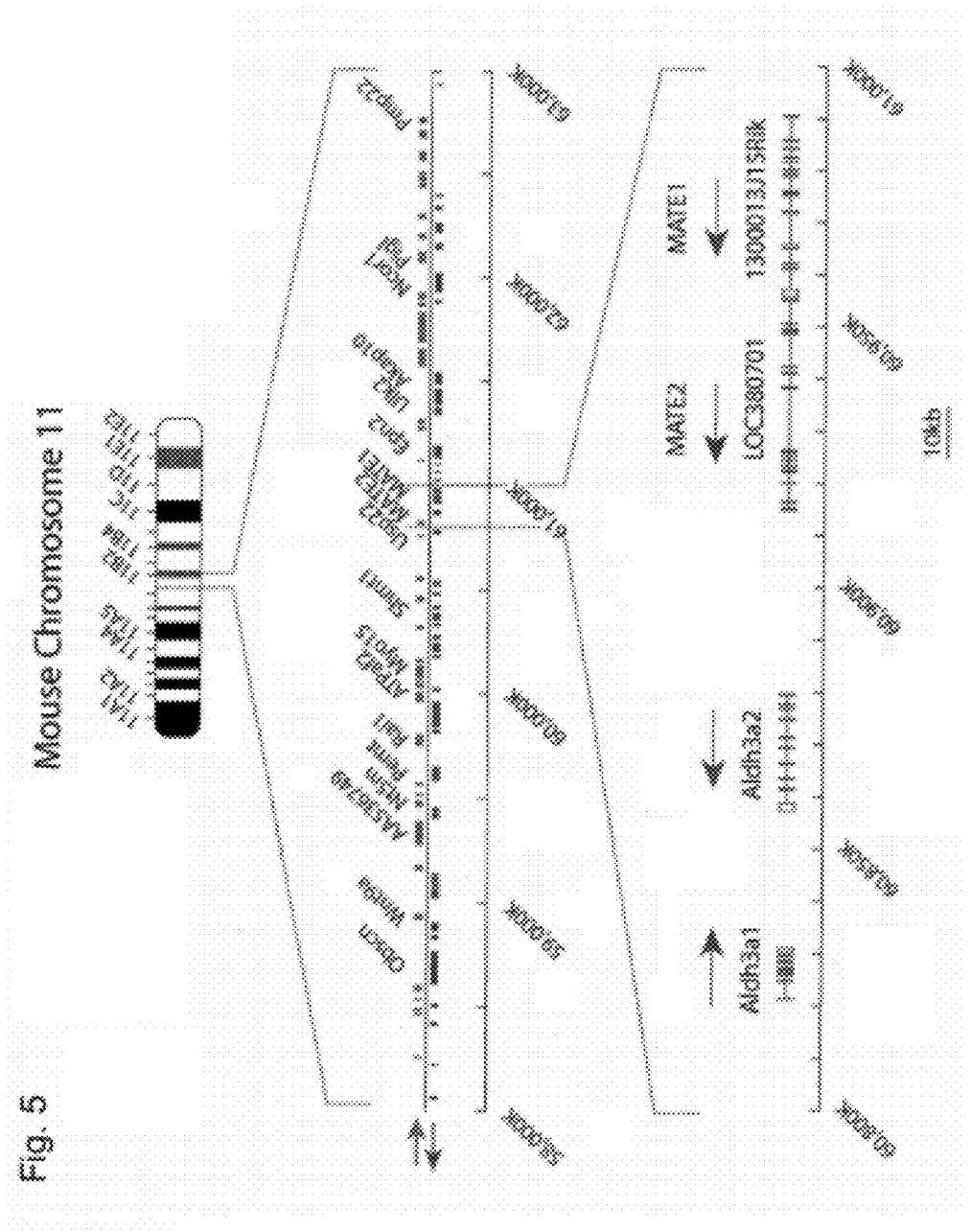
FIG. 5 shows positions and constitutions of the mMATE1 gene and the mMATE2 gene on the chromosome.
Figure 6:
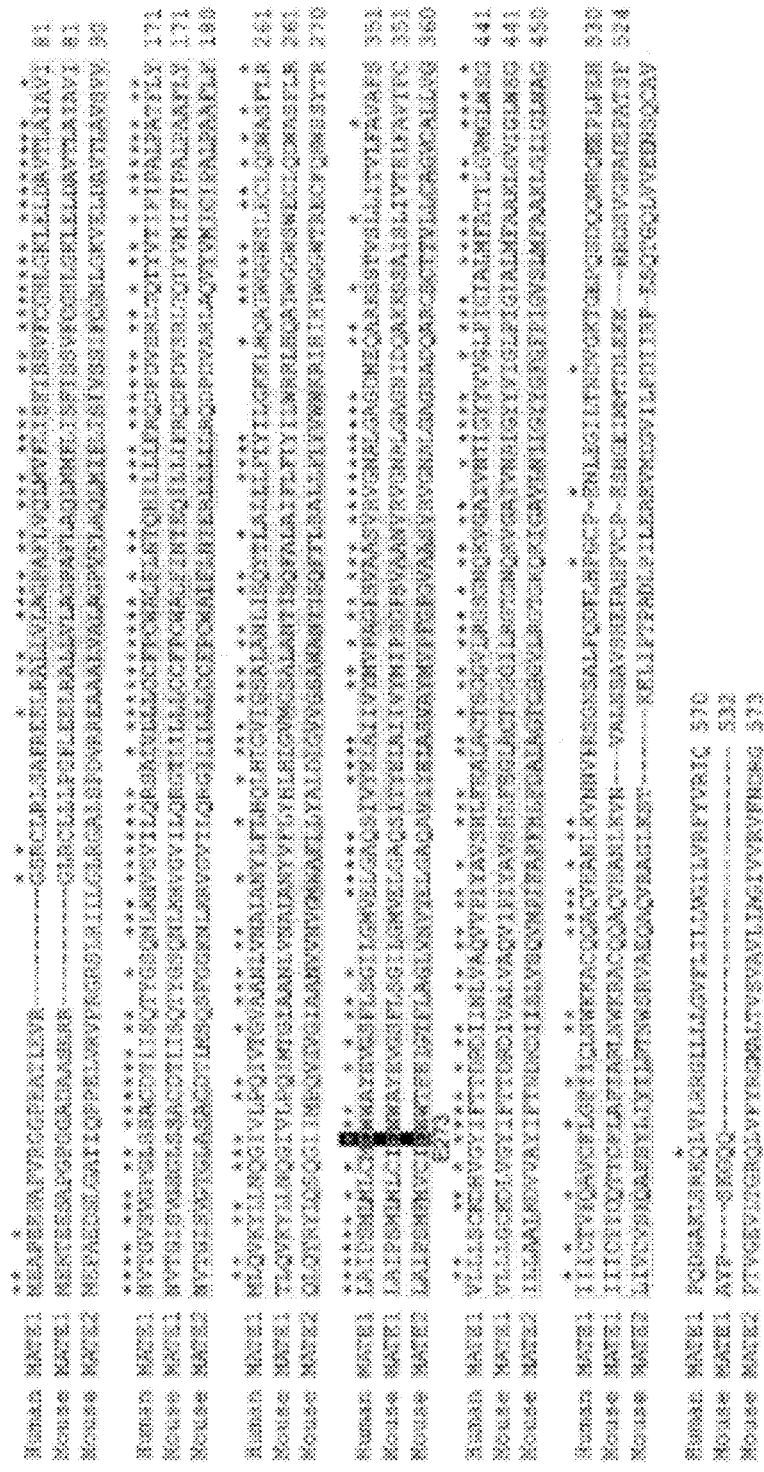
FIG. 6 shows alignments of the amino acid sequences of mMATE1 and mMATE2 and the amino acid sequence of hMATE1. In the figure, an asterisk indicates the identical amino acid. E273 is glutamic acid, an amino acid important for a transport activity.

MATE family analogs in mice were obtained, and the MATE family in mammals was further analyzed. It was found that two genes coding for the mouse MATE family analogs exist on the 11th mouse chromosome next to each other, and these genes were designated as mMATE1 (accession number AAH31436) and mMATE2 (accession number XP 354611) (FIG. 5). These putative amino acid sequences had homologies of 78.1% and 38.1%, respectively, with human MATE1 (FIG. 6).

Figure 7A:
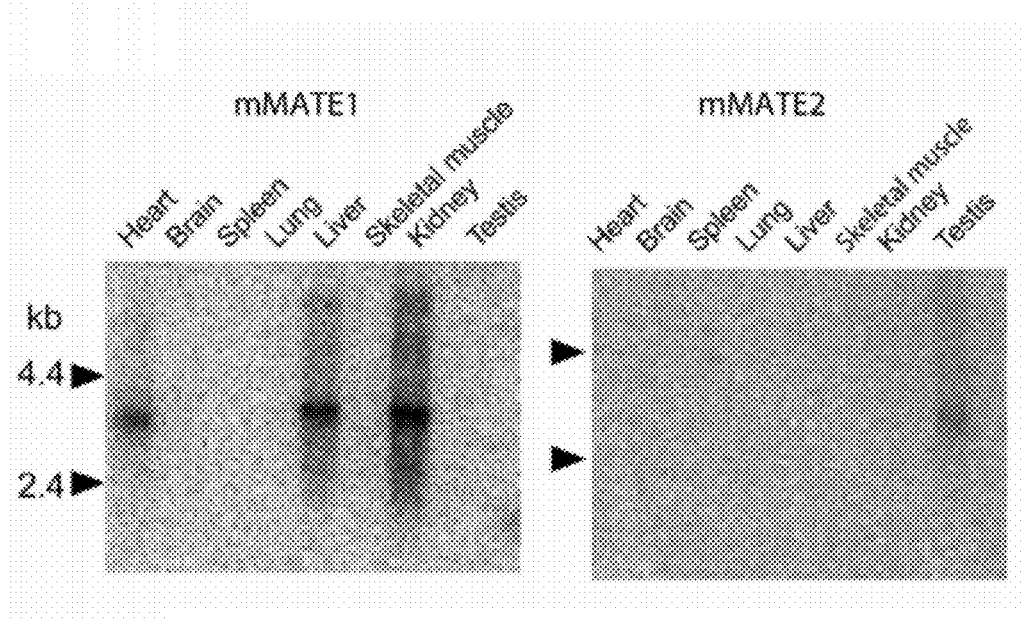
FIG. 7(*a*) shows the results of the northern blot analysis of the expressions of the mMATE1 gene and the mMATE2 gene in various organs. It was shown that the mMATE1 gene was expressed primarily in the kidneys and liver, and the mMATE2 gene was expressed in the testicle.
FIG. 7(d) shows results of the immunohistochemistry of mMATE1 in the kidneys. A mouse specimen section was stained by the HRP-DAB method. mMATE1 is expressed in the renal medulla.

As a result of the northern blot analysis of mouse tissues, it was found that the mouse MATE1 gene is expressed primarily in the kidneys, the liver, and the heart as a 3.8-kb transcription product. Furthermore, the mouse MATE2 gene was found to be expressed particularly in the testicle as a 3.3-kb transcription product (FIG. 7(a)).

Figure 7B:
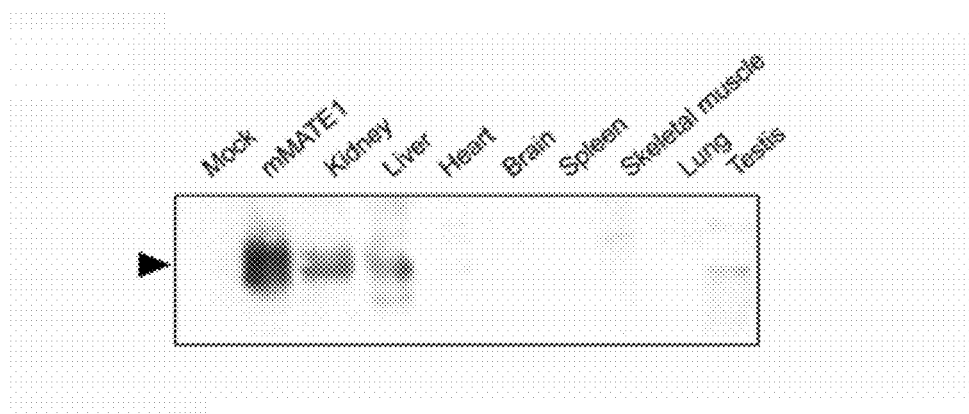
Figure 7C:
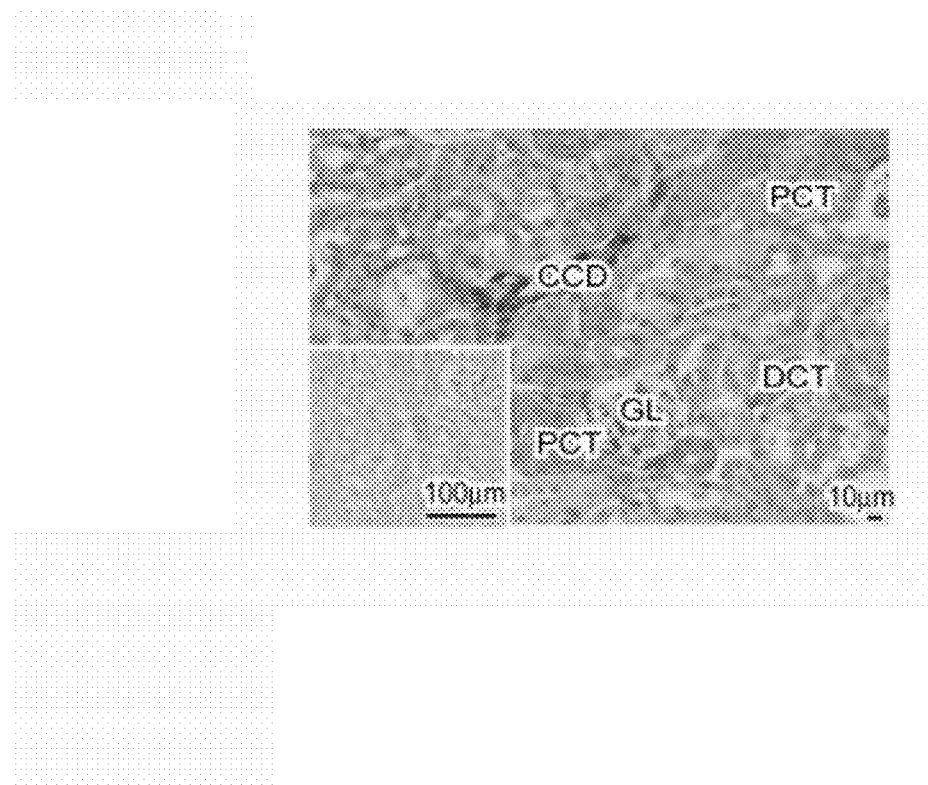
Figure 7D:
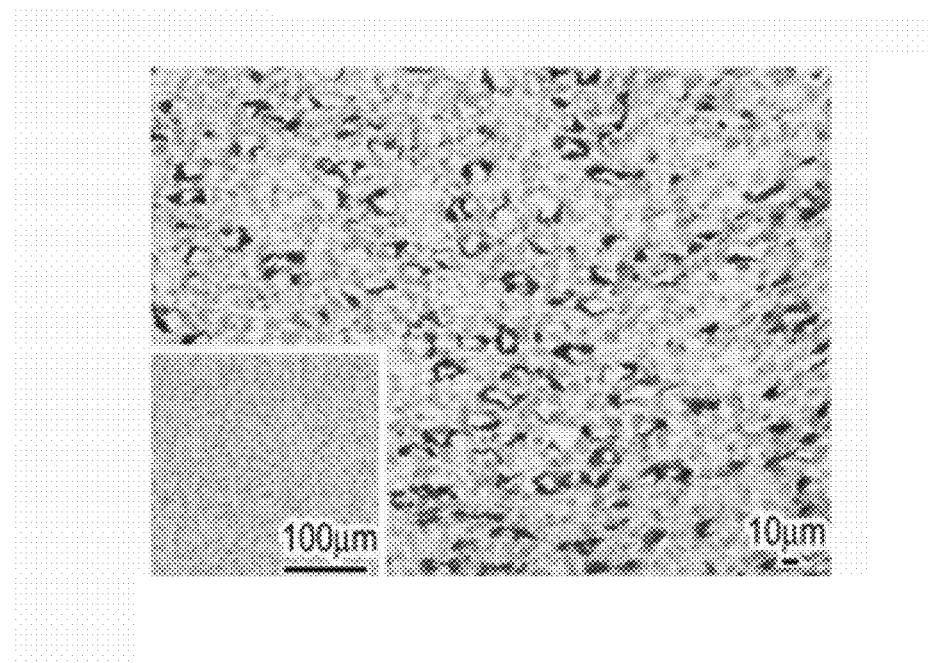

As a result of western blot analysis using a specific antibody against mouse MATE1, a band of 53 kDa, which was equal to the putative molecular weight size, was detected in the kidneys and the liver in mice (FIG. 7(b)). As a result of immunohistochemistry by horseradish peroxidase (HRP)-DAB staining, reactions of the mouse MATE1 protein were intensely detected in the collecting tubule and the proximal renal tubule of the kidney (FIG. 7(c)), particularly, around the periphery of the Henle's loop (FIG. 7(d)). Furthermore, although at a weak level, reactions of the mouse MATE1 protein were clearly detected in the distal renal tubule and the glomerulus as well (FIG. 7(c)).

Figure 8A:
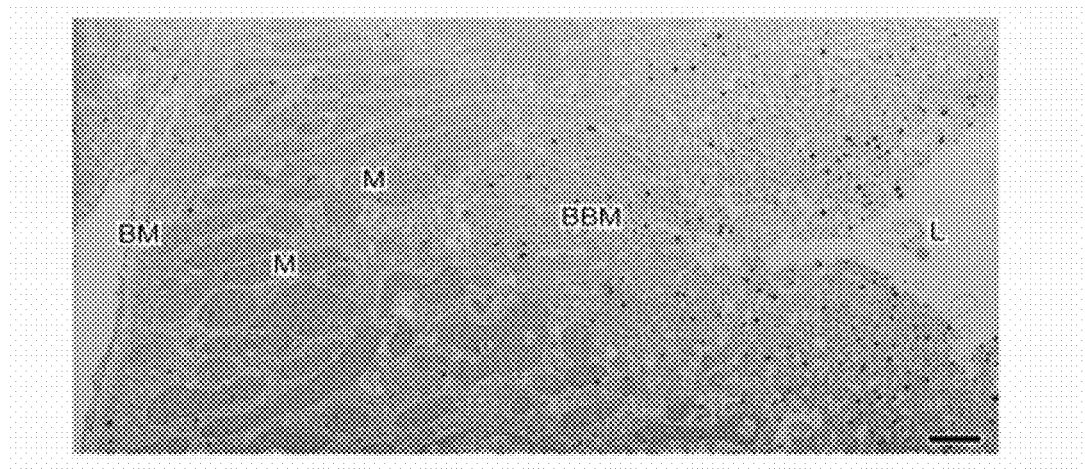
FIG. 8(a) shows an immunoelectron microscopic image of mMATE1 in the kidneys. mMATE1 exists in the epidermis (membrane portion) of the renal tubules. In the figure, BBM denotes brush border membrane, BM denotes basement membrane, M denotes mitochondrion, and L denotes lumen. The bar is 1 μm.
Figure 8B:
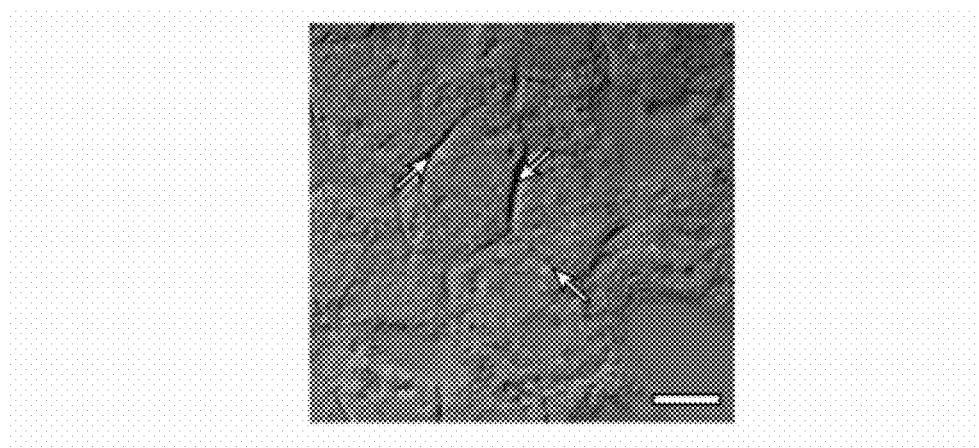
FIG. 8(b) shows an indirect immunofluorescence microscopic image of mMATE1 in the liver (capillary bile duct membrane).
Figure 8C:
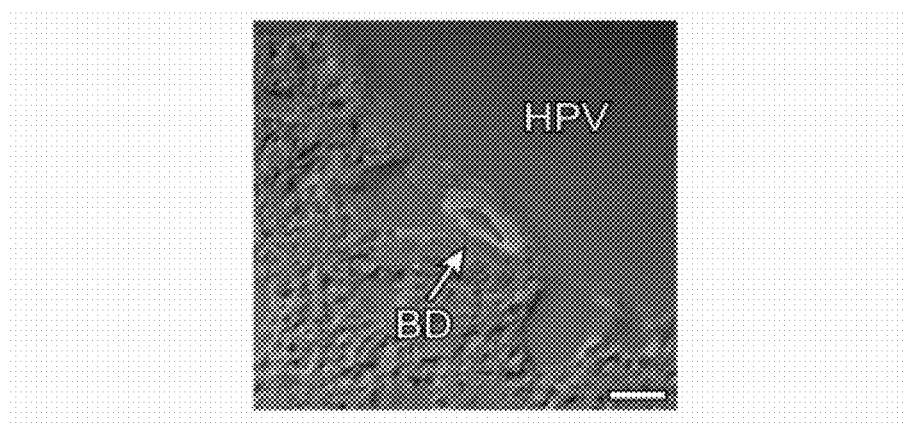
FIG. 8(c) shows the indirect immunofluorescence microscopic image of mMATE1 in the liver (epidermal side of the bile duct membrane). In the figure, BD denotes interlobular bile duct, and HPV denotes portal vein. The bar is 10 μm.

As a result of the immunoelectron microscope analysis, it was confirmed that mouse MATE1 was localized in the renal proximal tubular brush border membrane (FIG. 8(a)). In the liver, mouse MATE1 existed in the capillary bile duct and was distributed in the bile duct surface (FIG. 8(b)).

These results revealed that mammal MATE1 was expressed primarily in the kidneys (particularly in the renal proximal tubular brush border membrane) and the liver (capillary bile duct). This finding is consistent with the $H^+$/OC exchange transport activity known so far (refer to Non-patent Documents 5 to 7).

[2-4. MATE1 is Involved in OC Exchange Transport without Generating Proton-Dependent Potential Gradient]

Figure 9A:
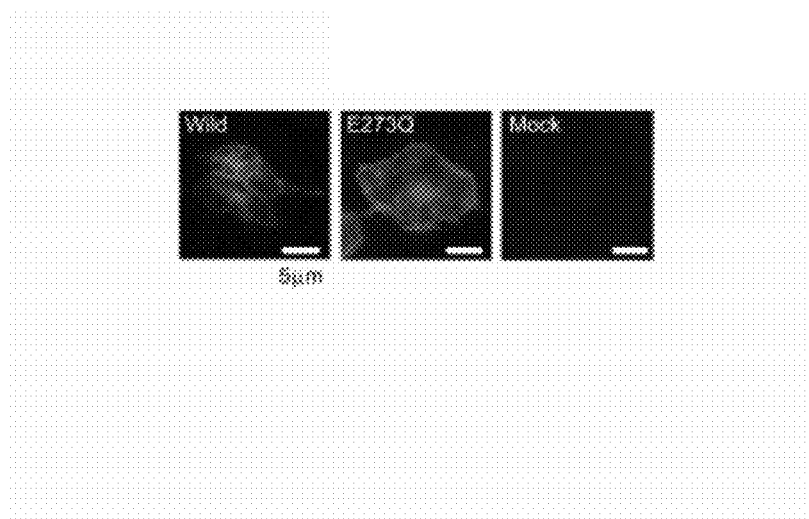
FIG. 9(a) shows immunofluorescence microscopic images of wild type (Wild) and mutant (E273Q) hMATE1 expressed in the HEK293 cells.
Figure 9B:
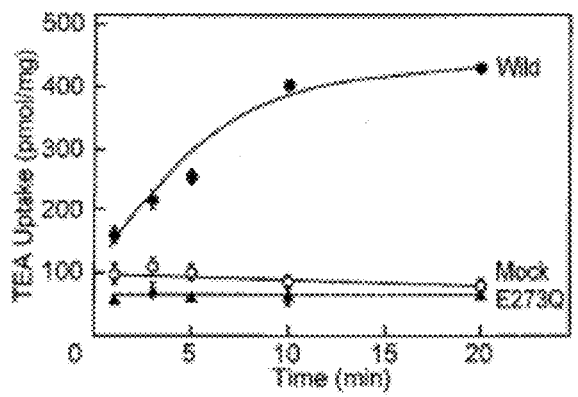
FIG. 9(b) is a graph showing the results of the observation of uptake of TEA (50 μM) into the cell shown in FIG. 9(a) at pH 8.0 over time.
Figure 9C:
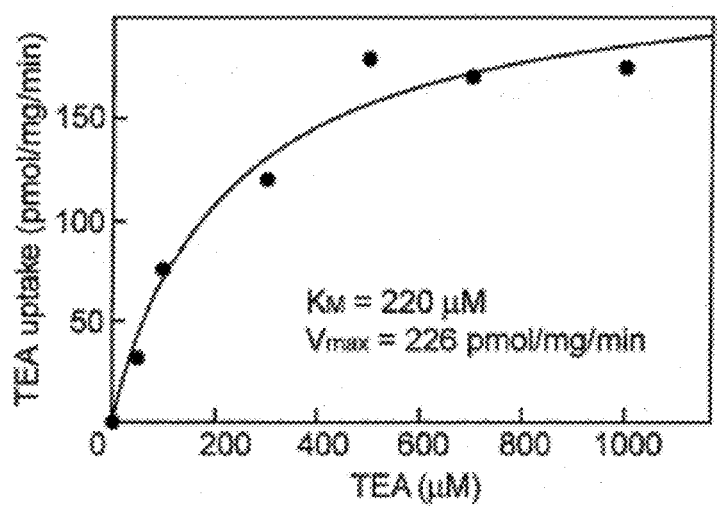
FIG. 9(c) is a graph showing the results of the observation of TEA transport at various concentrations. The value in cells transfected with only a plasmid (Mock) is deducted from the values in cells expressing the wild type hMATE1.
Figure 9D:
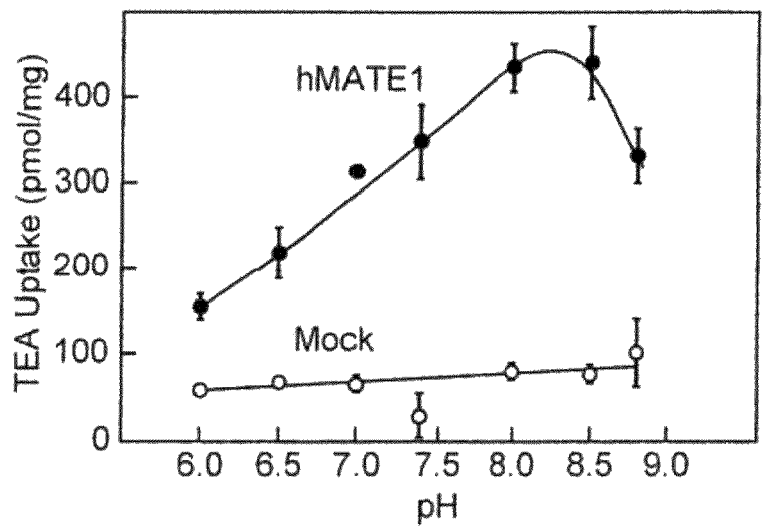
FIG. 9(d) is a graph showing the results of the observation of TEA transport at various pH.
Figure 9E:
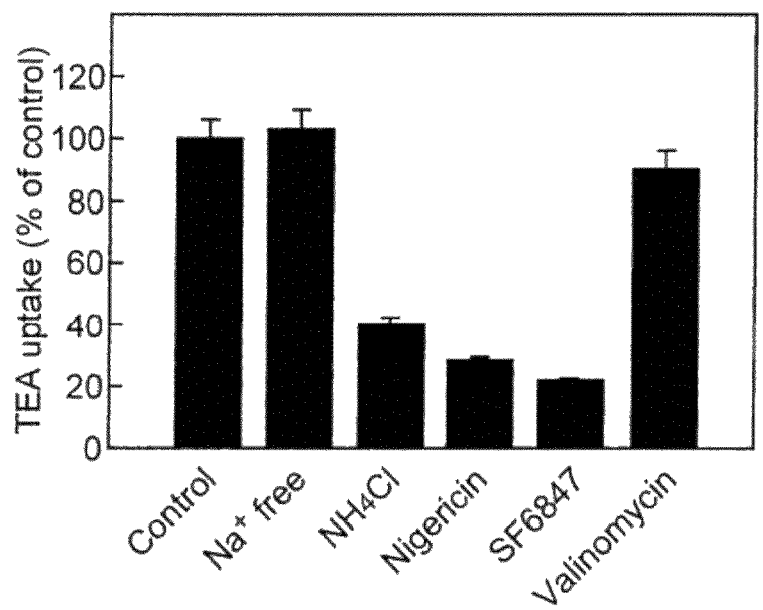
FIG. 9(e) is a graph showing effect of $Na^+$ on TEA transport.
Figure 9F:
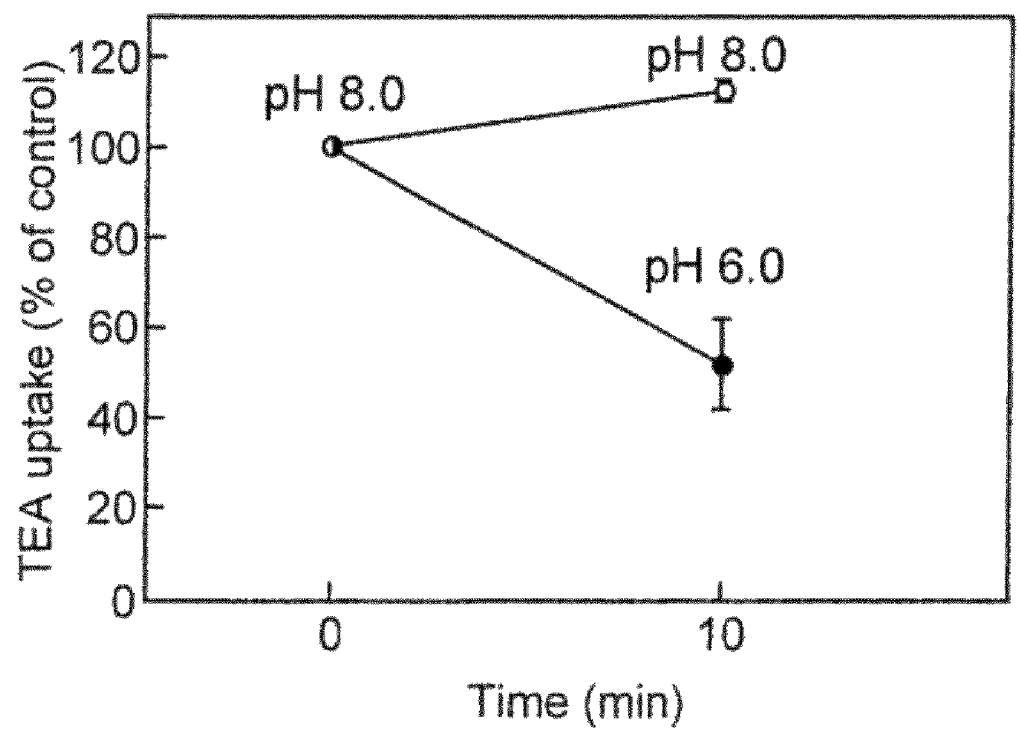
FIG. 9(f) is a graph showing the results of the observation of effect of pH on TEA excretion.

To clarify whether MATE1 has the proton-coupled OC exchange transport activity, pH-dependent OC transport via a biomembrane was analyzed in the HEK293 cell expressing human MATE1. According to this method, OC transport in the lumen can be analyzed as a classic cell uptake activity (refer to Non-patent Document 14). Cells expressing human MATE1 exhibited a time-dependent transport activity against TEA, a representative substrate of a proton-coupled OC transporter (FIGS. 9(a) and (b)). In cells expressing wild type MATE1, the transport activity was saturated, and the Km value of TEA was 220 μM (FIG. 9(c)). Furthermore, the transport activity was dependent on pH in cells expressing wild type MATE1. The activity was low at pH 6.0 and increased at higher pH, with the maximum activity at pH 8.0 to 8.5 (FIG. 9(d)). As shown in FIG. 9(e), however, this transport activity did not require sodium ions. That is, even when membrane depolarization was caused by adding 5 μM valinomycin in the presence of 65 mM potassium chloride, the TEA uptake activity was not affected. Furthermore, the TEA uptake activity was inhibited by 60% by ammonium chloride. Furthermore, when pH gradient was eliminated with nigericin (5 μM) in the presence of SF6847 (10 μM), a proton conductor, or potassium chloride, the TEA uptake activity greatly decreased (FIG. 9(e)).

These results showed that human MATE1 performs $H^+$/TEA exchange transport without generating a potential gradient.

[2-5. Inhibition of Transport Activity by Various Compounds]

Using HEK293 cells in which hMATE1 or mMATE1 was expressed, uptake of 50 μM RI-labeled tetraethylammonium (TEA) was analyzed at pH 8.0 in the presence or absence of the compounds at concentrations shown in the table (Table 1).

TABLE 1

| Compounds | (mM) | mMATE1 % ± S.D. | hMATE1 % ± S.D. |
|---|---|---|---|
| Control | | 100.0 ± 4.7 | 100.0 ± 1.9 |
| Cimetidine | 0.01 | 29.3 ± 5.2 | 44.7 ± 7.4 |
| | 0.1 | 3.1 ± 5.1 | 9.7 ± 8.7 |
| Quinidine | 0.01 | 74.7 ± 9.8 | 35.0 ± 2.1 |
| | 0.05 | 50.3 ± 5.4 | 5.1 ± 8.9 |
| | 0.1 | 26.6 ± 7.3 | 0.0 ± 4.2 |
| Procainamide | 0.1 | 65.7 ± 8.2 | 62.6 ± 0.8 |
| Verapamil | 0.1 | 23.6 ± 9.5 | 7.7 ± 7.6 |
| Guanidine | 0.5 | 96.0 ± 8.5 | 93.4 ± 7.6 |
| Carnitine | 5 | 71.2 ± 6.1 | 104.2 ± 6.4 |
| TEA | 5 | 0.0 ± 7. | 0.7 ± 1.8 |
| MPP | 0.1 | 33.1 ± 9.5 | 67.4 ± 8.4 |
| | 5 | 0.0 ± 2.1 | 0.0 ± 0.3 |
| Nicotine | 0.1 | 91.9 ± 3.1 | 63.7 ± 5.0 |
| | 5 | 36.7 ± 3.1 | 5.8 ± 4.3 |
| NMN | 1 | 115.3 ± 8.9 | 93.5 ± 1.9 |
| Choline | 5 | 62.0 ± 8.8 | 62.7 ± 4.1 |
| Serotonin | 0.1 | 86.9 ± 5.7 | 67.5 ± 8.0 |
| Corticosterone | 0.1 | 50.0 ± 2.5 | 10.0 ± 6.7 |
| Rhodamine123 | 0.01 | 0.5 ± 6.2 | 5.0 ± 6.4 |
| Quercetin | 0.1 | 47.1 ± 0.1 | 28.2 ± 3.1 |
| Lactate | 10 | 93.9 ± 3.2 | 103.8 ± 8.8 |
| Succinate | 10 | 95.1 ± 6.3 | 108.1 ± 4.2 |
| Salicylate | 10 | 92.4 ± 4.3 | 97.8 ± 4.8 |
| Probenecid | 1 | 93.7 ± 11.9 | 108.5 ± 7.9 |
| Uric acid | 1 | 109.1 ± 6.4 | 107.8 ± 2.7 |
| PAH | 5 | 94.7 ± 9.1 | 110.3 ± 2.7 |
| Testosterone | 0.001 | 67.0 ± 8.7 | 99.6 ± 4.3 |
| | 0.01 | 44.7 ± 3.0 | 64.5 ± 14.7 |
| | 0.1 | 11.5 ± 1.1 | 38.8 ± 3.2 |
| Melatonin | 0.1 | 51.4 ± 0.8 | 85.0 ± 4.0 |
| Progesterone | 0.1 | 9.3 ± 1.6 | 31.7 ± 5.6 |
| Androstenedione | 0.1 | 8.6 ± 1.7 | 36.6 ± 0.9 |
| Rhodamine 6G | 0.01 | | 6.8 ± 2.0 |
| Chloroquine | 0.01 | | 56.9 ± 5.1 |
| Chloroquine | 0.1 | | 36.9 ± 1.1 |
| Quinine | 0.01 | | 30.4 ± 2.8 |
| Pyrimethamine | 0.00001 | | 45.2 ± 3.5 |
| | 0.0001 | | 19.8 ± 1.6 |
| Chlorpromazine | 0.1 | | 12.2 ± 3.6 |
| Reserpine | 0.001 | | 86.3 ± 3.5 |
| | 0.01 | | 22.8 ± 0.9 |
| Quinacrine | 0.01 | | 41.6 ± 8.2 |
| Berberin | 0.001 | | 69.2 ± 2.1 |
| | 0.01 | | 20.4 ± 2.4 |
| | 0.1 | | 4.2 ± 0.9 |
| Rutin | 0.1 | | 71.8 ± 3.6 |
| Tocopherol | 0.1 | | 78.8 ± 9.6 |
| Thiamine | 0.1 | | 55.7 ± 7.0 |
| | 1 | | 31.1 ± 3.9 |
| Cisplatin | 1 | | 35.6 ± 6.0 |
| Paraquat | 1 | | 57.2 ± 6.8 |
| Propranolol | 0.1 | | 30.1 ± 3.9 |
| Droperidol | 0.001 | | 74.1 ± 14.7 |
| Imipramine | 0.01 | | 74.7 ± 11.9 |
| Atropine | 0.1 | | 74.6 ± 5.5 |
| Pilocarpine | 0.1 | | 96.1 ± 0.4 |
| Papaverine | 0.01 | | 26.8 ± 2.7 |
| Metformin | 0.1 | | 120.5 ± 9.4 |
| Amantadine | 0.1 | | 75.5 ± 9.8 |
| Digoxin | 0.001 | | 102.5 ± 7.3 |
| Ouabain | 0.01 | | 115.9 ± 6.6 |
| Bisphenol A | 0.01 | | 113.9 ± 2.1 |
| Catechin | 0.1 | | 104.0 ± 4.4 |
| Diethylstilbestrol | 0.1 | | 94.9 ± 7.8 |
| Thyroxine | 0.1 | | 113.0 ± 4.5 |
| Spermidine | 0.05 | | 97.0 ± 11.4 |

Values in the table represent TEA uptake activity percents taking the level with addition of no compound as 100%. NMN denotes N-methylnicotinamide. Data are shown as mean±standard deviation of three to nine experiments. *<0.05, **<0.001.

Whether these compounds can serve as transport substrates can be examined by measuring uptake of radioactive TEA into cells in the presence of the above-mentioned compounds.

As shown in Table 1, the TEA uptake activity was inhibited by cimetidine, quinidine, verapamil, 1-methyl-4-phenylpyridinium (MPP), nicotine, corticosterone, Rhodamine 123, testosterone, melatonin, progesterone, androsterone, and quercetin. That is, it was found that these compounds were transported by MATE1. In particular, the TEA uptake activity was strongly inhibited by cimetidine, quinidine, and verapamil and mildly inhibited by nicotine and choline. However, the activity was not inhibited by para-aminobutyric acid or uric acid, organic anions. When MPP known as a substrate of a proton-coupled OC transporter was used, pH-dependence similar to that in use of TEA was observed, and the Km value and Vmax were 16 µM and 170 pmol/min/mg protein, respectively. Thus, characteristics of MATE1 totally matched the proton-coupled OC transport activity in the kidneys predicted so far.

Figure 10:
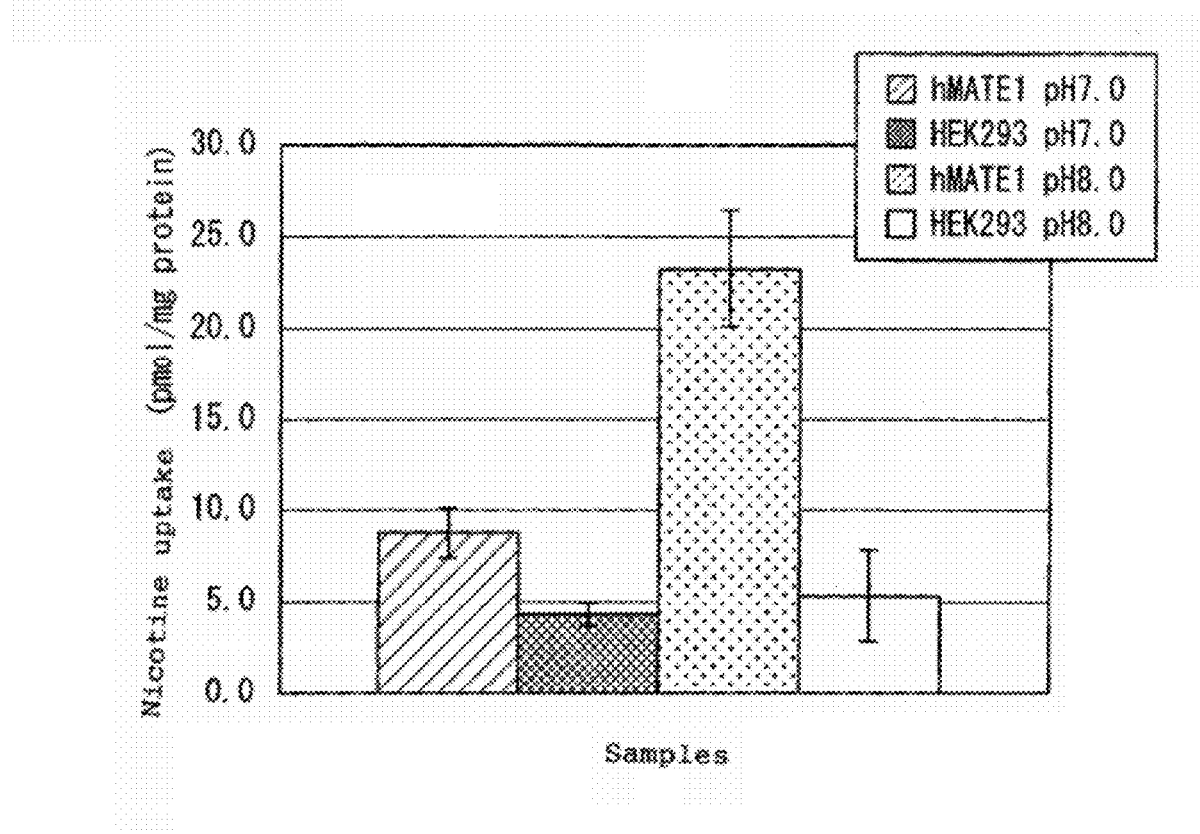
FIG. 10 is a graph showing that MATE1 functions as a nicotine transporter.

No nicotine transporter has been known at all, but it was found by the experiment using radioactive nicotine that the MATE1 protein was functioning as a nicotine transporter (FIG. 10). In the figure, data are shown as the mean±standard deviation of three experiments.

Thus, the substrate specificity of MATE1 was clarified in the experiment of competitive inhibition in TEA transport. Furthermore, the results of the experiment of competitive inhibition in TEA transport showed results similar to those of the proton-coupled OC transport activity in the kidneys.

3: Construction of Assay System Using Liposome Composition

[3-1. Preparation of Baculovirus for hMATE1 Expression]

The hMATE1 cDNA with four base pairs, CACC, added at the 5' end thereof was mixed with the TOPO vector, and the mixture was introduced into competent cells (DH5a) by the heat shock method. The plasmid pENTER-hMATE1 in which hMATE1 was incorporated was selected using kanamycin and recovered with QIAprep Spin Miniprep Kit (QIAGEN). The hMATE1 cDNA in this plasmid was cloned into the expression vector pDEST10 (INVITROGEN) using LR recombinase (INVITROGEN) for recombination. The obtained plasmid was selected on an ampicillin medium and recovered with QIAprep Spin Miniprep Kit (QIAGEN). DH10Bac (INVITROGEN) transformed using this plasmid was selected on a medium containing kanamycin, gentamicin, tetracycline, IPTG (isopropylthiogalactoside), and X-gal (5-bromo-4-chloro-3-indolyl-β-D-galactoside). Since the DH10Bac cell has the genomic DNA of baculovirus, cDNA introduced into pDEST10 is automatically cloned onto the virus genome by a transposon. As a result, colonies in which the galactosidase gene on the virus genome is destroyed and purified have a white color. Bacmid (recombinant virus genomic DNA) was recovered from white colonies on this medium by the miniprep method according to the following procedures.

The transformed DH10Bac was suspended in 0.3 ml of solution I (25 mM Tris-HCl [pH 8.0], 50 mM glucose, 10 mM ethylenediaminetetraacetic acid), and an equal volume of solution II (0.2 N NaOH, 1% sodium dodecylsulfate) was added to this suspension. After allowed to stand for 5 minutes, 0.3 ml of solution III (3 M potassium acetic acid [pH 5.2]) was added to this suspension. This suspension was centrifuged at 18,000×g for 10 minutes, and 0.8 ml of isopropyl was added to the obtained supernatant. This solution was allowed to stand on ice for 5 minutes and further centrifuged for 15 minutes. The obtained precipitates were washed twice with ice-cold 70% ethanol and dried. The dried precipitates were suspended in 40 µl of TE buffer (Tris-HCl [pH 8.0], 1 mM ethylenediaminetetraacetic acid) to obtain a recombinant bacmid solution.

Recombinant baculovirus was prepared according to the following procedures. About 3 µl of the prepared bacmid was introduced into sf9 insect cells (INVITROGEN) using Cellfectin Reagent (INVITROGEN). The sf9 cells into which the bacmid was introduced were cultured in TNM-FH medium (GIBCO) containing 10% bovine fetus serum, 100 µg/ml penicillin, 100 µg/ml streptomycin, and 0.25 µg/ml fungizone. These cells were cultured at 27° C. for 4 to 7 days, the culture supernatant was recovered, and recombinant baculovirus was obtained from the culture supernatant. The sf9 cells were infected with the obtained recombinant baculovirus again, and these infected cells were cultured in a 70 to 75-cm² flask for 4 to 7 days, the culture supernatant was recovered, and virus was obtained from the culture supernatant at a high concentration.

[3-2. Purification of hMATE1 Polypeptide]

Figure 11:
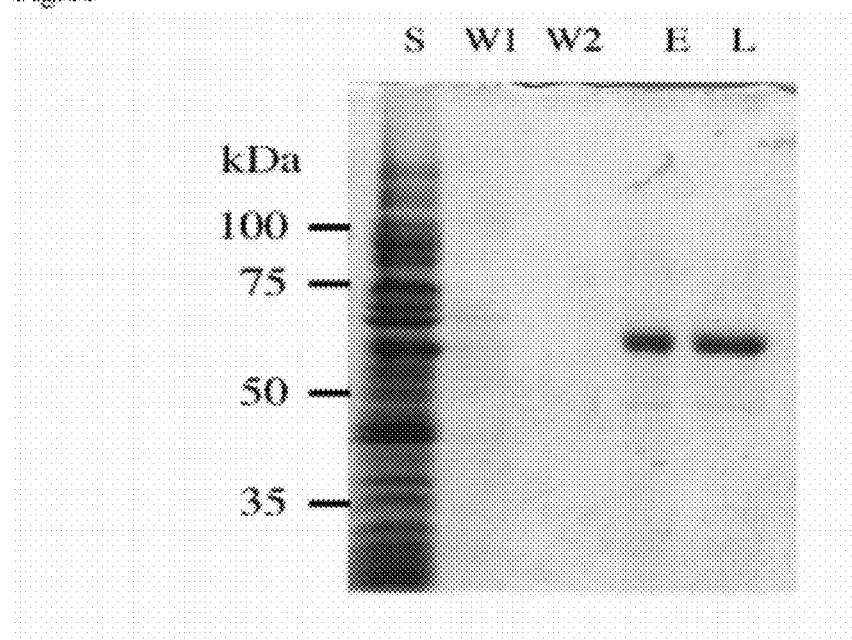
FIG. 11 shows the results of CBB-stained gel after electrophoresis of the sample at each purification step of hMATE1 purified using a baculovirus system.

Hi-Five cells (Invitrogen) were cultured in 21 dishes each containing 1×10⁷ cells and infected with the hMATE1 expressing virus at MOI=1. The infection cells were incubated at 27° C. for 48 hours and recovered. The recovered cells were suspended in 10 ml of 20 mM Tris-Cl (pH 8.0) containing 100 mM sodium acetate, 10% glycerol, 10 µg/ml leupeptin, and 10 µg/ml pepstatin A. This suspension was centrifuged and resuspended in 10 ml of the same buffer. The same procedure was repeated (washed twice). Then, cells suspended in 10 ml of the same buffer were disrupted with an ultrasonic generator (TOMY UD200). Undisrupted cells were centrifuged at 2000 rpm for 8 minutes, and the obtained supernatant was further centrifuged at 40,000 rpm for 1 hour (Beckman L-60, 60T1 rotor). The obtained precipitates were suspended in 3 ml of 20 mM MOPS-Tris (pH 7.0) containing 2% octyl glycoside, 10% glycerol, 10 µg/ml leupeptin, and 10 µg/ml pepstatin A, and this suspension was allowed to stand on ice for 30 minutes. Subsequently, the suspension was centrifuged with TL-100 Ultracentrifuge at 70,000 rpm for 30 minutes, and a solubilized MATE1 crude sample was obtained as a supernatant. Ni-NTA resin (QIAGEN) was added to this crude sample and incubated at 4° C. for 4 hours. The resin was washed with 20 ml of 20 mM MOPS-Tris (pH 7.0) containing 1% octyl glycoside, 10% glycerol, 10 µg/ml leupeptin, and 10 µg/ml pepstatin A, and then incubated in 3 ml of 20 mM MOPS-Tris (pH 7.0) containing 1% octyl glycoside, 10% glycerol, 10 µg/ml leupeptin, and 10 µg/ml pepstatin A to obtain 1.3 mg of purified hMATE1 polypeptide (FIG. 11).

A part of a product from each step of the hMATE1 purification stage (S represents 100 µg of solubilized insect cell membrane fraction; W1 and W2 represent 80 µl of supernatant after each wash; E represents 20 µg of purified hMATE protein; L represents 20 µg of hMATE protein reconstituted into a liposome) was subjected to SDS gel electrophoresis, and FIG. 11 shows the results of this CBB-stained gel. FIG. 11 shows that the target hMATE polypeptide was purified as virtually one single protein band.

[3-3. Production of Liposome Composition]

Soybean phospholipid (Sigma type IIS) was suspended in 10 mM MOPS-Tris (pH 7.0) and 0.5 mM DTT (10 mg/ml). This suspension was ultrasonicated with a bath-type sonicator, and a uniform solution was dispensed and stored at −80° C.

A part of the stored solution was thawed, and 1 mg of purified hMATE1 (800 µl) was added to 150 µl of this solution and mixed vigorously. These mixtures were rapidly frozen at −80° C., maintained for 10 minutes, then melted in hands, and then rapidly mixed with 20 ml of ice-cooled 20 mM MOPS-Tris (pH 7.0) containing 0.1 M potassium acetate, 5 mM magnesium acetate, and 0.5 mM DTT. This mixture was centrifuged at 45,000 rpm for 1 hour, and a reconstituted liposome was obtained as a precipitate. This reconstituted liposome was suspended in 500 µl of ice-cooled 20 mM MOPS-Tris (pH 7.0) containing 0.1 M potassium acetate, 5 mM magnesium acetate, and 0.5 mM DTT and subjected to the transport experiment.

[3-4. Determination of Transport Activity of Mate Polypeptide]

40 µl of the above-mentioned reconstituted liposome (liposome containing a MATE polypeptide) (corresponding to about 12 µg of protein) was dispensed, and measurement was initiated by further adding 540 µl of buffer (20 mM Tricine-NaOH [pH 8.0], 0.1 M potassium acetate, 5 mM magnesium acetate) containing 1 mM $^{14}$C-TEA (0.5 µCi).

Figure 12:
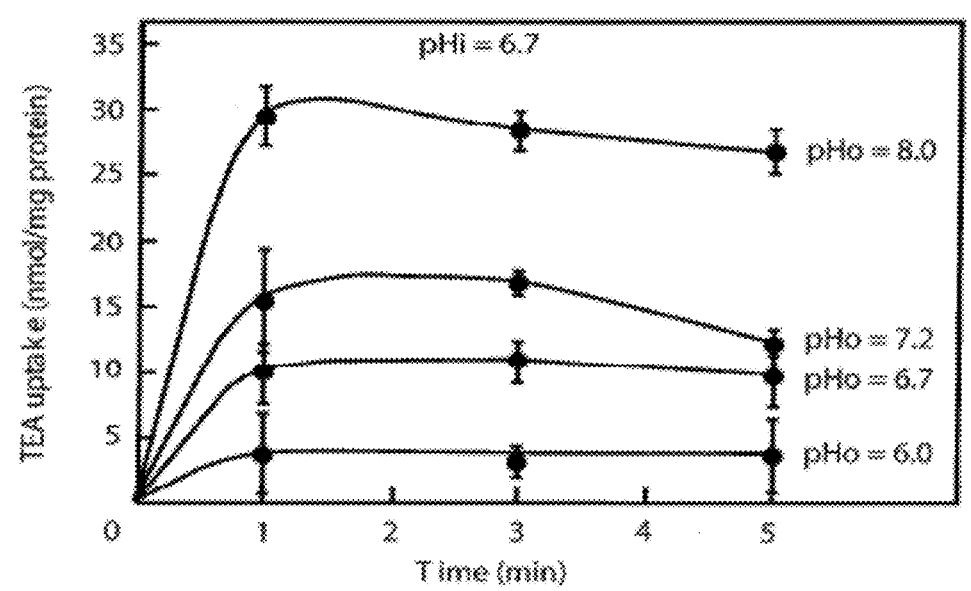
FIG. 12 shows changes over time in TEA transport determined using a liposome containing a MATE polypeptide.

After a certain time period passed, 150 µl of the reaction mixture was collected, applied to 1 ml of Terumo syringe filled with Sephadex G50, and immediately centrifuged at 2000 rpm for 1 minute. A predetermined volume of a solution eluted from the syringe (containing liposomes) was collected, and radioactivity was measured with a liquid scintillation counter (FIG. 12). The extracellular fluid was trapped in a syringe.

FIG. 12 shows changes in transport over time. The magnitude of pH gradient across the liposome membrane can be changed by changing pH of the extracellular fluid. As shown in FIG. 12, pH-dependent uptake of TEA was observed. When no MATE polypeptide, a transporter, existed, almost no radioactivity was detected (background level).

4: MATE1 Functioning as OC Transporter in Final Stage of Excretion

Figure 13:
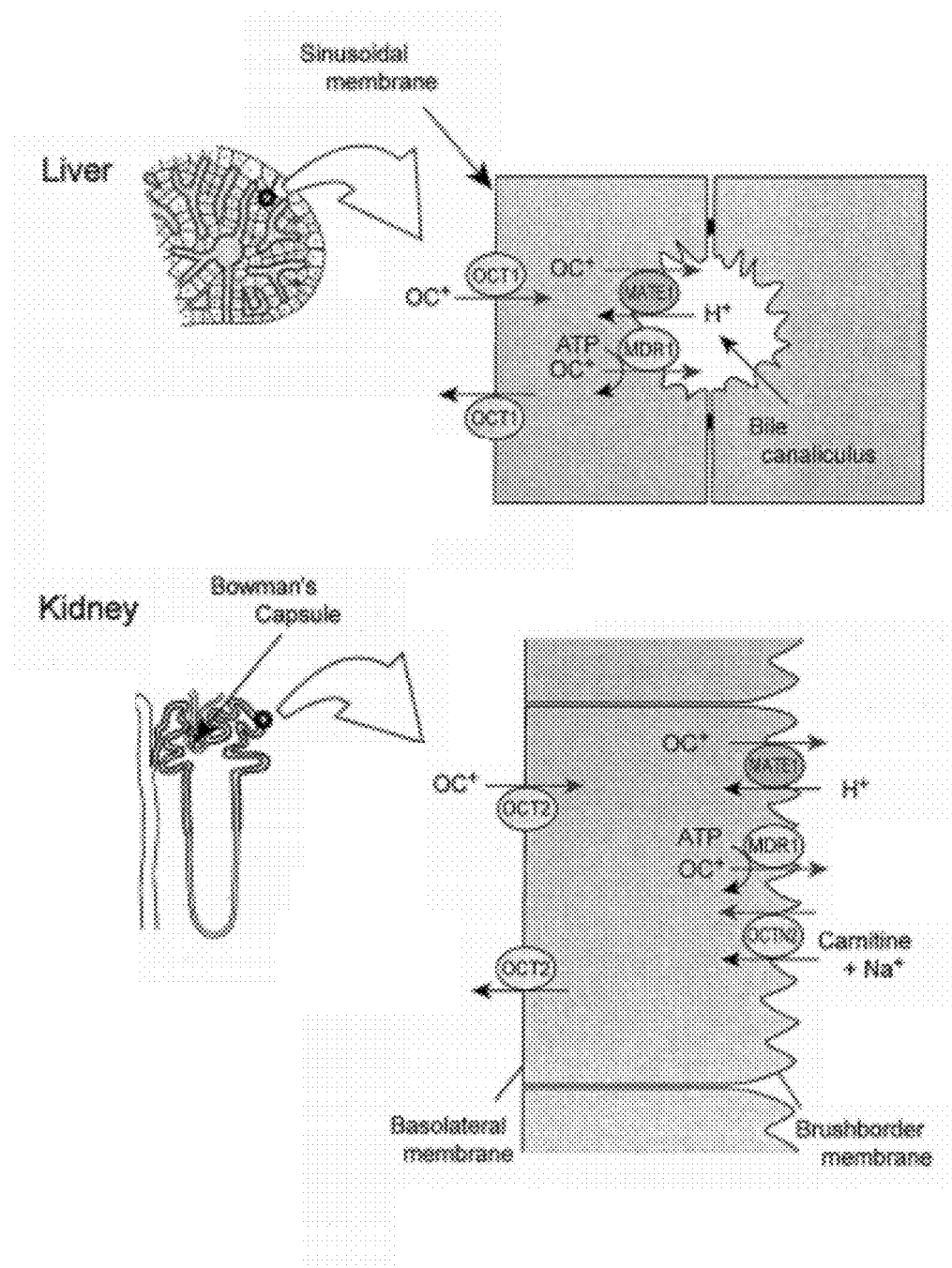
FIG. 13 is a scheme showing that MATE1 is a multidrug transporting OC transporter responsible for the final stage of OC excretion. In the liver, hepatocytes take up OCs via OCT1 and OCT2, organic cation transporters, in the sinusoidal membrane and excrete them in the bile via MATE1 and MDR1. In the kidneys, OCs are taken up primarily by renal tubule cells via OCT2 and excreted via MATE1, MDR1, and OCTN2.

Based on the above results, it can be said that MATE1 is a proton-coupled OC transporter responsible for the final stage of OC excretion in the kidneys and/or the liver which has been searched for a long time so far (FIG. 13). Based on the above-mentioned results, the whole picture of the mechanism of a transporter that excretes OCs having toxicity from an organism can be clarified.

OCs are taken up by an organic cation transporter (OCT1) in the liver or OCT2 in the renal tubules in the kidneys, and it was found that OCs taken up were excreted from cells by a concerted reaction of MATE1 with a P-glycoprotein. It was also found that MATE1 can use various metabolites as substrates from the competitive inhibition experiment.

Figure 14:
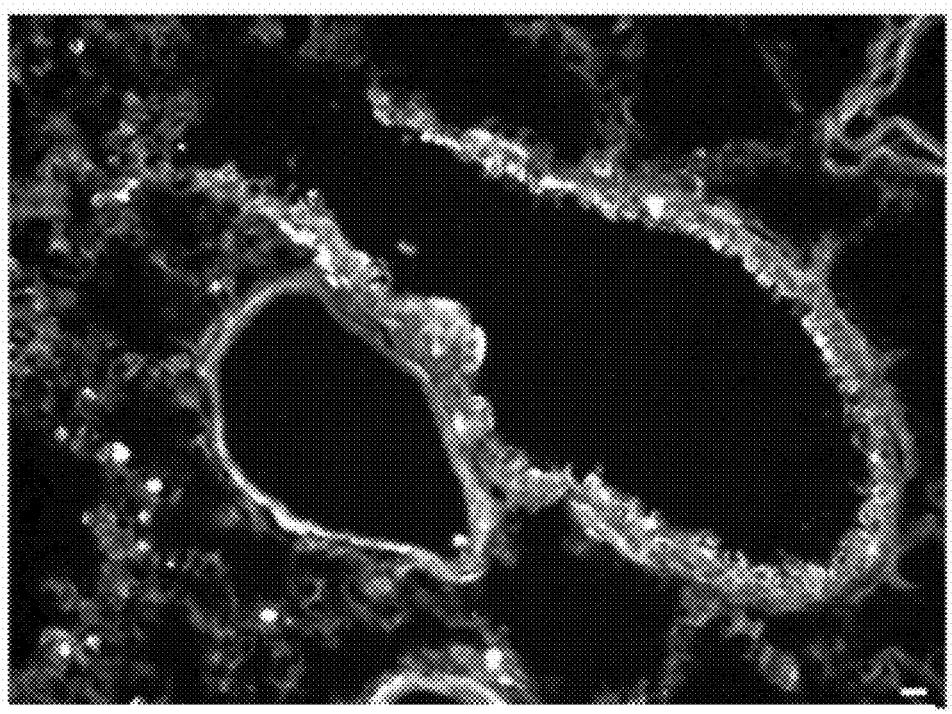
FIG. 14 shows the result of fluorescence staining of mMATE1 in the mouse alveolar epithelial cell.
Figure 15:
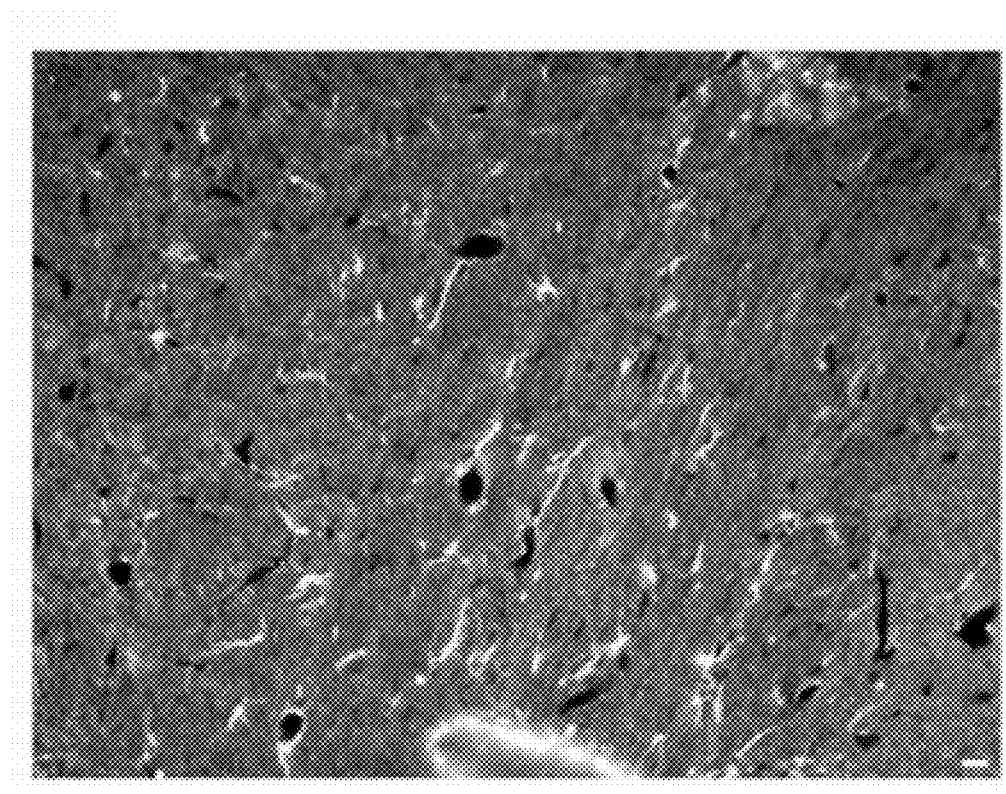
FIG. 15 shows the result of fluorescence staining of mMATE1 in the cerebral capillary blood vessel. In the figure, the bar is 10 μm.
Figure 16:
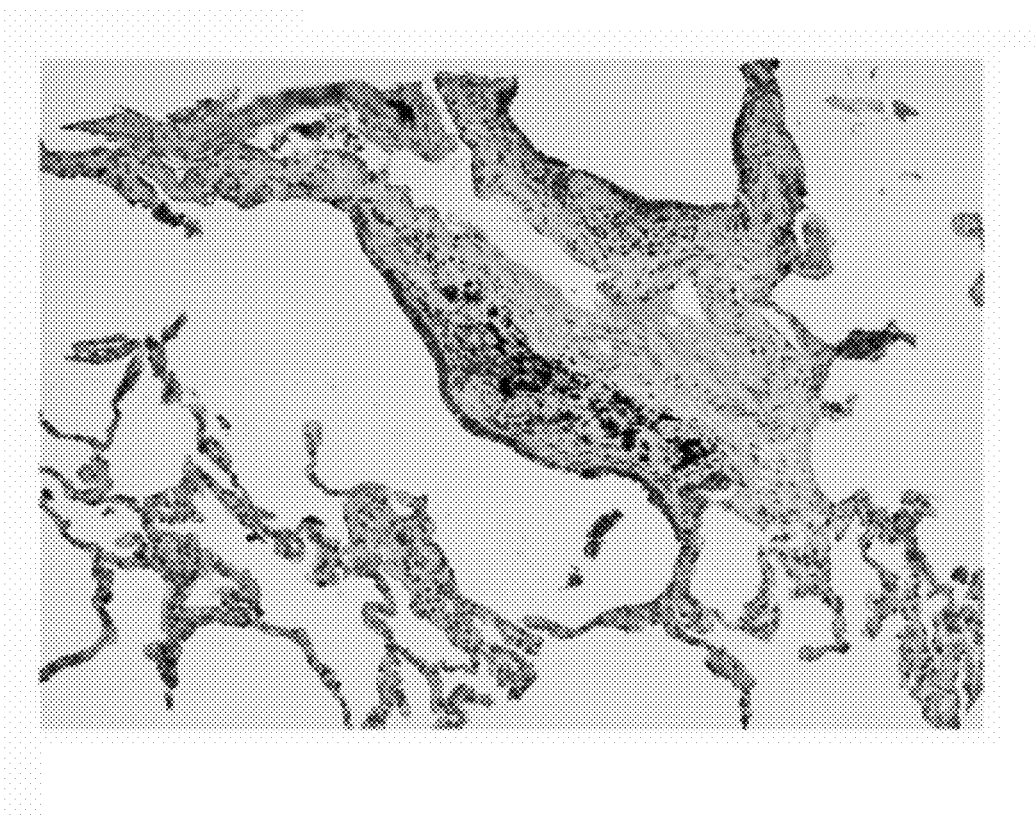
FIG. 16 shows the results of staining of hMATE1 in human alveolar epithelial cells by the HRP method. In the figure, the bar is 10 μm.

Furthermore, no nicotine transporter has been known among animals, plants, and bacteria, and the present invention revealed for the first time that MATE1 is responsible for the function thereof. Furthermore, since no transporter of melatonin or hormones has been known so far either, it can be said that MATE1 is a clinically very important protein. In fact, MATE polypeptides are expressed in a plasma membrane (apical side) of a mouse alveolar epithelial cell or in the cerebrovascular system (FIGS. 14 and 15). Furthermore, it has been confirmed that hMATE1 is expressed in human alveolar epithelial cells (FIG. 16).

Figure 17:
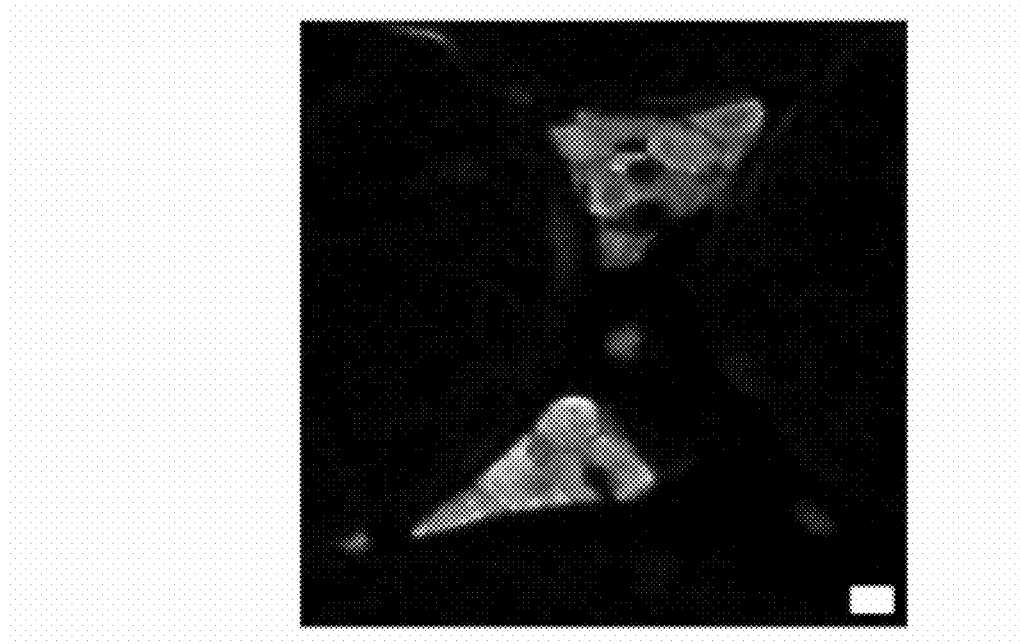
FIG. 17 shows localization of mMATE1 in the skin. It is shown that mMATE1 exists in the sebaceous gland. In the figure, the bar is 10 μm.
Figure 18:
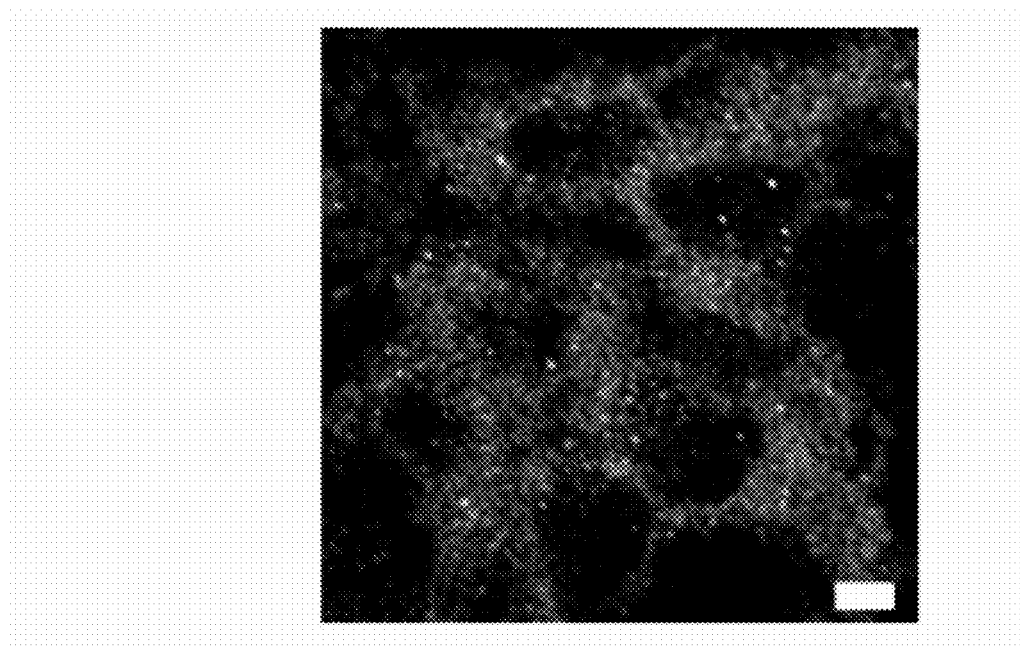
FIG. 18 shows localization of mMATE1 in the pineal body. It is shown that mMATE1 exists in the pinealocyte. In the figure, the bar is 10 μm.

The MATE polypeptide was found to have functions other than excretion of wastes in various tissues such as the skin and the pineal body. In the skin, MATE1 is expressed in the perspiratory gland and the sebaceous gland and is involved in percutaneous absorption of chemicals, excretion of substances involved in body odor, and the like (FIG. 17). It was found that MATE1 was also expressed in the pineal body, which controls circadian rhythm, through melatonin secretion (FIG. 18). This indirectly shows that MATE1 uses melatonin as a transport substrate and supports the results shown in Table 1. Therefore, MATE1 is considered to be a melatonin transporter in the pineal body cells. Furthermore, since human MATE1 and mouse MATE1 have a very high homology, it is inferred that MATE1 plays similar roles in humans.

Figure 19:
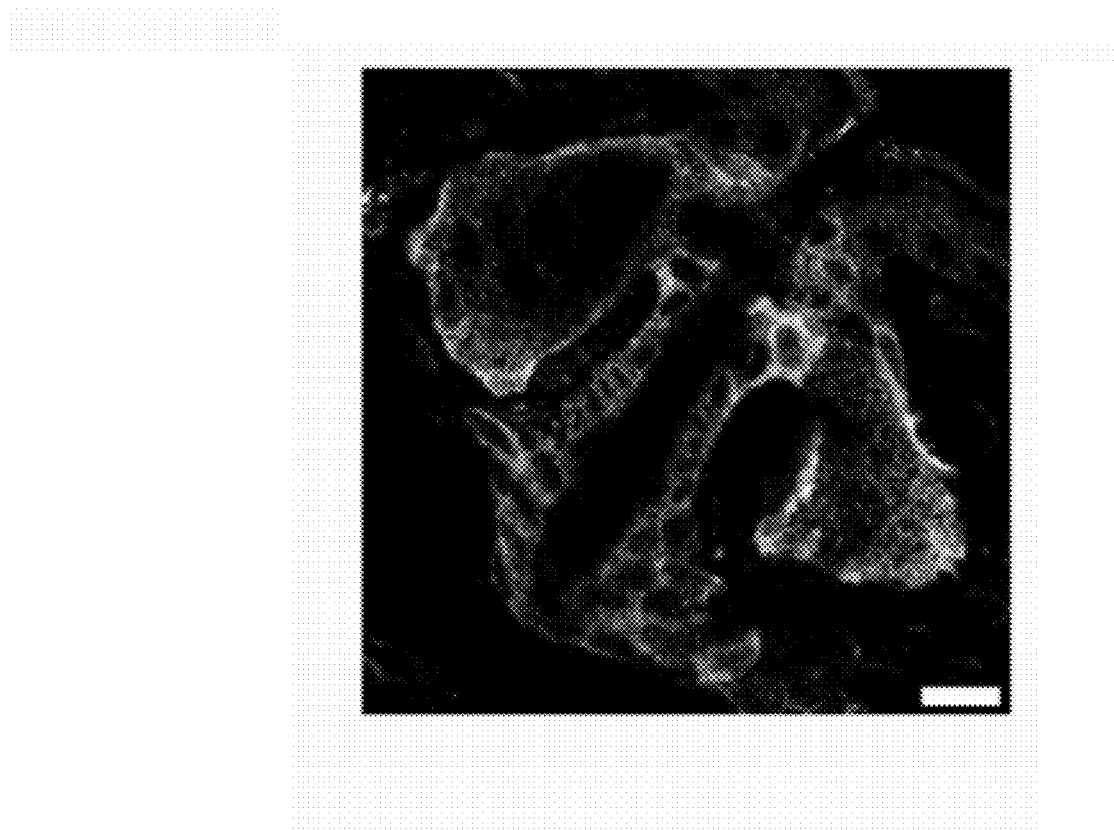
FIG. 19 shows localization of mMATE2 in the plasma membrane of a testicle Leydig cells. In the figure, the bar is 10 μm.
Figure 20:
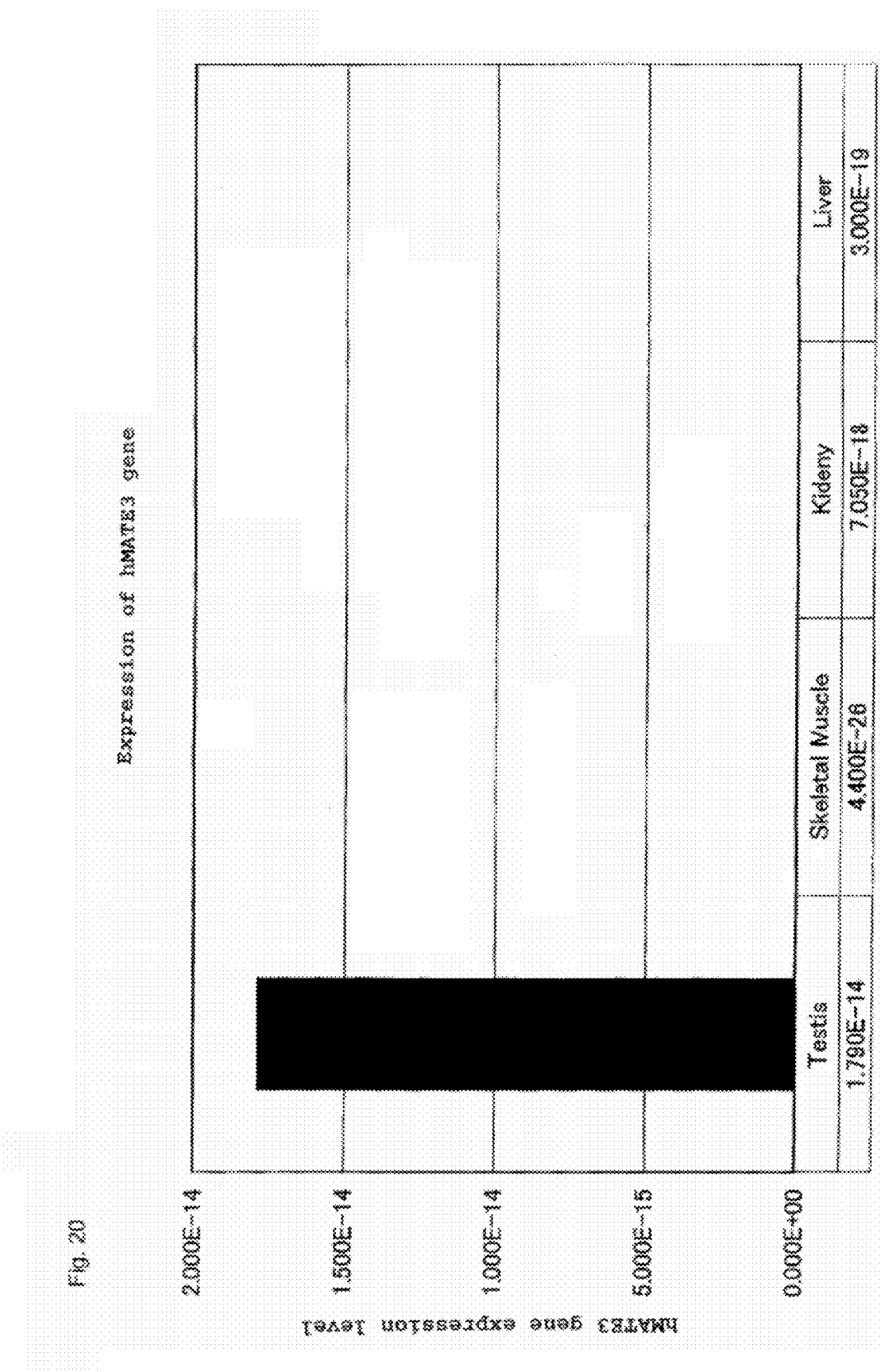
FIG. 20 shows the results of the examination of expression levels of the hMATE3 gene in the testicle, skeletal muscles, kidneys, and liver by RT-PCR. It is shown that the hMATE3 gene is expressed only in the testicle as in the case of mMATE2.

Furthermore, mouse MATE2 was found to be expressed specifically in the testicle Leydig cells, which secrete steroid hormones such as testosterone in the testicle (FIG. 19). This indirectly suggests that MATE2 transports steroid hormones and supports the results shown in Table 1. Therefore, MATE2 is considered to be a steroid hormone transporter. Since human MATES and mouse MATE2 have a very high homology, and the expression sites are similar (FIG. 20), MATE2 is considered to play similar roles in humans.

Furthermore, quercetin, a plant flavonoid, is known to be accumulated in vacuoles of plants, but the function thereof is unknown. According to the present invention, it is suggested that MATE1-like transporter functions as a transporter of plant flavonoids in a plant.

Since MATE1 and MATE2 are expressed in organs other than the kidneys and the liver, it is suggested that MATE-type transporters have functions other than that of the OC transporter. That is, it appears that MATE-type transporters functionally control transport of physiological metabolites having various sizes, structures, and hydrophobicity and are responsible for the molecular mechanism for maintaining electrolyte homeostasis in an organism.

It is known that the MATE gene is included in about 80 deficient genes in patients with Smith-Magenis syndrome, which is caused by abnormal 17q11.2 chromosome and presents diverse congenital deformities and mild mental growth retardation (for example, refer to Non-patent Documents 16 and 17). It is considered that patients with Smith-Magenis syndrome lack the H$^+$/OC transporter, and further studies based on the present invention can clarify the relationship between symptoms of this syndrome and the MATE family. Furthermore, the mammal MATE molecule of the present invention can bring about a breakthrough in studies of interactions of toxins, chemicals, and metabolites in an organism, gene polymorphism, and gene mutation. Furthermore, it is considered that, in plants, MATE of the plant is involved in resistance to chemicals or resistance to endogenous toxic metabolites. Thus, the MATE family is fundamental OC transporters in nature and plays a wide variety of roles in excretion of OCs and related compounds thereof.

It is noted that specific embodiments or examples explained in the Best Mode for Carrying Out the Invention are intended to clarify the technical content of the present invention, and the present invention should not be construed in any limitative way to such specific examples and can be implemented with various changes unless they depart from the spirit of the present invention and the following appended claims.

INDUSTRIAL APPLICABILITY

A chemical that regulates excretion of a chemical and/or a waste (for example, drugs, agricultural chemicals, and the like) can be screened for by using the present invention. Furthermore, nephrotoxicity and/or hepatotoxicity of a chemical can be tested by using the present invention. Furthermore, the present invention can be utilized as an experimental system for measuring transport, secretion, accumulation, or excretion of many biological components (in particular, highly hydrophobic biological components) such as absorption or excretion of monoamines, volatile organic cations, and nicotine, secretion, absorption, or excretion of melatonin, steroid hormones, sex hormones, and related formulations thereof, and concentration of plant alkanoids (alkaloids) or phenols in the plant body, and so forth.

Since a chemical that regulates excretion of a chemical and/or a waste (for example, drugs, agricultural chemicals, and the like), which has not been found so far, can be screened for by using the present invention, and the present invention can contribute to development of new medical and pharmaceutical fields. Furthermore, since nephrotoxicity and/or hepatotoxicity of an arbitrary chemical can be tested by using the present invention, the present invention can promote researches in medicine/pharmacy and contribute to development of research tools.

The invention claimed is:

1. A method for preparing a lipid membrane preparation for use in an assay for a candidate substrate of a transporter polypeptide, said method comprising the steps of isolating a lipid membrane comprising a polypeptide comprising the amino acid sequence of SEQ ID NO:4 from a host cell expressing said polypeptide, and incubating said lipid membrane with a substrate of said polypeptide, wherein the substrate is transported across said lipid membrane by said polypeptide, thereby preparing said lipid membrane preparation.

2. A kit for preparing a lipid membrane preparation, said kit comprising a vector containing a polynucleotide encoding a polypeptide comprising the amino acid sequence of SEQ ID NO: 4 and a substrate of said polypeptide, wherein the substrate is transported across said lipid membrane by said polypeptide and wherein the substrate is selected from the group consisting of tetraethylammonium (TEA), 1-methyl-4-phenylpyridinium (MPP), nicotine, cimetidine, quinidine, verapamil, quinine, melatonin, steroid hormones, excreted chemical, waste, corticosterone, Rhodamine 123, testosterone, progesterone, androsterone, quercetin, Rhodamine 6G, chloroquine, pyrimethamine, chlorpromazine, berberine, cisplatin, propranolol, papaverine, and thiamin.

3. A method for screening for a candidate substrate of a transporter polypeptide comprising the steps of incubating an isolated lipid membrane containing a transporter polypeptide comprising the amino acid sequence of SEQ ID NO: 4 with a candidate substrate; determining whether said candidate substrate is transported by the transporter polypeptide across said isolated lipid membrane; and identifying a candidate substrate that is transported by the transporter polypeptide as a substrate of the transporter polypeptide.

4. The method according to claim 3, further comprising a step of providing a pH gradient wherein pH decreases towards the direction to which the candidate substrate is transported, between the two domains subdivided by the lipid membrane.

5. The method according to claim 4, wherein the lipid membrane forms a vesicle in which the inner pH is lower than the outer pH.

6. The method according to claim 5, wherein the pH inside the vesicle is 6.5-7.5, and the pH outside the vesicle is 8.0-8.5.

7. The method according to any one of claims 3 to 6, wherein the lipid membrane further comprises $H^+$-ATPase protein.

8. A kit for screening for a candidate substrate of a transporter polypeptide, said kit comprising an isolated lipid membrane containing a transporter polypeptide comprising the amino acid sequence of SEQ ID NO: 4 and a substrate of said polypeptide, wherein the substrate is transported across said lipid membrane by said polypeptide and wherein the substrate is selected from the group consisting of tetraethylammonium (TEA), 1-methyl-4-phenylpyridinium (MPP), nicotine, cimetidine, quinidine, verapamil, quinine, melatonin, steroid hormone, excreted chemical, waste, corticosterone, Rhodamine 123, testosterone, progesterone, androsterone, quercetin, Rhodamine 6G, chloroquine, pyrimethamine, chlorpromazine, berberine, cisplatin, propranolol, papaverine, and thiamin.

9. The kit according to claim 8, wherein the isolated lipid membrane further comprises $H^+$-ATPase protein.

10. A method for screening for a candidate chemical which regulates substrate transport across a cell membrane via a transporter polypeptide, comprising the steps of incubating an isolated lipid membrane containing a polypeptide comprising the amino acid sequence of SEQ ID NO:4 together with the substrate of said polypeptide, wherein the substrate is transported across the membrane by said polypeptide, and the candidate chemical; determining whether substrate transport is regulated by said candidate chemical; and identifying a candidate chemical that regulates substrate transport as a chemical regulator of substrate transport.

11. The method according to claim 10, wherein the substrate is selected from the group consisting of tetraethylammonium (TEA), 1-methyl-4-phenylpyridinium (MPP), nicotine, cimetidine, quinidine, verapamil, quinine, melatonin, steroid hormone, excreted chemical, waste, corticosterone, Rhodamine 123, testosterone, progesterone, androsterone, quercetin, Rhodamine 6G, chloroquine, pyrimethamine, chlorpromazine, berberine, cisplatin, propranolol, papaverine, and thiamin.

12. The method according to claim 10, further comprising a step of providing a pH gradient wherein pH decreases towards the direction to which the substrate is transported, between the two domains subdivided by the lipid membrane.

13. The method according to claim 12, wherein the lipid membrane forms a vesicle in which the inner pH is lower than the outer pH.

14. The method according to claim 13, wherein the pH inside the vesicle is 6.5-7.5, and the pH outside the vesicle is 8.0-8.5.

15. The method according to any one of claims 10 to 14, wherein the lipid membrane further comprises $H^+$-ATPase protein.

16. The method of claim 1, wherein the polypeptide consists of the amino acid sequence of SEQ ID NO: 4.

17. The kit of claim 2, wherein the polypeptide consists of the amino acid sequence of SEQ ID NO: 4.

18. The kit of claim 8, wherein the polypeptide consists of the amino acid sequence of SEQ ID NO: 4.

* * * * *

SEQUENCE LISTING

<160> NUMBER OF SEQ ID NOS: 22

<210> SEQ ID NO 1
<211> LENGTH: 1713
<212> TYPE: DNA
<213> ORGANISM: human

<400> SEQUENCE: 1

```
atggaagctc ctgaggagcc cgcgccagtg cgcggaggcc cggaggccac ccttgaggtc      60
cgtgggtcgc gctgcttgcg gctgtccgcc ttccgagaag agctgcgggc gctcttggtc     120
ctggctggcc ccgcgttctt ggttcagctg atggtgttcc tgatcagctt cataagctcc     180
gtgttctgtg gccacctggg caagctggag ctggatgcag tcacgctggc aatcgcggtt     240
atcaatgtca ctggtgtctc agtgggattc ggcttatctt ctgcctgtga caccctcatc     300
tcccagacgt acgggagcca gaacctgaag cacgtgggcg tgatcctgca gcggagtgcg     360
ctcgtcctgc tcctctgctg cttcccctgc tgggcgctct ttctcaacac ccagcacatc     420
ctgctgctct tcaggcagga cccagatgtg tccaggctta cccagaccta tgtcacgatc     480
ttcattccag ctcttcctgc aacctttctt tatatgttac aagttaaata tttgctcaac     540
cagggaattg tactgcccca gatcgtaact ggagttgcag ccaacctcgt caatgccctc     600
gccaactatc tgtttctcca tcaactgcat cttggggtga taggctctgc actggcaaac     660
ttgatttccc agtacaccct ggctctactc ctctttctct acatccttgg gaaaaaactg     720
catcaagcta catggggagg ctggtccctc gagtgcctgc aggactgggc ctccttcctc     780
cgcctggcca tccccagcat gctcatgctg tgcatggagt ggtgggccta tgaggtcggg     840
agcttcctca gtggcatcct cggcatggtg gagctgggcg ctcagtccat cgtgtatgaa     900
ctggccatca ttgtgtacat ggtccctgca ggcttcagtg tggctgccag tgtccgggta     960
ggaaacgctc tgggtgctgg agacatggag caggcacgga agtcctctac cgtttccctg    1020
ctgattacag tgctctttgc tgtagccttc agtgtcctgc tgttaagctg taaggatcac    1080
gtggggtaca tttttactac cgaccgagac atcattaatc tggtggctca ggtggttcca    1140
atttatgctg tttcccacct ctttgaagct cttgcttgca cgagtggtgg tgttctgagg    1200
gggagtggaa atcagaaggt tggagccatt gtgaatacca ttgggtacta tgtggttggc    1260
ctccccatcg ggatcgcgct gatgtttgca accacacttg gagtgatggg tctgtggtca    1320
gggatcatca tctgtacagt cttttcaagct gtgtgttttc taggctttat tattcagcta    1380
aattggaaaa aagcctgtca gcaggctcag gtacacgcca atttgaaagt aaacaacgtg    1440
cctcggagtg ggaattctgc tctccctcag gatccgcttc acccagggtg ccctgaaaac    1500
cttgaaggaa ttttaacgaa cgatgttgga aagacaggcg agcctcagtc agatcagcag    1560
atgcgccaag aagaaccttt gccggaacat ccacaggacg gcgctaaatt gtccaggaaa    1620
cagctggtgc tgcggcgagg gcttctgctc ctgggggtct tcttaatctt gctggtgggg    1680
attttagtga gattctatgt cagaattcag tga                                 1713
```

```
<210> SEQ ID NO 2
<211> LENGTH: 570
<212> TYPE: PRT
<213> ORGANISM: human

<400> SEQUENCE: 2
```

| | | | | | | | | | | | | | | |
|---|---|---|---|---|---|---|---|---|---|---|---|---|---|---|
| Met | Glu | Ala | Pro | Glu | Pro | Ala | Pro | Val | Arg | Gly | Gly | Pro | Glu | Ala |
| 1 | | | | 5 | | | | | 10 | | | | | 15 |
| Thr | Leu | Glu | Val | Arg | Gly | Ser | Arg | Cys | Leu | Arg | Leu | Ser | Ala | Phe | Arg |
| | | | | 20 | | | | | 25 | | | | | 30 |
| Glu | Glu | Leu | Arg | Ala | Leu | Leu | Val | Leu | Ala | Gly | Pro | Ala | Phe | Leu | Val |
| | | | 35 | | | | | 40 | | | | | 45 |
| Gln | Leu | Met | Val | Phe | Leu | Ile | Ser | Phe | Ile | Ser | Ser | Val | Phe | Cys | Gly |
| | | 50 | | | | | 55 | | | | | 60 |
| His | Leu | Gly | Lys | Leu | Glu | Leu | Asp | Ala | Val | Thr | Leu | Ala | Ile | Ala | Val |
| 65 | | | | | 70 | | | | | 75 | | | | | 80 |
| Ile | Asn | Val | Thr | Gly | Val | Ser | Val | Gly | Phe | Gly | Leu | Ser | Ala | Cys |
| | | | | 85 | | | | | 90 | | | | | 95 |
| Asp | Thr | Leu | Ile | Ser | Gln | Thr | Tyr | Gly | Ser | Gln | Asn | Leu | Lys | His | Val |
| | | | 100 | | | | | 105 | | | | | 110 |
| Gly | Val | Ile | Leu | Gln | Arg | Ser | Ala | Leu | Val | Leu | Leu | Cys | Cys | Phe |
| | | 115 | | | | | 120 | | | | | 125 |
| Pro | Cys | Trp | Ala | Leu | Phe | Leu | Asn | Thr | Gln | His | Ile | Leu | Leu | Leu | Phe |
| | 130 | | | | | 135 | | | | | 140 |
| Arg | Gln | Asp | Pro | Asp | Val | Ser | Arg | Leu | Thr | Gln | Thr | Tyr | Val | Thr | Ile |
| 145 | | | | | 150 | | | | | 155 | | | | | 160 |
| Phe | Ile | Pro | Ala | Leu | Pro | Ala | Thr | Phe | Leu | Tyr | Met | Leu | Gln | Val | Lys |
| | | | | 165 | | | | | 170 | | | | | 175 |
| Tyr | Leu | Leu | Asn | Gln | Gly | Ile | Val | Leu | Pro | Gln | Ile | Val | Thr | Gly | Val |
| | | | 180 | | | | | 185 | | | | | 190 |
| Ala | Ala | Asn | Leu | Val | Asn | Ala | Leu | Ala | Asn | Tyr | Leu | Phe | Leu | His | Gln |
| | | 195 | | | | | 200 | | | | | 205 |
| Leu | His | Leu | Gly | Val | Ile | Gly | Ser | Ala | Leu | Ala | Asn | Leu | Ile | Ser | Gln |
| | 210 | | | | | 215 | | | | | 220 |
| Tyr | Thr | Leu | Ala | Leu | Leu | Leu | Phe | Leu | Tyr | Ile | Leu | Gly | Lys | Lys | Leu |
| 225 | | | | | 230 | | | | | 235 | | | | | 240 |
| His | Gln | Ala | Thr | Trp | Gly | Gly | Trp | Ser | Leu | Glu | Cys | Leu | Gln | Asp | Trp |
| | | | | 245 | | | | | 250 | | | | | 255 |
| Ala | Ser | Phe | Leu | Arg | Leu | Ala | Ile | Pro | Ser | Met | Leu | Met | Leu | Cys | Met |
| | | | 260 | | | | | 265 | | | | | 270 |
| Glu | Trp | Trp | Ala | Tyr | Glu | Val | Gly | Ser | Phe | Leu | Ser | Gly | Ile | Leu | Gly |
| | | 275 | | | | | 280 | | | | | 285 |
| Met | Val | Glu | Leu | Gly | Ala | Gln | Ser | Ile | Val | Tyr | Glu | Leu | Ala | Ile | Ile |
| | 290 | | | | | 295 | | | | | 300 |
| Val | Tyr | Met | Val | Pro | Ala | Gly | Phe | Ser | Val | Ala | Ala | Ser | Val | Arg | Val |
| 305 | | | | | 310 | | | | | 315 | | | | | 320 |
| Gly | Asn | Ala | Leu | Gly | Ala | Gly | Asp | Met | Glu | Gln | Ala | Arg | Lys | Ser | Ser |
| | | | | 325 | | | | | 330 | | | | | 335 |
| Thr | Val | Ser | Leu | Leu | Ile | Thr | Val | Leu | Phe | Ala | Val | Ala | Phe | Ser | Val |
| | | | 340 | | | | | 345 | | | | | 350 |
| Leu | Leu | Leu | Ser | Cys | Lys | Asp | His | Val | Gly | Tyr | Ile | Phe | Thr | Thr | Asp |
| | | 355 | | | | | 360 | | | | | 365 |
| Arg | Asp | Ile | Ile | Asn | Leu | Val | Ala | Gln | Val | Val | Pro | Ile | Tyr | Ala | Val |
| 370 | | | | | 375 | | | | | 380 |

| Ser | His | Leu | Phe | Glu | Ala | Leu | Ala | Cys | Thr | Ser | Gly | Val | Leu | Arg |
| --- | --- | --- | --- | --- | --- | --- | --- | --- | --- | --- | --- | --- | --- | --- |
| 385 | | | | 390 | | | | 395 | | | | 400 | | |

Gly Ser Gly Asn Gln Lys Val Gly Ala Ile Val Asn Thr Ile Gly Tyr
          405                 410                 415

Tyr Val Val Gly Leu Pro Ile Gly Ile Ala Leu Met Phe Ala Thr Thr
        420                 425                 430

Leu Gly Val Met Gly Leu Trp Ser Gly Ile Ile Ile Cys Thr Val Phe
    435                 440                 445

Gln Ala Val Cys Phe Leu Gly Phe Ile Ile Gln Leu Asn Trp Lys Lys
450                 455                 460

Ala Cys Gln Gln Ala Gln Val His Ala Asn Leu Lys Val Asn Asn Val
465                 470                 475                 480

Pro Arg Ser Gly Asn Ser Ala Leu Pro Gln Asp Pro Leu His Pro Gly
                485                 490                 495

Cys Pro Glu Asn Leu Glu Gly Ile Leu Thr Asn Asp Val Gly Lys Thr
            500                 505                 510

Gly Glu Pro Gln Ser Asp Gln Met Arg Gln Glu Pro Leu Pro
        515                 520                 525

Glu His Pro Gln Asp Gly Ala Lys Leu Ser Arg Lys Gln Leu Val Leu
    530                 535                 540

Arg Arg Gly Leu Leu Leu Leu Gly Val Phe Leu Ile Leu Leu Val Gly
545                 550                 555                 560

Ile Leu Val Arg Phe Tyr Val Arg Ile Gln
                565                 570

```
<210> SEQ ID NO 3
<211> LENGTH: 1809
<212> TYPE: DNA
<213> ORGANISM: human

<400> SEQUENCE: 3
atggacagcc tccaggacac agtggccctg accatgggg gctgctgccc tgccctcagc      60
aggctggttc ccagaggctt tgggactgag atgtggactc tctttgccct ttctggaccc     120
ctgttcctgt tccaggtgct gacttttatg atctacatcg tgagcactgt gttctgcggg     180
cacctgggca aggtggagct ggcatcggtg accctgcgcg tggcctttgt caatgtctgc     240
ggagtttctg taggagttgg tttgtcttcg gcatgtgaca ccttgatgtc tcagagcttc     300
ggcagcccca caagaagca cgtgggcgtg atcctgcagc ggggcgcgct ggtcctgctc     360
ctctgctgcc tccttgctg ggcgctcttc tcaacacccc agcacatcct gctgctcttc     420
cggcaggacc cggacgtgtc caggttgacc caggactatg taatgatttt cattccagga     480
cttccggtga ttttctttta caatctgctg caaaatatt tgcaaaatca gggatggctg     540
aaggggcagg aggaggagtc cccattccaa ccccgggtt tgtccatcct ccatccatct     600
cactcacacc ttagcagggc cagttttcat ttatttcaga agatcacctg ccccaagtc     660 ctcagtggtg tggtgggcaa ctgtgtcaac ggtgtggcca actatgccct ggtttctgtg     720
ctgaacctgg ggtcagggg ctccgcctat gccaacatca tctcccagtt tgcacagacc     780
gtcttcctcc ttctctacat tgtgctgaag aagctgcacc tggagacgtg gcaggttgg     840 tccagccagt gcctgcagga ctggggcccc ttcttctccc tggctgtccc cagcatgctc     900
atgatctgtg ttgagtggtg ggcctatgag atcgggagct cctcatggg gctgctcagt     960 gtggtggatc tctctgccca ggctgtcatc tacgaggtgg ccactgtgac ctacatgatt     1020
cccttggggc tcagcatcgg ggtctgtgtc cgagtgggga tggctctggg ggctgcggat     1080
```

| | |
|---|---|
| actgtgcagg ccaagcgctc ggccgtctcg ggcgtgctca gcatagttgg catttccctg | 1140 |
| gtcctgggca ccctgataag catcctgaaa atcagctggg gcatatttt taccaatgat | 1200 |
| gaagatgtca ttgccctggt gagccaggtc ttgccggttt atagtgtctt tcacgtgttt | 1260 |
| gaggccatct gttgtgtcta tggcggagtt ctgagaggaa ctgggaagca ggcctttggt | 1320 |
| gccgctgtga atgccatcac atattacatc atcggcctac cactgggcat ccttctgacc | 1380 |
| tttgtggtca gaatgagaat catgggcctc tgctgggca tgctggcctg tgtcttcctg | 1440 |
| gcaactgctg cctttgttgc ttatactgcc cggctggact ggaagcttgc tgcagaggag | 1500 |
| gctaagaaac attcaggccg gcagcagcag cagagagcag agagcactgc aaccagacct | 1560 |
| gggcctgaga aagcagtcct atcttcagtg gctacaggca gttcccctgg cattaccttg | 1620 |
| acaacgtatt caaggtctga gtgccacgtg gacttcttca ggactccaga ggaggcccac | 1680 |
| gcccttcag ctcctaccag cagactatca gtgaaacagc tggtcatccg ccgtggggct | 1740 |
| gctctggggg cggcgtcagc cacactgatg gtggggctca cggtcaggat cctagccacc | 1800 |
| aggcactag | 1809 |

<210> SEQ ID NO 4
<211> LENGTH: 602
<212> TYPE: PRT
<213> ORGANISM: human

<400> SEQUENCE: 4

```
Met Asp Ser Leu Gln Asp Thr Val Ala Leu Asp His Gly Gly Cys Cys
 1               5                  10                  15

Pro Ala Leu Ser Arg Leu Val Pro Arg Gly Phe Gly Thr Glu Met Trp
            20                  25                  30

Thr Leu Phe Ala Leu Ser Gly Pro Leu Phe Leu Phe Gln Val Leu Thr
        35                  40                  45

Phe Met Ile Tyr Ile Val Ser Thr Val Phe Cys Gly His Leu Gly Lys
    50                  55                  60

Val Glu Leu Ala Ser Val Thr Leu Ala Val Ala Phe Val Asn Val Cys
65                  70                  75                  80

Gly Val Ser Val Gly Val Gly Leu Ser Ser Ala Cys Asp Thr Leu Met
                85                  90                  95

Ser Gln Ser Phe Gly Ser Pro Asn Lys Lys His Val Gly Val Ile Leu
            100                 105                 110

Gln Arg Gly Ala Leu Val Leu Leu Cys Cys Leu Pro Cys Trp Ala
        115                 120                 125

Leu Phe Leu Asn Thr Gln His Ile Leu Leu Leu Phe Arg Gln Asp Pro
    130                 135                 140

Asp Val Ser Arg Leu Thr Gln Asp Tyr Val Met Ile Phe Ile Pro Gly
145                 150                 155                 160

Leu Pro Val Ile Phe Leu Tyr Asn Leu Leu Ala Lys Tyr Leu Gln Asn
                165                 170                 175

Gln Gly Trp Leu Lys Gly Gln Glu Glu Ser Pro Phe Gln Thr Pro
            180                 185                 190

Gly Leu Ser Ile Leu His Pro Ser His Ser His Leu Ser Arg Ala Ser
        195                 200                 205

Phe His Leu Phe Gln Lys Ile Thr Trp Pro Gly Val Leu Ser Gly Val
    210                 215                 220

Val Gly Asn Cys Val Asn Gly Val Ala Asn Tyr Ala Leu Val Ser Val
225                 230                 235                 240

Leu Asn Leu Gly Val Arg Gly Ser Ala Tyr Ala Asn Ile Ile Ser Gln
```

```
                245                 250                 255
Phe Ala Gln Thr Val Phe Leu Leu Leu Tyr Ile Val Leu Lys Lys Leu
            260                 265                 270
His Leu Glu Thr Trp Ala Gly Trp Ser Ser Gln Cys Leu Gln Asp Trp
        275                 280                 285
Gly Pro Phe Phe Ser Leu Ala Val Pro Ser Met Leu Met Ile Cys Val
    290                 295                 300
Glu Trp Trp Ala Tyr Glu Ile Gly Ser Phe Leu Met Gly Leu Leu Ser
305                 310                 315                 320
Val Val Asp Leu Ser Ala Gln Ala Val Ile Tyr Glu Val Ala Thr Val
                325                 330                 335
Thr Tyr Met Ile Pro Leu Gly Leu Ser Ile Gly Val Cys Val Arg Val
            340                 345                 350
Gly Met Ala Leu Gly Ala Ala Asp Thr Val Gln Ala Lys Arg Ser Ala
        355                 360                 365
Val Ser Gly Val Leu Ser Ile Val Gly Ile Ser Leu Val Leu Gly Thr
    370                 375                 380
Leu Ile Ser Ile Leu Lys Asn Gln Leu Gly His Ile Phe Thr Asn Asp
385                 390                 395                 400
Glu Asp Val Ile Ala Leu Val Ser Gln Val Leu Pro Val Tyr Ser Val
                405                 410                 415
Phe His Val Phe Glu Ala Ile Cys Cys Val Tyr Gly Gly Val Leu Arg
            420                 425                 430
Gly Thr Gly Lys Gln Ala Phe Gly Ala Ala Val Asn Ala Ile Thr Tyr
        435                 440                 445
Tyr Ile Ile Gly Leu Pro Leu Gly Ile Leu Thr Phe Val Val Arg
    450                 455                 460
Met Arg Ile Met Gly Leu Trp Leu Gly Met Leu Ala Cys Val Phe Leu
465                 470                 475                 480
Ala Thr Ala Ala Phe Val Ala Tyr Thr Ala Arg Leu Asp Trp Lys Leu
                485                 490                 495
Ala Ala Glu Glu Ala Lys Lys His Ser Gly Arg Gln Gln Gln Gln Arg
            500                 505                 510
Ala Glu Ser Thr Ala Thr Arg Pro Gly Pro Glu Lys Ala Val Leu Ser
        515                 520                 525
Ser Val Ala Thr Gly Ser Ser Pro Gly Ile Thr Leu Thr Thr Tyr Ser
    530                 535                 540
Arg Ser Glu Cys His Val Asp Phe Phe Arg Thr Pro Glu Glu Ala His
545                 550                 555                 560
Ala Leu Ser Ala Pro Thr Ser Arg Leu Ser Val Lys Gln Leu Val Ile
                565                 570                 575
Arg Arg Gly Ala Ala Leu Gly Ala Ala Ser Ala Thr Leu Met Val Gly
            580                 585                 590
Leu Thr Val Arg Ile Leu Ala Thr Arg His
        595                 600

<210> SEQ ID NO 5
<211> LENGTH: 1599
<212> TYPE: DNA
<213> ORGANISM: mouse

<400> SEQUENCE: 5
atggaacgca cggaggagtc cgctcccggg ccgggaggcg cggacgctgc gtccgagcgc      60
cgtgggctac gctgcctgct gctgcccggc ttcctagagg agctgcgggc actcttggtc     120
```

```
ctggcgggtc ctgcgttctt ggcccagctg atgatgttcc taatcagttt cataagctca    180
gtgttctgtg gccacttggg caagctggag ttggatgcag tcacactggc aattgcggtt    240
atcaatgtca caggcatttc agtgggacat ggcttgtctt ctgcttgtga cacgctcatc    300
tcccagacat acgggagcca gaacttaaag cacgtagggg ttatcctgca aggggggaca    360
ctcatcctgc tcctctgctg cttccctgc tgggcactct tcatcaacac cgagcaaatt    420
ctgctgctct tcagacagga cccggatgta tccaggctca cccagactta cgtcatgatc    480
ttcatcccag cgcttcctgc agcttttctt tatacgttac aagttaaata cttgctcaac    540
cagggcatcg ttctgcctca gattatgacg ggcatcgcag ctaaccttgt caacgccctg    600
gccaactatg tgtttctcta tcacctgcat cttggggtga tgggttcagc attggccaac    660
accatctccc agtttgccct ggccattttc ctgttcctct acatcctctg gagaagacta    720
caccaagcca cctggggagg gtggtcctgg gagtgtctgc aggactgggc tccttcctg    780
cgactggcta tccccagcat gctcatgctg tgcatagagt ggtgggccta tgaggttggc    840
agcttcctga gtggtatcct tggcatggtg gagttgggag cccagtccat cacctatgaa    900
ttggctatca ttgtatacat gatcccttca ggcttcagtg tggctgccaa cgtccgggtg    960
ggaaatgcac tgggcgcagg aaacattgac caggccaaga agtcctcagc tatttccttg    1020
atagtcacag agctctttgc tgtgaccttc tgcgtcctgc tgctaggctg taaggatctc    1080
gtgggctaca ttttcactac cgatcgggat atcgtggcct tggtggctca agtgatcccc    1140
atttatgctg tgtcccacct ctttgaaggt cttgcttgta cctgtggtgg tatcctgagg    1200
ggcactggga accagaaggt tggagccatc gttaatgcca tcgggtatta tgtcattggc    1260
ctccccatcg ggatcgcgct gatgtttgct gctaagctgg gagtgatcgg cctgtggtca    1320
ggcatcatca tctgcactac ctgtcagacc acgtgcttcc tggcttttat tgctcggctc    1380
aattggaaac gcgcctgtca acaggctcaa gtacatgcca atttgaaggt aaacgtggcc    1440
ctgaattccg ctgtctctca cgagcctgct cacccagtgt gtcctgagag ccatggagaa    1500
attatgatga cggatcttga aaaaaaaaga cgagactcag ttggaccagc cgatgaacca    1560
gcaacaagct tgcctatcc gtccaaagga cagcaataa                            1599
```

<210> SEQ ID NO 6
<211> LENGTH: 532
<212> TYPE: PRT
<213> ORGANISM: mouse

<400> SEQUENCE: 6

```
Met Glu Arg Thr Glu Glu Ser Ala Pro Gly Pro Gly Gly Ala Asp Ala
 1               5                  10                  15

Ala Ser Glu Arg Arg Gly Leu Arg Cys Leu Leu Leu Pro Gly Phe Leu
            20                  25                  30

Glu Glu Leu Arg Ala Leu Leu Val Leu Ala Gly Pro Ala Phe Leu Ala
        35                  40                  45

Gln Leu Met Met Phe Leu Ile Ser Phe Ile Ser Ser Val Phe Cys Gly
    50                  55                  60

His Leu Gly Lys Leu Glu Leu Asp Ala Val Thr Leu Ala Ile Ala Val
65                  70                  75                  80

Ile Asn Val Thr Gly Ile Ser Val Gly His Gly Leu Ser Ser Ala Cys
                85                  90                  95

Asp Thr Leu Ile Ser Gln Thr Tyr Gly Ser Gln Asn Leu Lys His Val
            100                 105                 110

Gly Val Ile Leu Gln Arg Gly Thr Leu Ile Leu Leu Leu Cys Cys Phe
```

```
                115                 120                 125
Pro Cys Trp Ala Leu Phe Ile Asn Thr Glu Gln Ile Leu Leu Leu Phe
130                 135                 140
Arg Gln Asp Pro Asp Val Ser Arg Leu Thr Gln Thr Tyr Val Met Ile
145                 150                 155                 160
Phe Ile Pro Ala Leu Pro Ala Ala Phe Leu Tyr Thr Leu Gln Val Lys
                165                 170                 175
Tyr Leu Leu Asn Gln Gly Ile Val Leu Pro Gln Ile Met Thr Gly Ile
                180                 185                 190
Ala Ala Asn Leu Val Asn Ala Leu Ala Asn Tyr Val Phe Leu Tyr His
                195                 200                 205
Leu His Leu Gly Val Met Gly Ser Ala Leu Ala Asn Thr Ile Ser Gln
210                 215                 220
Phe Ala Leu Ala Ile Phe Leu Phe Leu Tyr Ile Leu Trp Arg Arg Leu
225                 230                 235                 240
His Gln Ala Thr Trp Gly Gly Trp Ser Trp Glu Cys Leu Gln Asp Trp
                245                 250                 255
Ala Ser Phe Leu Arg Leu Ala Ile Pro Ser Met Leu Met Leu Cys Ile
                260                 265                 270
Glu Trp Trp Ala Tyr Glu Val Gly Ser Phe Leu Ser Gly Ile Leu Gly
                275                 280                 285
Met Val Glu Leu Gly Ala Gln Ser Ile Thr Tyr Glu Leu Ala Ile Ile
290                 295                 300
Val Tyr Met Ile Pro Ser Gly Phe Ser Val Ala Ala Asn Val Arg Val
305                 310                 315                 320
Gly Asn Ala Leu Gly Ala Gly Asn Ile Asp Gln Ala Lys Lys Ser Ser
                325                 330                 335
Ala Ile Ser Leu Ile Val Thr Glu Leu Phe Ala Val Thr Phe Cys Val
                340                 345                 350
Leu Leu Leu Gly Cys Lys Asp Leu Val Gly Tyr Ile Phe Thr Thr Asp
                355                 360                 365
Arg Asp Ile Val Ala Leu Val Ala Gln Val Ile Pro Ile Tyr Ala Val
370                 375                 380
Ser His Leu Phe Glu Gly Leu Ala Cys Thr Cys Gly Gly Ile Leu Arg
385                 390                 395                 400
Gly Thr Gly Asn Gln Lys Val Gly Ala Ile Val Asn Ala Ile Gly Tyr
                405                 410                 415
Tyr Val Ile Gly Leu Pro Ile Gly Ile Ala Leu Met Phe Ala Ala Lys
                420                 425                 430
Leu Gly Val Ile Gly Leu Trp Ser Gly Ile Ile Ile Cys Thr Thr Cys
                435                 440                 445
Gln Thr Thr Cys Phe Leu Ala Phe Ile Ala Arg Leu Asn Trp Lys Arg
450                 455                 460
Ala Cys Gln Gln Ala Gln Val His Ala Asn Leu Lys Val Asn Val Ala
465                 470                 475                 480
Leu Asn Ser Ala Val Ser His Glu Pro Ala His Pro Val Cys Pro Glu
                485                 490                 495
Ser His Gly Glu Ile Met Met Thr Asp Leu Glu Lys Lys Arg Arg Asp
                500                 505                 510
Ser Val Gly Pro Ala Asp Glu Pro Ala Thr Ser Phe Ala Tyr Pro Ser
                515                 520                 525
Lys Gly Gln Gln
                530
```

<210> SEQ ID NO 7
<211> LENGTH: 1722
<212> TYPE: DNA
<213> ORGANISM: mouse

<400> SEQUENCE: 7

```
atggagccgg ccgaggacag cctgggagcc accatccagc ccccggagct ggtccgcgtc      60
ccacggggc gcagtctgag gatcctgctg ggccttcgag gagcgctgtc ccccgacgtg     120
agacgggagg cggccgcgct agtggcgctc gcgggcccgg tgttcctggc gcagctgatg     180
atctttctca tcagcatcgt cagttccatc ttctgcggac acctgggcaa agtcgagttg     240
gacgccgtga cactcgctgt ttccgttgtg aatgtcactg gaatttcagt agggactggc     300
ttggcctcgg cttgtgacac actgatgtct cagtcctttg gaggcaagaa cttgaagcgc     360
gtggggtca tactccaaag gggcatcctc atcctgctgc tctgctgctt cccatgctgg     420
gccatcttcc tcaacaccga gcgcctgctg ctgctcctaa ggcaggaccc ggatgtcgcc     480
aggctagccc aggtttatgt gatgatatgc atccctgctc ttcctgcagc gttcctattc     540
cagctgcaga cgcggtattt acagagccag ggcatcatta tgccccaagt tattgttggg     600
atcgcagcaa atgtcgtcaa cgtgggcatg aacgccttct gctgtatgc cttggacctc     660
ggagtggtag gtcggcctg gccaacacc acctctcagt tcttcctgtc tgccctgctt     720
ttcctctacg tgtggtggaa gaaatccac atccacactt ggggagggtg gacaagggag     780
tgcttccagg agtggagctc ctacacgcgc ctggccatcc ccagtatgtt catggtgtgc     840
atcgagtggt ggaccttcga gattgggacc ttccttgcag gccttgttaa tgtgacagaa     900
ctgggagccc aggccgtcat ctatgaactg gcttctgtcg cctacatggt gcccttggc     960
tttggtgtgg ctgccagcgt ccgagtgggc aatgctctgg gggcagggaa cgctgaccag    1020
gcccggtgtt cctgtaccac tgttcttctg tgtgctggtg tctgtgcact cctggtgggg    1080
attctgctcg cagccttgaa ggatgtggtt gcctacatct tcaccaatga caaggacatc    1140
atttcccttg tgagtcaagt gatgcccatt tttgctccct tcatctcttt tgatgcactt    1200
gcgggcacct gtggcgggt cctgagaggc acgggaaaac aaaagatagg cgctgtcctg    1260
aacactatcg gttactacgg gtttggtttt cctattggag tgtccctgat gtttgctgct    1320
aagcttggga ataggcct ctgggctgga ctgatagtct gtgtctcctt ccaagccttc    1380
tcctatttaa tctacatcct gaggacaaac tggagcagag tcgcagagca ggcacaagtt    1440
cgagctgggc taaaaagcac caaggagttg atacccacgc cagcagatct gcccatcttg    1500
gaaagagaag ttatggatgg agtgattttg cctgatatca tcaggccaga gagtcagacc    1560
ggccagctgg tggtgaaga aacagccag tgtgcagtgc ccaccgttgg ggaggtcttg    1620
acggggagac agctggtttt ctatcgtggg atggctctga ctgtttctgt tgctgtcctc    1680
atagcaggga ttgtggtgcg agttttcaat gaccgtggct aa                     1722
```

<210> SEQ ID NO 8
<211> LENGTH: 573
<212> TYPE: PRT
<213> ORGANISM: mouse

<400> SEQUENCE: 8

Met Glu Pro Ala Glu Asp Ser Leu Gly Ala Thr Ile Gln Pro Pro Glu
1               5                   10                  15

Leu Val Arg Val Pro Arg Gly Arg Ser Leu Arg Ile Leu Leu Gly Leu
            20                  25                  30

```
Arg Gly Ala Leu Ser Pro Asp Val Arg Arg Glu Ala Ala Leu Val
     35                  40                  45

Ala Leu Ala Gly Pro Val Phe Leu Ala Gln Leu Met Ile Phe Leu Ile
 50                  55                  60

Ser Ile Val Ser Ser Ile Phe Cys Gly His Leu Gly Lys Val Glu Leu
 65                  70                  75                  80

Asp Ala Val Thr Leu Ala Val Ser Val Val Asn Val Thr Gly Ile Ser
                 85                  90                  95

Val Gly Thr Gly Leu Ala Ser Ala Cys Asp Thr Leu Met Ser Gln Ser
                100                 105                 110

Phe Gly Gly Lys Asn Leu Lys Arg Val Gly Val Ile Leu Gln Arg Gly
                115                 120                 125

Ile Leu Ile Leu Leu Leu Cys Cys Phe Pro Cys Trp Ala Ile Phe Leu
130                 135                 140

Asn Thr Glu Arg Leu Leu Leu Leu Arg Gln Asp Pro Asp Val Ala
145                 150                 155                 160

Arg Leu Ala Gln Val Tyr Val Met Ile Cys Ile Pro Ala Leu Pro Ala
                165                 170                 175

Ala Phe Leu Phe Gln Leu Gln Thr Arg Tyr Leu Gln Ser Gln Gly Ile
                180                 185                 190

Ile Met Pro Gln Val Ile Val Gly Ile Ala Ala Asn Val Val Asn Val
                195                 200                 205

Gly Met Asn Ala Phe Leu Leu Tyr Ala Leu Asp Leu Gly Val Val Gly
                210                 215                 220

Ser Ala Trp Ala Asn Thr Thr Ser Gln Phe Phe Leu Ser Ala Leu Leu
225                 230                 235                 240

Phe Leu Tyr Val Trp Trp Lys Arg Ile His Ile His Thr Trp Gly Gly
                245                 250                 255

Trp Thr Arg Glu Cys Phe Gln Glu Trp Ser Ser Tyr Thr Arg Leu Ala
                260                 265                 270

Ile Pro Ser Met Phe Met Val Cys Ile Glu Trp Trp Thr Phe Glu Ile
                275                 280                 285

Gly Thr Phe Leu Ala Gly Leu Val Asn Val Thr Glu Leu Gly Ala Gln
                290                 295                 300

Ala Val Ile Tyr Glu Leu Ala Ser Val Ala Tyr Met Val Pro Phe Gly
305                 310                 315                 320

Phe Gly Val Ala Ala Ser Val Arg Val Gly Asn Ala Leu Gly Ala Gly
                325                 330                 335

Asn Ala Asp Gln Ala Arg Cys Ser Cys Thr Thr Val Leu Leu Cys Ala
                340                 345                 350

Gly Val Cys Ala Leu Leu Val Gly Ile Leu Leu Ala Ala Leu Lys Asp
                355                 360                 365

Val Val Ala Tyr Ile Phe Thr Asn Asp Lys Asp Ile Ile Ser Leu Val
                370                 375                 380

Ser Gln Val Met Pro Ile Phe Ala Pro Phe His Leu Phe Asp Ala Leu
385                 390                 395                 400

Ala Gly Thr Cys Gly Gly Val Leu Arg Gly Thr Gly Lys Gln Lys Ile
                405                 410                 415

Gly Ala Val Leu Asn Thr Ile Gly Tyr Tyr Gly Phe Gly Phe Pro Ile
                420                 425                 430

Gly Val Ser Leu Met Phe Ala Ala Lys Leu Gly Ile Ile Gly Leu Trp
                435                 440                 445

Ala Gly Leu Ile Val Cys Val Ser Phe Gln Ala Phe Ser Tyr Leu Ile
450                 455                 460
```

Tyr Ile Leu Arg Thr Asn Trp Ser Arg Val Ala Glu Gln Ala Gln Val
465                 470                 475                 480

Arg Ala Gly Leu Lys Ser Thr Lys Glu Leu Ile Pro Thr Pro Ala Asp
                485                 490                 495

Leu Pro Ile Leu Glu Arg Glu Val Met Asp Gly Val Ile Leu Pro Asp
            500                 505                 510

Ile Ile Arg Pro Glu Ser Gln Thr Gly Gln Leu Val Glu Glu Asn
            515                 520                 525

Ser Gln Cys Ala Val Pro Thr Val Gly Glu Val Leu Thr Gly Arg Gln
            530                 535                 540

Leu Val Phe Tyr Arg Gly Met Ala Leu Thr Val Ser Val Ala Val Leu
545                 550                 555                 560

Ile Ala Gly Ile Val Val Arg Val Phe Asn Asp Arg Gly
                565                 570

<210> SEQ ID NO 9
<211> LENGTH: 456
<212> TYPE: PRT
<213> ORGANISM: Vibrio parahaemolyticus

<400> SEQUENCE: 9

Met His Arg Tyr Lys Glu Glu Ala Ser Ser Leu Ile Lys Leu Ala Thr
1               5                   10                  15

Pro Val Leu Ile Ala Ser Val Ala Gln Thr Gly Met Gly Phe Val Asp
                20                  25                  30

Thr Val Met Ala Gly Gly Val Ser Ala Thr Asp Met Ala Ala Val Ser
            35                  40                  45

Val Ala Ser Ser Ile Trp Leu Pro Ser Ile Leu Phe Gly Ile Gly Leu
        50                  55                  60

Leu Met Ala Leu Val Pro Val Ala Gln Leu Asn Gly Ser Ala Arg
65              70                  75                  80

Arg Glu Lys Ile Pro Phe Glu Ile Gln Gln Gly Val Val Leu Ala Leu
                85                  90                  95

Leu Ile Ser Ile Pro Ile Ile Gly Val Leu Leu Gln Thr Gln Phe Ile
                100                 105                 110

Leu Gln Leu Met Asp Val Glu Ala Val Met Ala Gly Lys Thr Val Gly
            115                 120                 125

Tyr Ile His Ala Val Ile Phe Ala Val Pro Ala Phe Leu Leu Phe Gln
130                 135                 140

Thr Leu Arg Ser Phe Thr Asp Gly Met Ser Leu Thr Lys Pro Ala Met
145                 150                 155                 160

Val Ile Gly Phe Ile Gly Leu Leu Leu Asn Ile Pro Leu Asn Trp Ile
                165                 170                 175

Phe Val Tyr Gly Lys Phe Gly Ala Pro Glu Leu Gly Gly Val Gly Cys
            180                 185                 190

Gly Val Ala Thr Thr Ile Val Tyr Trp Val Met Phe Ala Leu Leu Leu
        195                 200                 205

Ala Tyr Val Met Thr Ser Ser Arg Leu Lys Ser Ile Asn Val Phe Gly
    210                 215                 220

Glu Tyr His Lys Pro Gln Trp Lys Ala Gln Val Arg Leu Phe Lys Leu
225                 230                 235                 240

Gly Phe Pro Val Ala Ala Ala Leu Phe Phe Glu Val Thr Leu Phe Ala
                245                 250                 255

Val Val Ala Leu Leu Val Ser Pro Leu Gly Pro Ile Ile Val Ala Ala
            260                 265                 270

His Gln Val Ala Ile Asn Phe Ser Ser Leu Val Phe Met Leu Pro Met
    275                 280                 285

Ser Val Gly Ala Ala Val Ser Ile Arg Val Gly His Arg Leu Gly Glu
290                 295                 300

Glu Asn Val Asp Gly Arg Val Ala Ser Arg Val Gly Ile Met Val
305                 310                 315                 320

Gly Leu Ala Leu Ala Thr Ile Thr Ala Ile Ile Thr Val Leu Ser Arg
                325                 330                 335

Glu Leu Ile Ala Glu Leu Tyr Thr Asn Asn Pro Glu Val Ile Ser Leu
            340                 345                 350

Ala Met Gln Leu Leu Phe Ala Ala Val Tyr Gln Cys Thr Asp Ala
        355                 360                 365

Val Gln Val Ile Ala Ala Gly Ala Leu Arg Gly Tyr Lys Asp Met Arg
    370                 375                 380

Ala Ile Phe Asn Arg Thr Phe Ile Ala Tyr Trp Ile Leu Gly Leu Pro
385                 390                 395                 400

Thr Gly Tyr Ile Leu Gly Arg Thr Asp Trp Ile Val Glu Pro Met Gly
                405                 410                 415

Ala Gln Gly Phe Trp Leu Gly Phe Ile Ile Gly Leu Thr Ala Ala
            420                 425                 430

Leu Met Leu Gly Val Arg Leu Arg Trp Met His Arg Gln Glu Pro Asp
        435                 440                 445

Val Gln Leu Asn Phe Ser Leu Gln
    450                 455

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: oligo
      nucleotide for point mutation

<400> SEQUENCE: 10
ggcccaccac tgcatgcaca gcatgagc                                        28

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: oligo
      nucleotide for PCR primer

<400> SEQUENCE: 11
ggccggtacc cgcgagtcac atggaagctc                                      30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: oligo
      nucleotide for PCR primer

<400> SEQUENCE: 12
cacttctaga cctgtgaatt gtgtgtaagc                                      30

<210> SEQ ID NO 13
<211> LENGTH: 39
<212> TYPE: DNA

```
<213> ORGANISM: Artificial Sequence
<220> FEATURE:
<223> OTHER INFORMATION: Description of Artificial Sequence: oligo
      nucleotide for PCR primer

<400> SEQUENCE: 13
agtcgaattc caccatggac agcctccagg acacagtgg                              39

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: oligo
      nucleotide for PCR primer

<400> SEQUENCE: 14
agctctcgag ctagtgcctg gtggctagga tcctgac                                37

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: oligo
      nucleotide for PCR primer

<400> SEQUENCE: 15
cgccggtacc accatggaac gcacggagga                                        30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: oligo
      nucleotide for PCR primer

<400> SEQUENCE: 16
agacagttta ttgctgtcct ttggacggat                                        30

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: oligo
      nucleotide for PCR primer

<400> SEQUENCE: 17
caccgaattc atggagccgg ccgaggaca                                         29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: oligo
      nucleotide for PCR primer

<400> SEQUENCE: 18
cgtactcgag ttagccacgg tcattgaaa                                         29

<210> SEQ ID NO 19
<211> LENGTH: 86
<212> TYPE: PRT
<213> ORGANISM: human
```

<400> SEQUENCE: 19

Asn Trp Lys Lys Ala Cys Gln Gln Ala Gln Val His Ala Asn Leu Lys
1               5                   10                  15

Val Asn Asn Val Pro Arg Ser Gly Asn Ser Ala Leu Pro Gln Asp Pro
            20                  25                  30

Leu His Pro Gly Cys Pro Glu Asn Leu Glu Gly Ile Leu Thr Asn Asp
        35                  40                  45

Val Gly Lys Thr Gly Glu Pro Gln Ser Asp Gln Met Arg Gln Glu
    50                  55                  60

Glu Pro Leu Pro Glu His Pro Gln Asp Gly Ala Lys Leu Ser Arg Lys
65                  70                  75                  80

Gln Leu Val Leu Arg Arg
                85

<210> SEQ ID NO 20
<211> LENGTH: 38
<212> TYPE: PRT
<213> ORGANISM: mouse

<400> SEQUENCE: 20

Pro Glu Ser His Gly Glu Ile Met Met Thr Asp Leu Glu Lys Lys Arg
1               5                   10                  15

Arg Asp Ser Val Gly Pro Ala Asp Glu Pro Ala Thr Ser Phe Ala Tyr
            20                  25                  30

Pro Ser Lys Gly Gln Gln
        35

<210> SEQ ID NO 21
<211> LENGTH: 1680
<212> TYPE: DNA
<213> ORGANISM: human

<400> SEQUENCE: 21

| | |
|---|---|
| atgccagaaa gcgccagccc tcggctccgg gccctcggat ggcgtgacgg cttgtggggc | 60 |
| ctgcggggtg cgctgccccc ggacctgcgg ggggaggcgg ctgagctggc ggcgctcgcg | 120 |
| ggcccagtgt tcttgcgca gttgatgatc tttataatca gcctcgtcag ctccatcttc | 180 |
| tgtggacatc tgggcaaggt cgagccgac gctgtcacgc tcgccgtcac ggtggtgaac | 240 |
| gttactggga ttgcagttgg cactggctta gcctcagctt atgacaccct catgtctcag | 300 |
| tcctttggag tcaagaacct caagcgcgtg gggatcatac ttcagagagg gtcctcatc | 360 |
| cttatgctgt gctgctttcc ctgctgggcc gacttggtca caccgagcg catcctcctg | 420 |
| ctcttaaaac aagacccgaa gatagcccaa atttatgtgc tgattttcat tcctgcccctt | 480 |
| cctgcagcat tcttgttcca gctgcagaca agatatttac aaagtcaggg catcagcatg | 540 |
| cctcaagtta ttaccaggat tgcagctaat gtcatcaacg tgggcatgaa tgccctcttg | 600 |
| ctgtatgccc tggacttcag agtggtacag agtccctggc tctgtatgcc agagcgggc | 660 |
| atggttctat ttgttgtgat aaaatatgac ctatggaaga cactccatgt gcacactttg | 720 |
| ggaggttgga cgagggagtg cttccaggag tggggctcct acatccacct ggttattccc | 780 |
| agtatgttca tggtgtgcac tgagcagtgg acctttgaga tcggaaactt ccttgcagga | 840 |
| ctgattgatg tgatggagct cggcactcag gcatcatct gtgagctggc gtcagtggcc | 900 |
| tacatggtac ccctgggcct tggagttgca gccagcatcc gagtgggcaa tgctctgggg | 960 |
| gaagggaatg tagaggaggc ttggtgctcc tgcaccacag ttctcctgtg tgctggtgag | 1020 |
| tcaagcattc tactccctgg catctgtgct gaacttaagg atgtcctatc actaactact | 1080 |

```
ttcttttcct ctaacagaga tattacttcc cttgtgagcc aagtgatacc tattttttgcc   1140 ccttttcatc tatttgatgc acttgcaggc gcctgtggtg gagtcctgag aggtacagga   1200
aaacaaaaca ttggcgctat cttgaatgcc attgggtact atgtctttgg ttttcccatt   1260
ggagtatctc tgatgtttgc cactaaactc aggataatag gtctctggtc tggattgata   1320
gtttgtgtct tctttcaagc ccttttctat ctggtgtaca tcttgaggat aaactggagc   1380
aaagttgtgg agcaggcaca ggttcaagct ggactaaaag gaataaaaga gaccatgcct   1440
acctcctcag atctacctat cttgggaaga gaagtaactg atggaatcat tttgcctgat   1500
atcatcagac cagagagcca gaccccctcga ctgatgagac cagaagaaaa cacccagtat   1560
gcaatgtcca ccgctggaga ggtcctgaca gtgaggcagc tgatattcta tcatggaatg   1620
gctttagctc ttgctgtcac tttccttcca gcaggaattt tcattaagag ttttcaatga   1680
```

<210> SEQ ID NO 22
<211> LENGTH: 559
<212> TYPE: PRT
<213> ORGANISM: human

<400> SEQUENCE: 22

```
Met Pro Glu Ser Ala Ser Pro Arg Leu Arg Ala Leu Gly Trp Arg Asp
  1               5                  10                  15

Gly Leu Trp Gly Leu Arg Gly Ala Leu Pro Pro Asp Leu Arg Gly Glu
                 20                  25                  30

Ala Ala Glu Leu Ala Ala Leu Ala Gly Pro Val Phe Leu Ala Gln Leu
             35                  40                  45

Met Ile Phe Ile Ile Ser Leu Val Ser Ser Ile Phe Cys Gly His Leu
         50                  55                  60

Gly Lys Val Glu Pro Asp Ala Val Thr Leu Ala Val Thr Val Val Asn
 65                  70                  75                  80

Val Thr Gly Ile Ala Val Gly Thr Gly Leu Ala Ser Ala Tyr Asp Thr
                 85                  90                  95

Leu Met Ser Gln Ser Phe Gly Val Lys Asn Leu Lys Arg Val Gly Ile
            100                 105                 110

Ile Leu Gln Arg Gly Val Leu Ile Leu Met Leu Cys Cys Phe Pro Cys
        115                 120                 125

Trp Ala Asp Leu Val Asn Thr Glu Arg Ile Leu Leu Leu Leu Lys Gln
130                 135                 140

Asp Pro Lys Ile Ala Gln Ile Tyr Val Leu Ile Phe Ile Pro Ala Leu
145                 150                 155                 160

Pro Ala Ala Phe Leu Phe Gln Leu Gln Thr Arg Tyr Leu Gln Ser Gln
                165                 170                 175

Gly Ile Ser Met Pro Gln Val Ile Thr Arg Ile Ala Ala Asn Val Ile
            180                 185                 190

Asn Val Gly Met Asn Ala Leu Leu Leu Tyr Ala Leu Asp Phe Arg Val
        195                 200                 205

Val Gln Ser Pro Trp Leu Cys Met Pro Glu Arg Gly Met Val Leu Phe
    210                 215                 220

Val Val Ile Lys Tyr Asp Leu Trp Lys Thr Leu His Val His Thr Leu
225                 230                 235                 240

Gly Gly Trp Thr Arg Glu Cys Phe Gln Glu Trp Gly Ser Tyr Ile His
                245                 250                 255

Leu Val Ile Pro Ser Met Phe Met Val Cys Thr Glu Gln Trp Thr Phe
            260                 265                 270
```

-continued

```
Glu Ile Gly Asn Phe Leu Ala Gly Leu Ile Asp Val Met Glu Leu Gly
        275                 280                 285

Thr Gln Gly Ile Ile Cys Glu Leu Ala Ser Val Ala Tyr Met Val Pro
    290                 295                 300

Leu Gly Leu Gly Val Ala Ala Ser Ile Arg Val Gly Asn Ala Leu Gly
305                 310                 315                 320

Glu Gly Asn Val Glu Glu Ala Trp Cys Ser Cys Thr Thr Val Leu Leu
                325                 330                 335

Cys Ala Gly Glu Ser Ser Ile Leu Leu Pro Gly Ile Cys Ala Glu Leu
                340                 345                 350

Lys Asp Val Leu Ser Leu Thr Thr Phe Phe Ser Ser Asn Arg Asp Ile
            355                 360                 365

Thr Ser Leu Val Ser Gln Val Ile Pro Ile Phe Ala Pro Phe His Leu
        370                 375                 380

Phe Asp Ala Leu Ala Gly Ala Cys Gly Gly Val Leu Arg Gly Thr Gly
385                 390                 395                 400

Lys Gln Asn Ile Gly Ala Ile Leu Asn Ala Ile Gly Tyr Tyr Val Phe
                405                 410                 415

Gly Phe Pro Ile Gly Val Ser Leu Met Phe Ala Thr Lys Leu Arg Ile
                420                 425                 430

Ile Gly Leu Trp Ser Gly Leu Ile Val Cys Val Phe Phe Gln Ala Leu
            435                 440                 445

Phe Tyr Leu Val Tyr Ile Leu Arg Ile Asn Trp Ser Lys Val Val Glu
    450                 455                 460

Gln Ala Gln Val Gln Ala Gly Leu Lys Gly Asn Lys Glu Thr Met Pro
465                 470                 475                 480

Thr Ser Ser Asp Leu Pro Ile Leu Gly Arg Glu Val Thr Asp Gly Ile
                485                 490                 495

Ile Leu Pro Asp Ile Ile Arg Pro Glu Ser Gln Thr Pro Arg Leu Met
                500                 505                 510

Arg Pro Glu Glu Asn Thr Gln Tyr Ala Met Ser Thr Ala Gly Glu Val
            515                 520                 525

Leu Thr Val Arg Gln Leu Ile Phe Tyr His Gly Met Ala Leu Ala Leu
        530                 535                 540

Ala Val Thr Phe Leu Ser Ala Gly Ile Phe Ile Lys Ser Phe Gln
545                 550                 555
```